US007491537B2

(12) United States Patent
Fewell et al.

(10) Patent No.: US 7,491,537 B2

(45) Date of Patent: Feb. 17, 2009

(54) NUCLEIC ACID FORMULATIONS FOR GENE DELIVERY AND METHODS OF USE

(75) Inventors: Jason G Fewell, The Woodlands, TX (US); Fiona MacLaughlin, Houston, TX (US); Louis C Smith, Houston, TX (US); Francois Nicol, Menlo Park, CA (US); Alain Rolland, The Woodlands, TX (US)

(73) Assignee: Genetronics Biomedical Corporation, San Diego, CA (US)

( * ) Notice: Subject to any disclaimer, the term of this patent is extended or adjusted under 35 U.S.C. 154(b) by 23 days.

(21) Appl. No.: 11/561,847

(22) Filed: Nov. 20, 2006

(65) Prior Publication Data

US 2007/0213287 A1 Sep. 13, 2007

Related U.S. Application Data

(60) Division of application No. 10/234,406, filed on Sep. 3, 2002, now Pat. No. 7,173,116, which is a continuation of application No. PCT/US01/06953, filed on Mar. 2, 2001.

(60) Provisional application No. 60/187,236, filed on Mar. 3, 2000, provisional application No. 60/261,751, filed on Jan. 16, 2001.

(51) Int. Cl.

*C12N 15/00* (2006.01)
*C12N 15/87* (2006.01)
*A61K 31/715* (2006.01)
*C07K 1/00* (2006.01)

(52) U.S. Cl. ...................... 435/455; 435/461; 435/69.1; 435/320.1; 544/44; 530/300; 530/350

(58) Field of Classification Search ....................... None
See application file for complete search history.

(56) References Cited

U.S. PATENT DOCUMENTS

| | | | | |
|---|---|---|---|---|
| 4,543,252 A | 9/1985 | Lehrer et al. | .................. | 514/12 |
| 4,675,381 A | 6/1987 | Bichon | ....................... | 530/345 |
| 4,976,962 A | 12/1990 | Bichon et al. | ............... | 424/424 |
| 5,439,440 A | 8/1995 | Hofmann | ..................... | 604/20 |
| 5,679,647 A | 10/1997 | Carson et al. | ................. | 514/44 |
| 5,702,384 A | 12/1997 | Umeyama et al. | ........ | 604/892.1 |
| 5,704,908 A | 1/1998 | Hofmann et al. | .............. | 604/21 |
| 5,749,847 A * | 5/1998 | Zewert et al. | ............... | 604/501 |
| 5,856,435 A | 1/1999 | Bazile et al. | ................ | 530/300 |
| 5,904,936 A | 5/1999 | Huille et al. | ................ | 424/489 |
| 5,945,290 A * | 8/1999 | Cowsert | ........................ | 435/6 |
| 6,040,925 A | 3/2000 | Vondran, Jr. et al. | ........ | 358/525 |
| 6,048,551 A | 4/2000 | Hilfinger et al. | ............ | 424/501 |
| 6,096,335 A | 8/2000 | Thierry | ....................... | 535/450 |
| 6,271,205 B1 * | 8/2001 | Ross et al. | ..................... | 514/44 |
| 6,383,811 B2 | 5/2002 | Wolff et al. | ................. | 435/450 |
| 6,413,941 B1 | 7/2002 | Garnett et al. | ................ | 414/44 |
| 6,654,636 B1 * | 11/2003 | Dev et al. | ..................... | 604/21 |

FOREIGN PATENT DOCUMENTS

| | | |
|---|---|---|
| WO | WO 94/24983 | 11/1994 |
| WO | WO 95/24929 | 9/1995 |
| WO | WO 96/21470 | 7/1996 |
| WO | WO 98/19710 | 5/1998 |
| WO | WO 00/03694 | 1/2000 |
| WO | WO 00/30618 | 6/2000 |
| WO | WO 00/78357 | 12/2000 |
| WO | WO 00/78791 | 12/2000 |
| WO | WO 01/13723 | 3/2001 |

OTHER PUBLICATIONS

Trubetskoy et al.; "*Layer-by-layer deposition of oppositely charged polyelectrolytes on the surface of condensed DNA particles*;" Nucl. Acids Res.; vol. 27 No. 15; pp. 3090-3095; Aug. 1999.

Zhang et al.; "*Expression of Naked Plasmid DNA Injected into the Afferent and Efferent Vessels of Rodent and Dog Livers*;" Human Gene Therapy vol. 8; 1763-1772; Oct. 1997.

1998, Promega Biological Research Products Catalog, pp. 248 and 264.

GenBank Accession No. U47119; May 10, 2004.

Yeow et al.; "*Antiviral Activities of Individual Murine IFN-a Subtypes In Vivo: Intramuscular Inection of IFN Expression Constructs Reduces Cytomegalovirus Replication*;" J. Immunol.; vol. 160; pp. 2932-2939; 1998.

GenBank Accession No. AAB59737; Jun. 19, 2002.

Gen Accession No. AAA61621; Jan. 27, 1995.

Sigma Chemical Company Catalog; pp. 1742 and 1743; 1992.

Maniatis et al.; "*Molecular Cloning: A Laboratory Manual*;" Cold Spring Harbor Laboratory; pp. 86-95 and 448; 1982.

Abruzzese et al.; "*Ligand-Dependent Regulation of lasmid-Based Transgene Expression in Vivo*;" Human Gene Therapy; vol. 10; pp. 1499-1507; Jun. 10, 1999.

Aihara et al.; "*Gene transfer into muscle by electroporation in vivo*;" Nature Biotech; vol. 16; pp. 867-870; Sep. 1998.

Ayers et al.; "Polyacrylic acid mediated ocular delivery of ribozymes;" Journal of Controlled Release; vol. 38; pp. 167-175; 1996.

Bettan et al.; "*High-Level Protein Secretion into Blood Circulation after Electric Pulse-Mediated Gene Transfer into Skeletal Muscle*;" Molecular Therapy vol. 2, No. 3; pp. 204-210 Sep. 2000.

Bourne et al.; "*DNA Immunization against Experimental Genital Herpes Simplex Virus Infection*;" Journal of Infectious Diseases; vol. 173; pp. 800-807; Apr. 1996.

Chuah et al.; "*Gene therapy for hemophilia*;" Journal of Gene Medicine; vol. 3; pp. 3-20; Jan./Feb. 2001.

(Continued)

*Primary Examiner*—Richard Schnizer

(74) *Attorney, Agent, or Firm*—Wong, Cabello, Lutsch, Rutherford & Brucculeri, LLP; Marilyn M. Huston

(57) ABSTRACT

A nucleic acid formulation for use in gene delivery comprising a nucleic acid and an anionic polymer is disclosed. Examples of the anionic polymer includes anionic amino acid polymer or poly-amino acid (such as poly-L-glutamic acid, poly-D-glutamic acid, poly-L-aspartic acid, poly-D-aspartic acid), poly-acrylic acid, polynucleotides, poly galacturonic acid, and poly vinyl sulfate.

47 Claims, 13 Drawing Sheets

OTHER PUBLICATIONS

Connor et al.; "*Identification of polyamides that enhance adenovirus-mediated gene expression in the urothelium*;" Gene Therapy; vol. 8; pp. 41-48; Jan. 2001.
Davis et al.; "*Direct Gene Transfer into Skeletal Muscle In Vivo: Factors Affecting Efficiency of Transfer and Stability of Expression*;" Human Gene Therapy; vol. 4; pp. 151-159; 1993.
Dekie et al.; "*Poly-L-glutamic acid derivatives as vectors for gene therapy*;" Journal of Controlled Release; vol. 65; pp. 187-202; 2000.
Erbacher et al.; "*The reduction of the positive charges of polylysine by partial gluconoylation increases the transfection efficiency of polylysine/DNA*;" Biochimica et Biophysica Acta; vol. 1324; pp. 27-36; 1997.
Fewell et al.; "*Expression of factor IX in mice and hemophilic B dogs following intramuscular injection of PINC™ formulated plasmid with electroporation*;" Blood; vol. 96; p. 803A; 2000.
Fakhrai et al.; "*Eradication of established intracranial rat gliomas of transforming growth factor β antisense gene therapy*;" Proc. Nat. Acad. Sci. USA; vol. 93; pp. 2909-2914; Apr. 1996.
Goto et al.; "*Highly efficient electro-gene therapy of solid tumor by using an expression plasmid for the herpes simplex virus thymidine kinase gene*;" PNAS; vol. 97, No. 1; pp. 354-359: Jan. 2000.
Hagstrom et al.; "*Improved muscle-derived expression of human coagulation factor IX from a skeletal actin/CMV hybrid enhancer/promoter*;" Blood; vol. 95, No. 8; pp. 47-55; Apr. 2000.
Hagstrom et al.; "*Complexes of non-cationic liposomes and histone H1 mediate efficient transfection of DNA without encapsulation*;" Biochimica et Biophysica Acta; vol. 1284; pp. 47-55; 1996.
Hartikka et al.; "*Sodium phosphate enhances plasmid DNA expression in vivo*;" Gene Therapy; vol. 7; pp. 1171-1182; Feb. 2000.
Chao et al.; "*Persistent expression of canine factor IX in hemophilia B canines*;" Gene Therapy; vol. 6; pp. 1695-1704; 1999.
Herzog et al.; "*Long-term correction of canine hemophilia B by gene transfer of blood coagulation factor IX mediated by adeno-associated viral vector*;" Nature Medicine; vol. 5, No. 1; pp. 56-63; Jan. 1999.
Herzog et al.; "*Stable gene transfer and expression of human blood coagulation factor IX after intramuscular injection of recombinant adeno-associated virus*;" Proc. Natl. Acad. Sci. USA; vol. 94; pp. 5804-5809; May 1997.
Hoffman, et al.; "*Strategy for development of a pre-erythrocytic Plasmodium falciparum DNA vaccine for human use*;" Vaccine; vol. 15, No. 8; pp. 842-845; 1997.
Ichiba et al.; "*Single Chain Obervation on Collapse Transition in Gian DNA Induced by Negatively-Charged Polymer*;" Biochemical and Biophysical Research Communications; vol. 242; pp. 441-445; 1998.
Jaroszeski et al.; "*In vivo antitumor effects of electrochemotherapy in a hepatoma model*;" Biochimica et Biophysica Acta; vol. 1334; pp. 15-18; 1997.
Kay et al.; "*In Vivo Gene Therapy of Hemophilia B: Sustained Partial Correction in Factor IX-Deficient Dogs*;" Science; vol. 262; pp. 117-119; Oct. 1993.
Kaufman; "Advances toward Gene Therapy for Hemophilia at the Millennium;" *Human Gene Therapy*; vol. 10; pp. 2091-2107; Sep. 1999.
Kumar et al.; "*Genetic Vaccination: The advantages of going naked*;" Nature Medicine; vol. 2, No. 8; pp. 857-859; Aug. 1996.
Lee et al.; "*Surfactant-induced sealing of electropermeabilized skeletal muscle membranes in vivo*;" Proc. Natl. Acad. Sci. USA; vol. 89; pp. 4524-4528; May 1992.
Letvin et al.; "*Potent, protective anti-HIV immune responses generated by bimodal HIV envelope DNA plus protein vaccination*;" Proc. Natl. Acad. Sci. USA; vol. 94; pp. 9378-9383; Aug. 1997.
Levy et al.; "*Characterization of plasmid DNA transfer into mouse skeletal muscle: evaluation of uptake mechanism, expression and secretion of gene products into blood*;" Gene Therapy; vol. 3; pp. 201-211; Aug. 1995.
Liu et al.; "*DMA Vaccines: A New Era in Vaccinology: Overview of DNA Vaccines*;" Annals of the New York Academy of Sciences; vol. 772; pp. 15-20; Nov. 1995.
Lozier et al.; "*Adenovirus-Mediated Expression of Human Coagulation Factor IX in the Rhesus Macaque Is Associated with Dose-Limiting Toxicity*;" Blood; vol. 94, No. 12; pp. 3968-3975; Dec. 1999.
Luke et al.; "*An OspA-Based DNA Vaccine Protects Mice against Infection with Borrelia burgdorferi*;" Journal of Infectious Diseases; vol. 175; pp. 91-97; 1997.
Luo et al.; "*Controlled DNA Delivery Systems*;" Pharmaceutical Research; vol. 16, No. 8; pp. 1300-1308; 1999.
Mahato et al.; "*Biodistribution and Gene Expression of Lipid/Plasmid Complexes after Systemic Administration*;" Human Gene Therapy; vol. 9; pp. 2083-2099; Sep. 1998.
Kreiss et al.; "*Erythropoietin Secretion and Physiological Effect in Mouse after Intramuscular Plasmid DNA Electrotransfer*;" The Journal of Gene Medicine; vol. 1; pp. 245-250; 1999.
Ljung; "*Prophylactic Infusion Regimens in the Management of Hemophilia*;" Thrombosis and Haemostasis; vol. 82, No. 2; pp. 525-530; 1999.
Maruyama et al.; "*Continuous Erythropeitin Delivery by Muscle-Targeted Gene Transfer Using in Vivo Electroporation*;" Human Gene Therapy; vol. 11; 429-437; Feb. 2000.
Mathiesen; "*Electropermeabilization of skeletal muscle enhances gene transfer in vivo*;" Gene Therapy; vol. 6; pp. 508-514; 1999.
Mir et al.; "*High-efficiency gene transfer into skeletal muscle mediated by electric pulses*;" Proc. Natl. Acad. Sci. USA; vol. 96; pp. 4262-4267; Apr. 1999.
Mumper et al.; "*Plasmid delivery to muscle: Recent advances in polymer delivery systems*;" Advanced Drug Delivery Reviews; vol. 30; pp. 151-172; 1998.
Rizzuto et al.; "*Efficient and regulated erythropoietin Production by naked DNA injection and muscle electroporation*;" Proc. Natl. Acad. Sci. USA; vol. 96; pp. 6417-6422; May 1999.
Rolland; "*From Genes to Gene Medicines: Recent Advances in Nonviral Gene Delivery*;" Critical Reviews™ in Therapeutic Drug Carrier Systems; vol. 15, No. 2; pp. 143-198; 1998.
Snyder, et al.; "*Corrrection of hemophilia B in canine and murine models using recombinant adeno-associated viral vectors*;" Nature Medicine; vol. 5, No. 1; pp. 64-70; Jan. 1999.
Somiari et al.; "*Theory and in Vivo Application of Electroporative Gene Delivery*;" Molecular Therapy; vol. 2, No. 3; pp. 178-187; Sep. 2000.
Syrengelas et al.; "*DNA immunization induces protective immunity against B-cell lymphoma*;" Nature Medicine; vol. 2, No. 9; pp. 1038-1040; Sep. 1996.
Tedeschi et al.; "A Specific Antibody Response to HCV E2 Elicited in Mice by Intramuscular Inoculation of Plasmid DNA Containing Coding Sequences for E2;" Hepatology; vol. 25; pp. 459-462; 1997.
Ulmer et al.; "*DNA Vaccines*;" Current Opinion in Immunology; vol. 8; pp. 531-536; 1996.
Ulmer et al.; "*Heterologous Protection Against Influenza by Injection of DNA Encoding a Viral Protein*;" Science; vol. 259; pp. 1745-1749; Mar. 1993.
Cohen; "*Naked DNA Points Way to Vaccines*;" Science; vol. 259; pp. 1691-1692; Mar. 1993.
Yamashita et al.; "*Electroporation-mediated Interleukin-12 Gene Therapy for Hepatocellular Carcinoma in the Mice Model*;" Cancer Research; vol. 61; pp. 1005-1012; Feb. 2001.
Yeung et al.; "*Efficient infection of mature skeletal muscle with herpes simplex virus vectors by using dextran sulfate as a co-receptor*;" Gene Therapy; vol. 6; pp. 1536-1544; May 1999.
Wells et al.; "*Nonviral Transfer Technology Research Article: Electroporation-enhanced gene delivery in mammary tumors*;" Gene Therapy; vol. 7; pp. 541-547; Nov. 1999.
Wolff et al.; "*Expression of naked plasmids by cultured myotubes and entry of plasmids into T tubules and caveolae of mammalian skeletal muscle*;" Journal of Cell Science; vol. 103; pp. 1249-1259; 1992.
Xiang et al.; "*Immune Responses to Nucleic Acid Vaccines to Rabies Virus*;" Virology; vol. 209; pp. 569-579; 1995.
Zhang et al.; "*Depth-Targeted Efficient Gene Delivery and Expression in the Skin by Pulsed Electric Fields: An Approach to Gene Therapy of Skin Aging and Other Diseases*;" Biochemical and Biophysical Research Communications; vol. 220; pp. 633-636; 1996.

Lusher; "*Gene Therapy for Hemophilia A and B: Patient Selection and Follow-up, Requirements for a Cure*;" Thrombosis and Haemostatis; vol. 82, No. 3; pp. 572-575; 1999.

Muramatsu, et al.; "*Foreign Gene Expression in the Mouse Testis by Localized in Vivo Gene Transfer*;" Biochemical and Biophysical Research Communications; vol. 233; pp. 45-49; 1997.

Nishi et al.; "*High-Efficiency in Vivo Gene Transfer Using Intraarterial Plasmid DNA Injection following in Vivo Electroporation*;" Cancer Research; vol. 56; pp. 1050-1055; 1996.

Suzuki et al.; "*Direct gene transfer into rat liver cells by in vivo electroporation*;" FEBS Letters; vol. 425; pp. 436-440; 1998.

Titomirov et al.; "*In vivo electroporation and stable transformation of skin cells of newborn mice by plasmid DNA*;" Biochimica et Biophysica Acta; vol. 1088; pp. 131-134; 1991.

Turner et al.; "*Chracterisation of Peptide Condensed DNA/Anionic Liposome Gene Therapy Vectors*;" J Liposome Research; vol. 8; p. 114; 1998.

Fewell et al.; "*Gene Therapy for the Treatment of Hemophilia B Using PINC-Formulated Plasmid Delivered to Muscle with Electroporation*;" Molecular Therapy; vol. 3, No. 4; pp. 574-583; Apr. 2001.

Examination Report received in corresponding European Application No. 01 918 339.1 dated Nov. 11, 2004.

Feng et al.; "*Effect of non-ionic surfactants on the formation of DNA/emulsions complexes and emulsion-mediated gene transfer*;" Pharmaceutical Research; vol. 113, No. 11; pp. 1642-1646; 1996 (PREV199799334805).

* cited by examiner

```
                         SEQUENCE LISTING

<160> NUMBER OF SEQ ID NOS: 8

<210> SEQ ID NO 1
<211> LENGTH: 3589
<212> TYPE: DNA
<213> ORGANISM: Artificial
<220> FEATURE:
<223> OTHER INFORMATION: Expression plasmid pIF0921 encoding for human
      interferon alpha (768) ... (1334).
<220> FEATURE:
<221> NAME/KEY: CDS
<222> LOCATION: (768)..(1334)
<223> OTHER INFORMATION: encoding human interferon alpha

<400> SEQUENCE: 1

cgttacataa cttacggtaa atggcccgcc tggctgaccg cccaacgacc cccgcccatt      60

gacgtcaata atgacgtatg ttcccatagt aacgccaata gggactttcc attgacgtca     120

atgggtggag tatttacggt aaactgccca cttggcagta catcaagtgt atcatatgcc     180

aagtacgccc cctattgacg tcaatgacgg taaatggccc gcctggcatt atgcccagta     240

catgacctta tgggactttc ctacttggca gtacatctac gtattagtca tcgctattac     300

catggtgatg cggttttggc agtacatcaa tgggcgtgga tagcggtttg actcacgggg     360

atttccaagt ctccacccca ttgacgtcaa tgggagtttg ttttggcacc aaaatcaacg     420

ggactttcca aaatgtcgta acaactccgc cccattgacg caaatgggcg gtaggcgtgt     480

acggtgggag gtctatataa gcagagctcg tttagtgaac cgtcagatcg cctggagacg     540

ccatccacgc tgttttgacc tccatagaag acaccgggac cgatccagcc tccgcggccg     600

ggaacggtgc attggaacgc ggattccccg tgttaattaa caggtaagtg tcttcctcct     660

gtttccttcc cctgctattc tgctcaacct tcctatcaga aactgcagta tctgtatttt     720

tgctagcagt aatactaacg gttctttttt tctcttcaca ggccacc atg gcc ttg       776
                                                    Met Ala Leu
                                                    1

acc ttt gct tta ctg gtg gcc ctc ctg gtg ctc agc tgc aag tca agc       824
Thr Phe Ala Leu Leu Val Ala Leu Leu Val Leu Ser Cys Lys Ser Ser
    5                   10                  15

tgc tct gtg ggc tgt gat ctg cct caa acc cac agc ctg ggt agc agg       872
Cys Ser Val Gly Cys Asp Leu Pro Gln Thr His Ser Leu Gly Ser Arg
20                  25                  30                  35
```

-continued

```
agg acc ttg atg ctc ctg gca cag atg agg aga atc tct ctt ttc tcc      920
Arg Thr Leu Met Leu Leu Ala Gln Met Arg Arg Ile Ser Leu Phe Ser
                40                  45                  50

tgc ttg aag aac aga cat gac ttt gga ttt ccc cag gag gag ttt ggc      968
Cys Leu Lys Asn Arg His Asp Phe Gly Phe Pro Gln Glu Glu Phe Gly
            55                  60                  65

aac cag ttc caa aag gct gaa acc atc cct gtc ctc cat gag atg atc     1016
Asn Gln Phe Gln Lys Ala Glu Thr Ile Pro Val Leu His Glu Met Ile
        70                  75                  80

cag cag atc ttc aat ctc ttc agc aca aag gac tca tct gct gct tgg     1064
Gln Gln Ile Phe Asn Leu Phe Ser Thr Lys Asp Ser Ser Ala Ala Trp
    85                  90                  95

gat gag acc ctc cta gac aaa ttc tac act gaa ctc tac cag cag ctg     1112
Asp Glu Thr Leu Leu Asp Lys Phe Tyr Thr Glu Leu Tyr Gln Gln Leu
100                 105                 110                 115

aat gac ctg gaa gcc tgt gtg ata cag ggg gtg ggg gtg aca gag act     1160
Asn Asp Leu Glu Ala Cys Val Ile Gln Gly Val Gly Val Thr Glu Thr
                120                 125                 130

ccc ctg atg aag gag gac tcc att ctg gct gtg agg aaa tac ttc caa     1208
Pro Leu Met Lys Glu Asp Ser Ile Leu Ala Val Arg Lys Tyr Phe Gln
            135                 140                 145

aga atc act ctc tat ctg aaa gag aag aaa tac agc cct tgt gcc tgg     1256
Arg Ile Thr Leu Tyr Leu Lys Glu Lys Lys Tyr Ser Pro Cys Ala Trp
        150                 155                 160

gag gtt gtc aga gca gaa atc atg aga tct ttt tct ttg tca aca aac     1304
Glu Val Val Arg Ala Glu Ile Met Arg Ser Phe Ser Leu Ser Thr Asn
    165                 170                 175

ttg caa gaa agt tta aga agt aag gaa tga atctagaaaa gccgaattct       1354
Leu Gln Glu Ser Leu Arg Ser Lys Glu
180                 185

gcaggaattg ggtggcatcc ctgtgacccc tccccagtgc ctctcctggc cctggaagtt   1414

gccactccag tgcccaccag ccttgtccta ataaaattaa gttgcatcat tttgtctgac   1474

taggtgtcct tctataatat tatggggtgg aggggggtgg tatggagcaa ggggcaagtt   1534

gggaagacaa cctgtagggc tcgagggggg gcccggtacc agcttttgtt ccctttagtg   1594

agggttaatt tcgagcttgg cgtaatcatg gtcatagctg tttcctgtgt gaaattgtta   1654

tccgctcaca attccacaca acatacgagc cggaagcata aagtgtaaag cctggggtgc   1714

ctaatgagtg agctaactca cattaattgc gttgcgctca ctgcccgctt tccagtcggg   1774

aaacctgtcg tgccagctgc attaatgaat cggccaacgc gcggggagag gcggtttgcg   1834

tattgggcgc tcttccgctt cctcgctcac tgactcgctg cgctcggtcg ttcggctgcg   1894

gcgagcggta tcagctcact caaaggcggt aatacggtta tccacagaat caggggataa   1954

cgcaggaaag aacatgtgag caaaaggcca gcaaaaggcc aggaaccgta aaaaggccgc   2014

gttgctggcg tttttccata ggctccgccc ccctgacgag catcacaaaa atcgacgctc   2074

aagtcagagg tggcgaaacc cgacaggact ataaagatac caggcgtttc cccctggaag   2134

ctccctcgtg cgctctcctg ttccgaccct gccgcttacc ggatacctgt ccgcctttct   2194

cccttcggga agcgtggcgc tttctcatag ctcacgctgt aggtatctca gttcggtgta   2254

ggtcgttcgc tccaagctgg gctgtgtgca cgaacccccc gttcagcccg accgctgcgc   2314

cttatccggt aactatcgtc ttgagtccaa cccggtaaga cacgacttat cgccactggc   2374

agcagccact ggtaacagga ttagcagagc gaggtatgta ggcggtgcta cagagttctt   2434

gaagtggtgg cctaactacg gctacactag aaggacagta tttggtatct gcgctctgct   2494
```

-continued

```
gaagccagtt accttcggaa aaagagttgg tagctcttga tccggcaaac aaaccaccgc   2554

tggtagcggt ggtttttttg tttgcaagca gcagattacg cgcagaaaaa aaggatctca   2614

agaagatcct ttgatctttt ctacggggtc tgacgctcag aagaactcgt caagaaggcg   2674

atagaaggcg atgcgctgcg aatcgggagc ggcgataccg taaagcacga ggaagcggtc   2734

agcccattcg ccgccaagct cttcagcaat atcacgggta gccaacgcta tgtcctgata   2794

gcggtccgcc acacccagcc ggccacagtc gatgaatcca gaaaagcggc cattttccac   2854

catgatattc ggcaagcagg catcgccatg cgtcacgacg agatcctcgc cgtcgggcat   2914

gcgcgccttg agcctggcga acagttcggc tggcgcgagc ccctgatgct cttcgtccag   2974

atcatcctga tcgacaagac cggcttccat ccgagtacgt gctcgctcga tgcgatgttt   3034

cgcttggtgg tcgaatgggc aggtagccgg atcaagcgta tgcagccgcc gcattgcatc   3094

agccatgatg gatactttct cggcaggagc aaggtgagat gacaggagat cctgccccgg   3154

cacttcgccc aatagcagcc agtcccttcc cgcttcagtg acaacgtcga gcacagctgc   3214

gcaaggaacg cccgtcgtgg ccagccacga tagccgcgct gcctcgtcct gcagttcatt   3274

cagggcaccg gacaggtcgg tcttgacaaa aagaaccggg cgcccctgcg ctgacagccg   3334

gaacacggcg gcatcagagc agccgattgt ctgttgtgcc cagtcatagc cgaatagcct   3394

ctccacccaa gcggccggag aacctgcgtg caatccatct tgttcaatca tgcgaaacga   3454

tcctcatcct gtctcttgat cagatcttga tcccctgcgc catcagatcc ttggcggcaa   3514

gaaagccatc cagtttactt tgcagggctt cccaacctta ccagagggcg aattcgagct   3574

tgcatgcctg caggt                                                    3589
```

```
<210> SEQ ID NO 2
<211> LENGTH: 188
<212> TYPE: PRT
<213> ORGANISM: Artificial
<220> FEATURE:
<223> OTHER INFORMATION: Synthetic Construct

<400> SEQUENCE: 2

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asn Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
```

-continued

```
                165                 170                 175

Ser Thr Asn Leu Gln Glu Ser Leu Arg Ser Lys Glu
            180                 185


<210> SEQ ID NO 3
<211> LENGTH: 3609
<212> TYPE: DNA
<213> ORGANISM: artificial
<220> FEATURE:
<223> OTHER INFORMATION: Expression plasmid pEP1403 encoding for mouse
      erythropoietin (801-1379)
<220> FEATURE:
<221> NAME/KEY: CDS
<222> LOCATION: (801)..(1379)
<223> OTHER INFORMATION: encoding mouse erythropoietin

<400> SEQUENCE: 3

aattcgagct tgcatgcctg caggtcgtta cataacttac ggtaaatggc ccgcctggct      60

gaccgcccaa cgacccccgc ccattgacgt caataatgac gtatgttccc atagtaacgc     120

caatagggac tttccattga cgtcaatggg tggagtattt acggtaaact gcccacttgg     180

cagtacatca agtgtatcat atgccaagta cgccccctat tgacgtcaat gacggtaaat     240

ggcccgcctg gcattatgcc cagtacatga ccttatggga ctttcctact tggcagtaca     300

tctacgtatt agtcatcgct attaccatgg tgatgcggtt ttggcagtac atcaatgggc     360

gtggatagcg gtttgactca cggggatttc caagtctcca ccccattgac gtcaatggga     420

gtttgttttg gcaccaaaat caacgggact ttccaaaatg tcgtaacaac tccgccccat     480

tgacgcaaat gggcggtagg cgtgtacggt gggaggtcta tataagcaga gctcgtttag     540

tgaaccgtca gatcgcctgg agacgccatc cacgctgttt tgacctccat agaagacacc     600

gggaccgatc cagcctccgc ggccgggaac ggtgcattgg aacgcggatt ccccgtgtta     660

attaacaggt aagtgtcttc ctcctgtttc cttcccctgc tattctgctc aaccttccta     720

tcagaaactg cagtatctgt atttttgcta gcagtaatac taacggttct ttttttctct     780

tcacaggcca ccaagcttcc atg ggg gtg ccc gaa cgc ccc acc ctg ctg ctg     833
                      Met Gly Val Pro Glu Arg Pro Thr Leu Leu Leu
                      1               5                   10

ctg ctc tcc ctg ctg ctg att cct ctg ggc ctc cca gtc ctc tgt gct      881
Leu Leu Ser Leu Leu Leu Ile Pro Leu Gly Leu Pro Val Leu Cys Ala
            15                  20                  25

ccc cca cgc ctc atc tgc gac agt cgg gtg ctg gag agg tac atc ctg      929
Pro Pro Arg Leu Ile Cys Asp Ser Arg Val Leu Glu Arg Tyr Ile Leu
        30                  35                  40

gag gcc aag gag gca gaa aat gtc acg atg ggt tgt gca gaa ggt ccc      977
Glu Ala Lys Glu Ala Glu Asn Val Thr Met Gly Cys Ala Glu Gly Pro
    45                  50                  55

aga ctg agt gaa aat att aca gtc cca gat acc aaa gtc aac ttc tat     1025
Arg Leu Ser Glu Asn Ile Thr Val Pro Asp Thr Lys Val Asn Phe Tyr
60                  65                  70                  75

gct tgg aaa aga atg gag gtg gaa gaa cag gcc atc gaa gtg tgg caa     1073
Ala Trp Lys Arg Met Glu Val Glu Glu Gln Ala Ile Glu Val Trp Gln
                80                  85                  90

ggc ctg tcc ctg ctc agc gaa gcc atc ctg cag gcc cag gcc ctg ctg     1121
Gly Leu Ser Leu Leu Ser Glu Ala Ile Leu Gln Ala Gln Ala Leu Leu
            95                  100                 105

gcc aat tcc tcc cag cca cca gag acc ctg cag ctg cat atc gac aaa     1169
Ala Asn Ser Ser Gln Pro Pro Glu Thr Leu Gln Leu His Ile Asp Lys
        110                 115                 120

gcc atc agt ggt ctg cgc agc ctc act tcc ctg ctg cgg gtg ctg gga     1217
```

-continued

```
Ala Ile Ser Gly Leu Arg Ser Leu Thr Ser Leu Leu Arg Val Leu Gly
    125                 130                 135

gct cag aag gaa ctg atg tcc cct cca gat acc acc cca cct gct cca     1265
Ala Gln Lys Glu Leu Met Ser Pro Pro Asp Thr Thr Pro Pro Ala Pro
140                 145                 150                 155

ctc cgc aca ctc aca gtg gat act ttc tgc aag ctc ttc cgg gtc tac     1313
Leu Arg Thr Leu Thr Val Asp Thr Phe Cys Lys Leu Phe Arg Val Tyr
                160                 165                 170

gcc aac ttc ctc cgg ggg aaa ctg aag ctg tac acg gga gag gtc tgc     1361
Ala Asn Phe Leu Arg Gly Lys Leu Lys Leu Tyr Thr Gly Glu Val Cys
            175                 180                 185

agg aga ggg gac agg tga gtctagaaaa gccgaattct gcaggaattg            1409
Arg Arg Gly Asp Arg
        190

ggtggcatcc ctgtgacccc tccccagtgc ctctcctggc cctggaagtt gccactccag   1469

tgcccaccag ccttgtccta ataaaattaa gttgcatcat tttgtctgac taggtgtcct   1529

tctataatat tatggggtgg aggggggtgg tatggagcaa ggggcaagtt gggaagacaa   1589

cctgtagggc tcgagggggg gcccggtacc agcttttgtt ccctttagtg agggttaatt   1649

tcgagcttgg cgtaatcatg gtcatagctg tttcctgtgt gaaattgtta tccgctcaca   1709

attccacaca acatacgagc cggaagcata aagtgtaaag cctggggtgc ctaatgagtg   1769

agctaactca cattaattgc gttgcgctca ctgcccgctt tccagtcggg aaacctgtcg   1829

tgccagctgc attaatgaat cggccaacgc gcggggagag gcggtttgcg tattgggcgc   1889

tcttccgctt cctcgctcac tgactcgctg cgctcggtcg ttcggctgcg gcgagcggta   1949

tcagctcact caaaggcggt aatacggtta tccacagaat caggggataa cgcaggaaag   2009

aacatgtgag caaaaggcca gcaaaaggcc aggaaccgta aaaaggccgc gttgctggcg   2069

tttttccata ggctccgccc ccctgacgag catcacaaaa atcgacgctc aagtcagagg   2129

tggcgaaacc cgacaggact ataaagatac caggcgtttc cccctggaag ctccctcgtg   2189

cgctctcctg ttccgaccct gccgcttacc ggatacctgt ccgcctttct cccttcggga   2249

agcgtggcgc tttctcatag ctcacgctgt aggtatctca gttcggtgta ggtcgttcgc   2309

tccaagctgg gctgtgtgca cgaacccccc gttcagcccg accgctgcgc cttatccggt   2369

aactatcgtc ttgagtccaa cccggtaaga cacgacttat cgccactggc agcagccact   2429

ggtaacagga ttagcagagc gaggtatgta ggcggtgcta cagagttctt gaagtggtgg   2489

cctaactacg gctacactag aaggacagta tttggtatct gcgctctgct gaagccagtt   2549

accttcggaa aaagagttgg tagctcttga tccggcaaac aaaccaccgc tggtagcggt   2609

ggtttttttg tttgcaagca gcagattacg cgcagaaaaa aaggatctca agaagatcct   2669

ttgatctttt ctacggggtc tgacgctcag aagaactcgt caagaaggcg atagaaggcg   2729

atgcgctgcg aatcgggagc ggcgataccg taaagcacga ggaagcggtc agcccattcg   2789

ccgccaagct cttcagcaat atcacgggta gccaacgcta tgtcctgata gcggtccgcc   2849

acacccagcc ggccacagtc gatgaatcca gaaaagcggc cattttccac catgatattc   2909

ggcaagcagg catcgccatg cgtcacgacg agatcctcgc cgtcgggcat gcgcgccttg   2969

agcctggcga acagttcggc tggcgcgagc ccctgatgct cttcgtccag atcatcctga   3029

tcgacaagac cggcttccat ccgagtacgt gctcgctcga tgcgatgttt cgcttggtgg   3089

tcgaatgggc aggtagccgg atcaagcgta tgcagccgcc gcattgcatc agccatgatg   3149

gatactttct cggcaggagc aaggtgagat gacaggagat cctgccccgg cacttcgccc   3209
```

```
aatagcagcc agtcccttcc cgcttcagtg acaacgtcga gcacagctgc gcaaggaacg   3269

cccgtcgtgg ccagccacga tagccgcgct gcctcgtcct gcagttcatt cagggcaccg   3329

gacaggtcgg tcttgacaaa aagaaccggg cgcccctgcg ctgacagccg gaacacggcg   3389

gcatcagagc agccgattgt ctgttgtgcc cagtcatagc cgaatagcct ctccacccaa   3449

gcggccggag aacctgcgtg caatccatct tgttcaatca tgcgaaacga tcctcatcct   3509

gtctcttgat cagatcttga tcccctgcgc catcagatcc ttggcggcaa gaaagccatc   3569

cagtttactt tgcagggctt cccaacctta ccagagggcg                         3609
```

<210> SEQ ID NO 4
<211> LENGTH: 192
<212> TYPE: PRT
<213> ORGANISM: artificial
<220> FEATURE:
<223> OTHER INFORMATION: Synthetic Construct

<400> SEQUENCE: 4

```
Met Gly Val Pro Glu Arg Pro Thr Leu Leu Leu Leu Leu Ser Leu Leu
1               5                   10                  15

Leu Ile Pro Leu Gly Leu Pro Val Leu Cys Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn Ser Ser Gln
            100                 105                 110

Pro Pro Glu Thr Leu Gln Leu His Ile Asp Lys Ala Ile Ser Gly Leu
        115                 120                 125

Arg Ser Leu Thr Ser Leu Leu Arg Val Leu Gly Ala Gln Lys Glu Leu
    130                 135                 140

Met Ser Pro Pro Asp Thr Thr Pro Pro Ala Pro Leu Arg Thr Leu Thr
145                 150                 155                 160

Val Asp Thr Phe Cys Lys Leu Phe Arg Val Tyr Ala Asn Phe Leu Arg
                165                 170                 175

Gly Lys Leu Lys Leu Tyr Thr Gly Glu Val Cys Arg Arg Gly Asp Arg
            180                 185                 190
```

<210> SEQ ID NO 5
<211> LENGTH: 4496
<212> TYPE: DNA
<213> ORGANISM: artificial
<220> FEATURE:
<223> OTHER INFORMATION: Expression plasmid pFN0945 having natural sequence encoding human coagulation factor IX
<220> FEATURE:
<221> NAME/KEY: CDS
<222> LOCATION: (782)..(2167)
<223> OTHER INFORMATION: human coagulation factor IX

<400> SEQUENCE: 5

```
ggtcgttaca taacttacgg taaatggccc gcctggctga ccgcccaacg acccccgccc     60

attgacgtca ataatgacgt atgttcccat agtaacgcca atagggactt tccattgacg    120
```

-continued

```
tcaatgggtg gagtatttac ggtaaactgc ccacttggca gtacatcaag tgtatcatat    180

gccaagtacg ccccctattg acgtcaatga cggtaaatgg cccgcctggc attatgccca    240

gtacatgacc ttatgggact ttcctacttg gcagtacatc tacgtattag tcatcgctat    300

taccatcatg gtgatgcggt tttggcagta catcaatggg cgtggatagc ggtttgactc    360

acggggattt ccaagtctcc accccattga cgtcaatggg agtttgtttt ggcaccaaaa    420

tcaacgggac tttccaaaat gtcgtaacaa ctccgcccca ttgacgcaaa tgggcggtag    480

gcgtgtacgg tgggaggtct atataagcag agctcgttta gtgaaccgtc agatcgcctg    540

gagacgccat ccacgctgtt ttgacctcca tagaagacac cgggaccgat ccagcctccg    600

cggccgggaa cggtgcattg gaacgcggat tccccgtgtt aattaacagg taagtgtctt    660

cctcctgttt ccttcccctg ctattctgct caaccttcct atcagaaact gcagtatctg    720

tatttttgct agcagtaata ctaacggttc ttttttctc ttcacaggcc acactggatc    780

c atg cag cgc gtg aac atg atc atg gca gaa tca cca ggc ctc atc acc    829
  Met Gln Arg Val Asn Met Ile Met Ala Glu Ser Pro Gly Leu Ile Thr
  1               5                   10                  15

atc tgc ctt tta gga tat cta ctc agt gct gaa tgt aca gtt ttt ctt      877
Ile Cys Leu Leu Gly Tyr Leu Leu Ser Ala Glu Cys Thr Val Phe Leu
            20                  25                  30

gat cat gaa aac gcc aac aaa att ctg aat cgg cca aag agg tat aat      925
Asp His Glu Asn Ala Asn Lys Ile Leu Asn Arg Pro Lys Arg Tyr Asn
        35                  40                  45

tca ggt aaa ttg gaa gag ttt gtt caa ggg aac ctt gag aga gaa tgt      973
Ser Gly Lys Leu Glu Glu Phe Val Gln Gly Asn Leu Glu Arg Glu Cys
    50                  55                  60

atg gaa gaa aag tgt agt ttt gaa gaa gca cga gaa gtt ttt gaa aac     1021
Met Glu Glu Lys Cys Ser Phe Glu Glu Ala Arg Glu Val Phe Glu Asn
65                  70                  75                  80

act gaa aga aca act gaa ttt tgg aag cag tat gtt gat gga gat cag     1069
Thr Glu Arg Thr Thr Glu Phe Trp Lys Gln Tyr Val Asp Gly Asp Gln
                85                  90                  95

tgt gag tcc aat cca tgt tta aat ggc ggc agt tgc aag gat gac att     1117
Cys Glu Ser Asn Pro Cys Leu Asn Gly Gly Ser Cys Lys Asp Asp Ile
            100                 105                 110

aat tcc tat gaa tgt tgg tgt ccc ttt gga ttt gaa gga aag aac tgt     1165
Asn Ser Tyr Glu Cys Trp Cys Pro Phe Gly Phe Glu Gly Lys Asn Cys
        115                 120                 125

gaa tta gat gta aca tgt aac att aag aat ggc aga tgc gag cag ttt     1213
Glu Leu Asp Val Thr Cys Asn Ile Lys Asn Gly Arg Cys Glu Gln Phe
    130                 135                 140

tgt aaa aat agt gct gat aac aag gtg gtt tgc tcc tgt act gag gga     1261
Cys Lys Asn Ser Ala Asp Asn Lys Val Val Cys Ser Cys Thr Glu Gly
145                 150                 155                 160

tat cga ctt gca gaa aac cag aag tcc tgt gaa cca gca gtg cca ttt     1309
Tyr Arg Leu Ala Glu Asn Gln Lys Ser Cys Glu Pro Ala Val Pro Phe
                165                 170                 175

cca tgt gga aga gtt tct gtt tca caa act tct aag ctc acc cgt gct     1357
Pro Cys Gly Arg Val Ser Val Ser Gln Thr Ser Lys Leu Thr Arg Ala
            180                 185                 190

gag act gtt ttt cct gat gtg gac tat gta aat tct act gaa gct gaa     1405
Glu Thr Val Phe Pro Asp Val Asp Tyr Val Asn Ser Thr Glu Ala Glu
        195                 200                 205

acc att ttg gat aac atc act caa agc acc caa tca ttt aat gac ttc     1453
Thr Ile Leu Asp Asn Ile Thr Gln Ser Thr Gln Ser Phe Asn Asp Phe
    210                 215                 220

act cgg gtt gtt ggt gga gaa gat gcc aaa cca ggt caa ttc cct tgg     1501
```

-continued

```
Thr Arg Val Val Gly Gly Glu Asp Ala Lys Pro Gly Gln Phe Pro Trp
225                 230                 235                 240

cag gtt gtt ttg aat ggt aaa gtt gat gca ttc tgt gga ggc tct atc     1549
Gln Val Val Leu Asn Gly Lys Val Asp Ala Phe Cys Gly Gly Ser Ile
                245                 250                 255

gtt aat gaa aaa tgg att gta act gct gcc cac tgt gtt gaa act ggt     1597
Val Asn Glu Lys Trp Ile Val Thr Ala Ala His Cys Val Glu Thr Gly
            260                 265                 270

gtt aaa att aca gtt gtc gca ggt gaa cat aat att gag gag aca gaa     1645
Val Lys Ile Thr Val Val Ala Gly Glu His Asn Ile Glu Glu Thr Glu
        275                 280                 285

cat aca gag caa aag cga aat gtg att cga att att cct cac cac aac     1693
His Thr Glu Gln Lys Arg Asn Val Ile Arg Ile Ile Pro His His Asn
    290                 295                 300

tac aat gca gct att aat aag tac aac cat gac att gcc ctt ctg gaa     1741
Tyr Asn Ala Ala Ile Asn Lys Tyr Asn His Asp Ile Ala Leu Leu Glu
305                 310                 315                 320

ctg gac gaa ccc tta gtg cta aac agc tac gtt aca cct att tgc att     1789
Leu Asp Glu Pro Leu Val Leu Asn Ser Tyr Val Thr Pro Ile Cys Ile
                325                 330                 335

gct gac aag gaa tac acg aac atc ttc ctc aaa ttt gga tct ggc tat     1837
Ala Asp Lys Glu Tyr Thr Asn Ile Phe Leu Lys Phe Gly Ser Gly Tyr
            340                 345                 350

gta agt ggc tgg gga aga gtc ttc cac aaa ggg aga tca gct tta gtt     1885
Val Ser Gly Trp Gly Arg Val Phe His Lys Gly Arg Ser Ala Leu Val
        355                 360                 365

ctt cag tac ctt aga gtt cca ctt gtt gac cga gcc aca tgt ctt cga     1933
Leu Gln Tyr Leu Arg Val Pro Leu Val Asp Arg Ala Thr Cys Leu Arg
    370                 375                 380

tct aca aag ttc acc atc tat aac aac atg ttc tgt gct ggc ttc cat     1981
Ser Thr Lys Phe Thr Ile Tyr Asn Asn Met Phe Cys Ala Gly Phe His
385                 390                 395                 400

gaa gga ggt aga gat tca tgt caa gga gat agt ggg gga ccc cat gtt     2029
Glu Gly Gly Arg Asp Ser Cys Gln Gly Asp Ser Gly Gly Pro His Val
                405                 410                 415

act gaa gtg gaa ggg acc agt ttc tta act gga att att agc tgg ggt     2077
Thr Glu Val Glu Gly Thr Ser Phe Leu Thr Gly Ile Ile Ser Trp Gly
            420                 425                 430

gaa gag tgt gca atg aaa ggc aaa tat gga ata tat acc aag gta tcc     2125
Glu Glu Cys Ala Met Lys Gly Lys Tyr Gly Ile Tyr Thr Lys Val Ser
        435                 440                 445

cgg tat gtc aac tgg att aag gaa aaa aca aag ctc act taa             2167
Arg Tyr Val Asn Trp Ile Lys Glu Lys Thr Lys Leu Thr
    450                 455                 460

taatctagag ctcgctgatc agcctcgact gtgccttcta gttgccagcc atctgttgtt   2227

tgcccctccc ccgtgccttc cttgaccctg gaaggtgcca ctcccactgt cctttcctaa   2287

taaaatgagg aaattgcatc gcattgtctg agtaggtgtc attctattct ggggggtggg   2347

gtggggcagg acagcaaggg ggaggattgg gaagacaata gcaggcatgc tggggatgcg   2407

gtgggctcta tggcttctga ggcggaaaga accagctggg gctcgagcat gcaagcttcg   2467

agggggggcc cggtaccagc ttttgttccc tttagtgagg gttaatttcg agcttggcgt   2527

aatcatggtc atagctgttt cctgtgtgaa attgttatcc gctcacaatt ccacacaaca   2587

tacgagccgg aagcataaag tgtaaagcct ggggtgccta atgagtgagc taactcacat   2647

taattgcgtt gcgctcactg cccgctttcc agtcgggaaa cctgtcgtgc cagctgcatt   2707

aatgaatcgg ccaacgcgcg gggagaggcg gtttgcgtat tgggcgctct tccgcttcct   2767
```

-continued

```
cgctcactga ctcgctgcgc tcggtcgttc ggctgcggcg agcggtatca gctcactcaa   2827

aggcggtaat acggttatcc acagaatcag gggataacgc aggaaagaac atgtgagcaa   2887

aaggccagca aaaggccagg aaccgtaaaa aggccgcgtt gctggcgttt ttccataggc   2947

tccgcccccc tgacgagcat cacaaaaatc gacgctcaag tcagaggtgg cgaaacccga   3007

caggactata aagataccag gcgtttcccc ctggaagctc cctcgtgcgc tctcctgttc   3067

cgaccctgcc gcttaccgga tacctgtccg cctttctccc ttcgggaagc gtggcgcttt   3127

ctcatagctc acgctgtagg tatctcagtt cggtgtaggt cgttcgctcc aagctgggct   3187

gtgtgcacga accccccgtt cagcccgacc gctgcgcctt atccggtaac tatcgtcttg   3247

agtccaaccc ggtaagacac gacttatcgc cactggcagc agccactggt aacaggatta   3307

gcagagcgag gtatgtaggc ggtgctacag agttcttgaa gtggtggcct aactacggct   3367

acactagaag gacagtattt ggtatctgcg ctctgctgaa gccagttacc ttcggaaaaa   3427

gagttggtag ctcttgatcc ggcaaacaaa ccaccgctgg tagcggtggt ttttttgttt   3487

gcaagcagca gattacgcgc agaaaaaaag gatctcaaga agatcctttg atcttttcta   3547

cggggtctga cgctcagaag aactcgtcaa gaaggcgata gaaggcgatg cgctgcgaat   3607

cgggagcggc gataccgtaa agcacgagga agcggtcagc ccattcgccg ccaagctctt   3667

cagcaatatc acgggtagcc aacgctatgt cctgatagcg gtccgccaca cccagccggc   3727

cacagtcgat gaatccagaa aagcggccat tttccaccat gatattcggc aagcaggcat   3787

cgccatgcgt cacgacgaga tcctcgccgt cgggcatgcg cgccttgagc ctggcgaaca   3847

gttcggctgg cgcgagcccc tgatgctctt cgtccagatc atcctgatcg acaagaccgg   3907

cttccatccg agtacgtgct cgctcgatgc gatgtttcgc ttggtggtcg aatgggcagg   3967

tagccggatc aagcgtatgc agccgccgca ttgcatcagc catgatggat actttctcgg   4027

caggagcaag gtgagatgac aggagatcct gccccggcac ttcgcccaat agcagccagt   4087

cccttcccgc ttcagtgaca acgtcgagca cagctgcgca aggaacgccc gtcgtggcca   4147

gccacgatag ccgcgctgcc tcgtcctgca gttcattcag ggcaccggac aggtcggtct   4207

tgacaaaaag aaccgggcgc ccctgcgctg acagccggaa cacggcggca tcagagcagc   4267

cgattgtctg ttgtgcccag tcatagccga atagcctctc cacccaagcg gccggagaac   4327

ctgcgtgcaa tccatcttgt tcaatcatgc gaaacgatcc tcatcctgtc tcttgatcag   4387

atcttgatcc cctgcgccat cagatccttg gcggcaagaa agccatccag tttactttgc   4447

agggcttccc aaccttacca gagggcgaat tcgagcttgc atgcctgca              4496
```

```
<210> SEQ ID NO 6
<211> LENGTH: 461
<212> TYPE: PRT
<213> ORGANISM: artificial
<220> FEATURE:
<223> OTHER INFORMATION: Synthetic Construct

<400> SEQUENCE: 6

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60
```

```
Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 7
<211> LENGTH: 4276
```

-continued

```
<212> TYPE: DNA
<213> ORGANISM: artificial
<220> FEATURE:
<223> OTHER INFORMATION: Expression plasmid pFN1645 having codon
      optimized sequence encoding for human coagulation factor IX
      (786-2171).
<220> FEATURE:
<221> NAME/KEY: CDS
<222> LOCATION: (786)..(2171)
<223> OTHER INFORMATION: human coagulation factor IX

<400> SEQUENCE: 7

ggtcgttaca taacttacgg taaatggccc gcctggctga ccgcccaacg acccccgccc      60

attgacgtca ataatgacgt atgttcccat agtaacgcca atagggactt tccattgacg     120

tcaatgggtg gagtatttac ggtaaactgc ccacttggca gtacatcaag tgtatcatat     180

gccaagtacg ccccctattg acgtcaatga cggtaaatgg cccgcctggc attatgccca     240

gtacatgacc ttatgggact ttcctacttg gcagtacatc tacgtattag tcatcgctat     300

taccatgcat ggtgatgcgg ttttggcagt acatcaatgg gcgtggatag cggtttgact     360

cacggggatt tccaagtctc caccccattg acgtcaatgg gagtttgttt tggcaccaaa     420

atcaacggga ctttccaaaa tgtcgtaaca actccgcccc attgacgcaa atgggcggta     480

ggcgtgtacg gtgggaggtc tatataagca gagctcgttt agtgaaccgt cagatcgcct     540

ggagacgcca tccacgctgt tttgacctcc atagaagaca ccgggaccga tccagcctcc     600

gcggccggga acggtgcatt ggaacgcgga ttccccgtgt taattaacag gtaagtgtct     660

tcctcctgtt tccttcccct gctattctgc tcaaccttcc tatcagaaac tgcagtatct     720

gtatttttgc tagcagtaat actaacggtt cttttttct cttcacaggc cacactggat      780

ccacc atg cag agg gtg aac atg atc atg gca gaa tcc cca ggc ctc atc     830
      Met Gln Arg Val Asn Met Ile Met Ala Glu Ser Pro Gly Leu Ile
      1               5                   10                  15

acc atc tgc ctg ctg gga tat ctg ctc agt gct gaa tgt aca gtg ttt      878
Thr Ile Cys Leu Leu Gly Tyr Leu Leu Ser Ala Glu Cys Thr Val Phe
                20                  25                  30

ctg gat cat gaa aat gcc aac aaa att ctg aat cgg cca aag aga tat      926
Leu Asp His Glu Asn Ala Asn Lys Ile Leu Asn Arg Pro Lys Arg Tyr
            35                  40                  45

aat tct ggc aaa ctg gaa gag ttt gtg caa ggg aac ctg gag aga gaa      974
Asn Ser Gly Lys Leu Glu Glu Phe Val Gln Gly Asn Leu Glu Arg Glu
        50                  55                  60

tgt atg gaa gaa aag tgt agt ttt gaa gaa gca cgg gaa gtg ttt gaa     1022
Cys Met Glu Glu Lys Cys Ser Phe Glu Glu Ala Arg Glu Val Phe Glu
    65                  70                  75

aac act gaa aga aca act gaa ttt tgg aag cag tat gtg gat gga gat     1070
Asn Thr Glu Arg Thr Thr Glu Phe Trp Lys Gln Tyr Val Asp Gly Asp
80                  85                  90                  95

caa tgc gag tcc aat cca tgt ctg aat ggg ggc agt tgc aag gat gac     1118
Gln Cys Glu Ser Asn Pro Cys Leu Asn Gly Gly Ser Cys Lys Asp Asp
                100                 105                 110

att aat tcc tat gaa tgt tgg tgt ccc ttt gga ttt gaa gga aag aac     1166
Ile Asn Ser Tyr Glu Cys Trp Cys Pro Phe Gly Phe Glu Gly Lys Asn
            115                 120                 125

tgt gaa ctg gat gtg aca tgt aac att aag aat ggc aga tgt gag cag     1214
Cys Glu Leu Asp Val Thr Cys Asn Ile Lys Asn Gly Arg Cys Glu Gln
        130                 135                 140

ttt tgt aaa aat agt gct gat aac aag gtg gtg tgc tcc tgt act gag     1262
Phe Cys Lys Asn Ser Ala Asp Asn Lys Val Val Cys Ser Cys Thr Glu
    145                 150                 155
```

-continued

```
gga tat cgc ctg gca gaa aac cag aag tcc tgt gaa cca gca gtg cca      1310
Gly Tyr Arg Leu Ala Glu Asn Gln Lys Ser Cys Glu Pro Ala Val Pro
160                 165                 170                 175

ttt cca tgt gga aga gtg tct gtg tcc caa act tct aag ctc acc cgg      1358
Phe Pro Cys Gly Arg Val Ser Val Ser Gln Thr Ser Lys Leu Thr Arg
                180                 185                 190

gct gag gct gtg ttt cct gat gtg gac tat gtc aat tct act gaa gct      1406
Ala Glu Ala Val Phe Pro Asp Val Asp Tyr Val Asn Ser Thr Glu Ala
            195                 200                 205

gaa acc att ctg gat aac atc act caa agc acc caa tcc ttt aat gac      1454
Glu Thr Ile Leu Asp Asn Ile Thr Gln Ser Thr Gln Ser Phe Asn Asp
        210                 215                 220

ttc act cgg gtg gtg ggt gga gaa gat gcc aaa cca ggt caa ttc cca      1502
Phe Thr Arg Val Val Gly Gly Glu Asp Ala Lys Pro Gly Gln Phe Pro
    225                 230                 235

tgg caa gtg gtc ctg aat ggc aaa gtg gat gca ttc tgt gga ggc tct      1550
Trp Gln Val Val Leu Asn Gly Lys Val Asp Ala Phe Cys Gly Gly Ser
240                 245                 250                 255

atc gtc aat gaa aaa tgg att gtg act gct gcc cac tgt gtg gaa act      1598
Ile Val Asn Glu Lys Trp Ile Val Thr Ala Ala His Cys Val Glu Thr
                260                 265                 270

ggt gtc aaa att aca gtg gtg gca ggc gaa cat aat att gag gag aca      1646
Gly Val Lys Ile Thr Val Val Ala Gly Glu His Asn Ile Glu Glu Thr
            275                 280                 285

gaa cat aca gag caa aag cgg aat gtg att cgc att att cct cac cac      1694
Glu His Thr Glu Gln Lys Arg Asn Val Ile Arg Ile Ile Pro His His
        290                 295                 300

aac tac aat gca gct att aat aag tac aac cat gac att gcc ctg ctg      1742
Asn Tyr Asn Ala Ala Ile Asn Lys Tyr Asn His Asp Ile Ala Leu Leu
    305                 310                 315

gaa ctg gat gaa ccc ctg gtg ctg aac agc tat gtg aca cct att tgc      1790
Glu Leu Asp Glu Pro Leu Val Leu Asn Ser Tyr Val Thr Pro Ile Cys
320                 325                 330                 335

att gct gac aag gaa tac acc aac atc ttc ctc aaa ttt gga tct ggc      1838
Ile Ala Asp Lys Glu Tyr Thr Asn Ile Phe Leu Lys Phe Gly Ser Gly
                340                 345                 350

tat gtc agc ggc tgg gga aga gtc ttc cac aaa ggg aga tct gct ctg      1886
Tyr Val Ser Gly Trp Gly Arg Val Phe His Lys Gly Arg Ser Ala Leu
            355                 360                 365

gtc ctg cag tac ctg aga gtg cca ctg gtg gac cgg gcc aca tgt ctc      1934
Val Leu Gln Tyr Leu Arg Val Pro Leu Val Asp Arg Ala Thr Cys Leu
        370                 375                 380

cgc tct aca aag ttc acc atc tat aac aac atg ttc tgt gct gga ttc      1982
Arg Ser Thr Lys Phe Thr Ile Tyr Asn Asn Met Phe Cys Ala Gly Phe
    385                 390                 395

cat gaa gga ggt aga gat tcc tgt caa gga gat agt ggg gga ccc cat      2030
His Glu Gly Gly Arg Asp Ser Cys Gln Gly Asp Ser Gly Gly Pro His
400                 405                 410                 415

gtc act gaa gtg gaa ggg acc agt ttc ctg act gga att att agc tgg      2078
Val Thr Glu Val Glu Gly Thr Ser Phe Leu Thr Gly Ile Ile Ser Trp
                420                 425                 430

ggt gaa gag tgt gca atg aaa ggc aaa tat gga atc tat acc aag gtg      2126
Gly Glu Glu Cys Ala Met Lys Gly Lys Tyr Gly Ile Tyr Thr Lys Val
            435                 440                 445

tcc cgc tat gtc aac tgg att aag gaa aaa aca aag ctc act taa          2171
Ser Arg Tyr Val Asn Trp Ile Lys Glu Lys Thr Lys Leu Thr
        450                 455                 460

tgactctaga aaagccgaat tctgcaggaa ttgggtggca tccctgtgac cctccccag     2231

tgcctctcct ggccctggaa gttgccactc cagtgcccac cagccttgtc ctaataaaat    2291
```

-continued

```
taagttgcat cattttgtct gactaggtgt ccttctataa tattatgggg tggagggggg   2351
tggtatggag caaggggcaa gttgggaaga caacctgtag ggctcgaggg ggggcccggt   2411
accagctttt gttcccttta gtgagggtta atttcgagct tggtcttccg cttcctcgct   2471
cactgactcg ctgcgctcgg tcgttcggct gcggcgagcg gtatcagctc actcaaaggc   2531
ggtaatacgg ttatccacag aatcagggga taacgcagga aagaacatgt gagcaaaagg   2591
ccagcaaaag gccaggaacc gtaaaaaggc cgcgttgctg gcgtttttcc ataggctccg   2651
cccccctgac gagcatcaca aaaatcgacg ctcaagtcag aggtggcgaa acccgacagg   2711
actataaaga taccaggcgt ttccccctgg aagctccctc gtgcgctctc ctgttccgac   2771
cctgccgctt accggatacc tgtccgcctt tctcccttcg ggaagcgtgg cgctttctca   2831
tagctcacgc tgtaggtatc tcagttcggt gtaggtcgtt cgctccaagc tgggctgtgt   2891
gcacgaaccc cccgttcagc ccgaccgctg cgccttatcc ggtaactatc gtcttgagtc   2951
caacccggta agacacgact tatcgccact ggcagcagcc actggtaaca ggattagcag   3011
agcgaggtat gtaggcggtg ctacagagtt cttgaagtgg tggcctaact acggctacac   3071
tagaaggaca gtatttggta tctgcgctct gctgaagcca gttaccttcg gaaaaagagt   3131
tggtagctct tgatccggca aacaaaccac cgctggtagc ggtggttttt ttgtttgcaa   3191
gcagcagatt acgcgcagaa aaaaaggatc tcaagaagat cctttgatct tttctacggg   3251
gtctgacgct cagaagaact cgtcaagaag gcgatagaag gcgatgcgct gcgaatcggg   3311
agcggcgata ccgtaaagca cgaggaagcg gtcagcccat tcgccgccaa gctcttcagc   3371
aatatcacgg gtagccaacg ctatgtcctg atagcggtcc gccacaccca gccggccaca   3431
gtcgatgaat ccagaaaagc ggccattttc caccatgata ttcggcaagc aggcatcgcc   3491
atgcgtcacg acgagatcct cgccgtcggg catgcgcgcc ttgagcctgg cgaacagttc   3551
ggctggcgcg agcccctgat gctcttcgtc cagatcatcc tgatcgacaa gaccggcttc   3611
catccgagta cgtgctcgct cgatgcgatg tttcgcttgg tggtcgaatg ggcaggtagc   3671
cggatcaagc gtatgcagcc gccgcattgc atcagccatg atggatactt tctcggcagg   3731
agcaaggtga gatgacagga gatcctgccc cggcacttcg cccaatagca gccagtccct   3791
tcccgcttca gtgacaacgt cgagcacagc tgcgcaagga acgcccgtcg tggccagcca   3851
cgatagccgc gctgcctcgt cctgcagttc attcagggca ccggacaggt cggtcttgac   3911
aaaaagaacc gggcgcccct gcgctgacag ccggaacacg gcggcatcag agcagccgat   3971
tgtctgttgt gcccagtcat agccgaatag cctctccacc caagcggccg gagaacctgc   4031
gtgcaatcca tcttgttcaa tcatgcgaaa cgatcctcat cctgtctctt gatcagatct   4091
tgatcccctg cgccatcaga tccttggcgg caagaaagcc atccagttta ctttgcaggg   4151
cttcccaacc ttaccagagg gcgccccagc tggcaattcc ggttcgcttg ctgtccataa   4211
aaccgcccag tctagcaact gttgggaagg gcggggctgc aggaattcga gcttgcatgc   4271
ctgca                                                                4276
```

<210> SEQ ID NO 8
<211> LENGTH: 461
<212> TYPE: PRT
<213> ORGANISM: artificial
<220> FEATURE:
<223> OTHER INFORMATION: Synthetic Construct

<400> SEQUENCE: 8

-continued

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
```

-continued

```
        420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460
```

NUCLEIC ACID FORMULATIONS FOR GENE DELIVERY AND METHODS OF USE

CROSS REFERENCE TO RELATED APPLICATIONS

This application is a divisional of, and claims priority to, U.S. application Ser. No. 10/234,406 filed Sep. 3, 2002, now U.S. Pat. No. 7,173,116 which was the U.S. National Application of and a Continuation of International Patent Application No. PCT/US01/06953, filed Mar. 2, 2001 which claims priority to U.S. Provisional Application Ser. No. 60/187,236 filed Mar. 3, 2000 and U.S. Provisional Application Ser. No. 60/261,751 filed Jan. 16, 2001, which are all hereby incorporated by reference, including any drawings, as if fully set forth herein.

FIELD OF THE INVENTION

This invention relates to novel compositions and methods for the introduction of a nucleic acid molecule into a cell, including by a pulse voltage delivery method, for the expression of a protein, peptide, antisense RNA, ribozyme, or polypeptide.

BACKGROUND OF THE INVENTION

The following information is presented solely to assist the understanding of the reader. None of the information is admitted to describe prior art to the claims of the present invention.

Gene therapy is a major area of research in drug development. Gene therapy has been considered a desirable mechanism to correct genetically determined diseases resulting from the failure to produce certain proteins and acquired diseases such as autoimmunity and cancer. One example of a class of genetically determined diseases that are considered amenable to gene therapy is hemophilia. Hemophilia B, for example, is a bleeding disorder that results from the absence of functional blood clotting Factor IX ("F.IX"). The disease state is classified as severe, moderate or mild, depending on the level of functional F.IX. (Lusher, J. M. (1999) *Thromb Haemost* 82:572-5751). Approximately 5,200 males are afflicted with the disease in the U.S. with approximately 45% of these cases being of the severe type. In severe cases of hemophilia B (<1% of normal F.IX levels) there are frequent bleeding events that can be life threatening and often produce debilitating destruction of the patient's joints. The current therapy for hemophilia B is the administration of F.IX protein in response to bleeding events only. The use of either blood derived or recombinant F.IX has shown that tremendous clinical and quality of life benefits can be achieved by converting the most severe hemophilia B cases into the moderate or mild range. In some countries F.IX protein is given prophylactically in the most severe cases, despite the fact that these treatments are extremely expensive (Ljung, R. C. (1999) *Thromb Haemost* 82:525-530). The prophylactic use of F.IX is not frequent in the U.S.

Gene therapy could provide a new prophylactic approach for the treatment of diseases such as hemophilia B. A technological barrier to commercialization of gene therapy, however, is the need for practical, effective and safe gene delivery methods. In animal models of hemophilia, viral-based vectors have been used successfully to administer the human F.IX gene either to liver or muscle. (Kay, M. A., et al. (1993) *Science* 262:117-119; Herzog, R. W., et al. (1999) *Nat Med:* 56-63; Snyder, R. O., et al. (1999) *Nat Med* 5:64-70; Chao, H., et al. (1999) *Gene Ther* 6:1695-1704; Lozier, J. N., et al. (1999) *Blood* 94:3968-3975; Kaufman, R. J. (1999) *Hum Gene Ther* 10:2091-2107). In some cases, these approaches have led to long-term (>2 years) expression of therapeutic levels of F.IX in a canine model of hemophilia B (Herzog, R. W., et al. (1999) *Nat Med* 5:56-63). However, the limitations of viral-based approaches have been extensively reported. For instance, re-administration is not possible with these vectors because of the humoral immune response generated against the viral proteins. In addition to manufacturing challenges to obtain adequate reproducible vector supply, there are also significant safety concerns associated with viral vectors, particularly for those targeting the liver for gene expression. Not withstanding the problems associated with viral gene therapy, viruses have been considered by many to be more efficient than non-viral delivery vehicles.

A problem of non-viral gene therapy is to achieve the delivery and expression of sufficient nucleic acid to result in a tangible, physiologically relevant expression. Although DNA plasmids in isotonic saline (so-called 'naked' DNA) were shown several years ago to transfect a variety of cells in vivo, the lack of stability of such unprotected plasmids to enzymatic degradation is associated with irreproducibility in uptake leading to highly variable expression and biological responses in animal models. The very low bioavailability of 'naked' plasmid in most tissues also requires high doses of plasmids to be administered to generate a pharmacological response.

The field of non-viral gene delivery has therefore been directed to the development of more efficient synthetic delivery systems able to increase the efficiency of plasmid delivery, confer prolonged expression and provide for storage stable formulations as is expected of other pharmaceutical formulations.

To overcome the problem of degradation of nucleic acids, typically plasmid DNA ("pDNA"), and enhance the efficiency of gene transfection, cationic condensing agents (such as polybrene, dendrimers, chitosan, lipids, and peptides) have been developed to protect pDNA by condensing it through electrostatic interaction. (A. P. Rolland, From genes to gene medicines: recent advances in nonviral gene delivery, review in *Therapeutic drug carrier systems,* 15(2):143-198 (1998).) However, the use of condensed plasmid particles for transfection of a large number of muscle cells in vivo has not been successful as compared directly to "naked" DNA. Wolff, J. A., et al., *J. Cell Sci.,* 103, 1249, 1992. In particular, due to the physiology of the muscle, the use of rigid condensed particles containing plasmid for efficient transfection of a larger number of muscle cells has not been successful to date because cationic lipid and polylysine plasmid complexes do not cross the external lamina to gain access to the caveolae and T tubules. Id.

Additional strategies that include the modulation of the plasmid surface charge and hydrophobicity by interaction with protective, interactive non-condensing systems (e.g., PINC™ polymers) have shown advantages over the use of 'naked' DNA for direct administration to solid tissues. [WO9621470, U.S. Pat. No. 6,040,295, incorporated herein by reference.]

Biodegradable microspheres have also been used in gene delivery that encapsulate the nucleic acid. For example, WO0078357, Chen, W. et al, disclosed matrices, films, gels and hydrogels which include hyaluronic acid (HA) derivatized with a dihydrazide and crosslinked to a nucleic acid forming slow release microspheres. WO9524929, Boekelheide, K. et al., disclosed encapsulation of genes in a matrix preferably in the form of a microparticle such as a microsphere, microcapsule, a film, an implant, or a coating on a device such as a stent. U.S. Pat. No. 6,048,551, Beer, S. et al. disclosed a controlled release gene delivery system utilizing poly (lactide-co-glycolide) (PLGA), hydroxypropylmethyl cellulose phthalate, cellulose acetate phthalate, and the Ludragit R, L, and E series of polymers and copolymer microspheres to encapsulate the gene vector. Luo D et al. Pharm Res 1999 Aug. 16(8):1300-8, reported the characterization of systems for controlled delivery of DNA from implantable polymer matrices (EVAc: poly (ethylene-co-vinyl acetate)) and injectable microspheres (PLGA and PLA: poly (D, L-lactide-co-glycolide) copolymer and poly (L-lactide), respectively). Despite their promise, microspheres can pose manufacturing difficulties and can adversely constrain the release of DNA in vivo, particularly in muscle tissue.

Thus, despite these recent advances, there remains a need for additional and improved formulated nucleic acid compositions and methods of administering the same for gene therapy.

SUMMARY OF THE INVENTION

An alternative approach to the use of viral vectors is the use of non-viral plasmid-based gene therapy. The present invention discloses novel compositions and methods for enhancing the administration of nucleic acids and uptake thereof by an organism. In one embodiment, the formulation utilizes anionic polymers such as poly-amino acids, polynucleotides, or poly-acrylic acids that are able to enhance the transfection of nucleic acids to muscle tissues with and without electroporation. In one embodiment of the invention, the poly-amino acid is poly-glutamic acid and salt thereof. The poly-glutamic acid formulation has been shown in the present invention to be particularly useful in increasing electroporation assisted transfection in vivo.

The compositions of the present invention that are used to administer nucleic acid, preferably by pulse voltage delivery, allows for treatment of diseases, vaccination, and treatment of muscle disorders and serum protein deficiencies.

Another aspect of the present invention provides a method for treating a mammalian condition or disease. The method involves the step of administering to a mammal suffering from the condition or disease a therapeutically effective amount of a composition of the invention. In one embodiment of the invention, the disease is characterized by insufficient levels of active Factor IX. Delivery of a nucleic acid encoding Factor IX formulated in poly-glutamate and delivered in conjunction with electroporation according to the present invention is able to provide nanogram levels of Factor IX in the peripheral blood of large animals.

In one embodiment of the invention, the disease is characterized by insufficient levels of red blood cells resulting in anemia. Delivery of a nucleic acid encoding erythropoietin ("EPO") formulated in poly-L-glutamate and delivered in conjunction with electroporation according to the present invention is able to provide sufficient levels of EPO to result in a maximal hematocrit level.

In one embodiment of the invention, the disease is characterized by disregulation of the immune system. Delivery of a nucleic acid encoding a cytokine, such as in one example, human interferon alpha 2b ("hINFα"), formulated in poly-L-glutamine and delivered in conjunction with electroporation according to the present invention is able to provide nanogram levels of hINFα in the peripheral circulation.

In yet another aspect, the invention also features a method for delivering a nucleic acid molecule to a mammal, more preferably a human, by utilizing a non-condensing anionic polyamino acid formulation. The method involves the step of providing a composition of the invention to the cells of the organism by use of a device configured and arranged to cause pulse voltage delivery of the composition.

In preferred embodiments the device for delivering is an electroporation device that delivers the composition of the invention to the cell by pulse voltage and/or delivers the composition of the invention by subjecting the cells to an electric field.

The present invention also features a kit. The kit includes a container for providing a composition of the invention and either (i) a pulse voltage device for delivering the composition of the invention to cells of an organism, wherein the pulse voltage device is capable of being combined with the container, or (ii) instructions explaining how to deliver the composition of the invention with the pulse voltage device. Thus the "container" can include instructions furnished to allow one of ordinary skill in the art to make compositions of the invention. The instructions will furnish steps to make the compounds used for formulating nucleic acid molecules. Additionally, the instructions will include methods for testing compositions of the invention that entail establishing if the nucleic acid molecules are damaged upon injection after electroporation. The kit may also include notification of an FDA approved use and instructions.

A method for making a kit of the invention is also provided. The method involves the steps of combining a container for providing a composition of the invention with either (i) a pulse voltage device for delivering the composition of the invention to the cells of an organism, wherein the pulse voltage device is capable of being combined with the container, or (ii) instructions explaining how to deliver the composition of the invention with the pulse voltage device.

The invention also provides a method of treating a mammal suffering from cancer or an infectious disease. The method involves the step of providing a composition of the invention to cells of the mammal by use of a device configured and arranged to provide pulse voltage delivery of a composition of the invention to cells of the mammal, wherein the molecule encodes a cancer antigen or an antigen for the infectious disease.

As noted above, the compositions of the present invention that are used to administer nucleic acid, preferably by pulse voltage delivery, include a compound that protects the nucleic acid and/or prolongs the localized bioavailability of the nucleic acid and/or enhances expression when administered to an organism in vivo, or in vitro in cell culture.

As the compositions are useful for delivery of a nucleic acid molecule to cells in vivo, in a related aspect the invention provides a composition at an in vivo site of administration. In particular, this includes compositions for delivering a nucleic acid molecule at an in vivo site in a mammal.

The summary of the invention described above is not limiting and other and further objects, features and advantages of the invention will be apparent from the following detailed description of the presently preferred embodiments of the invention and from the claims.

Figure 3:
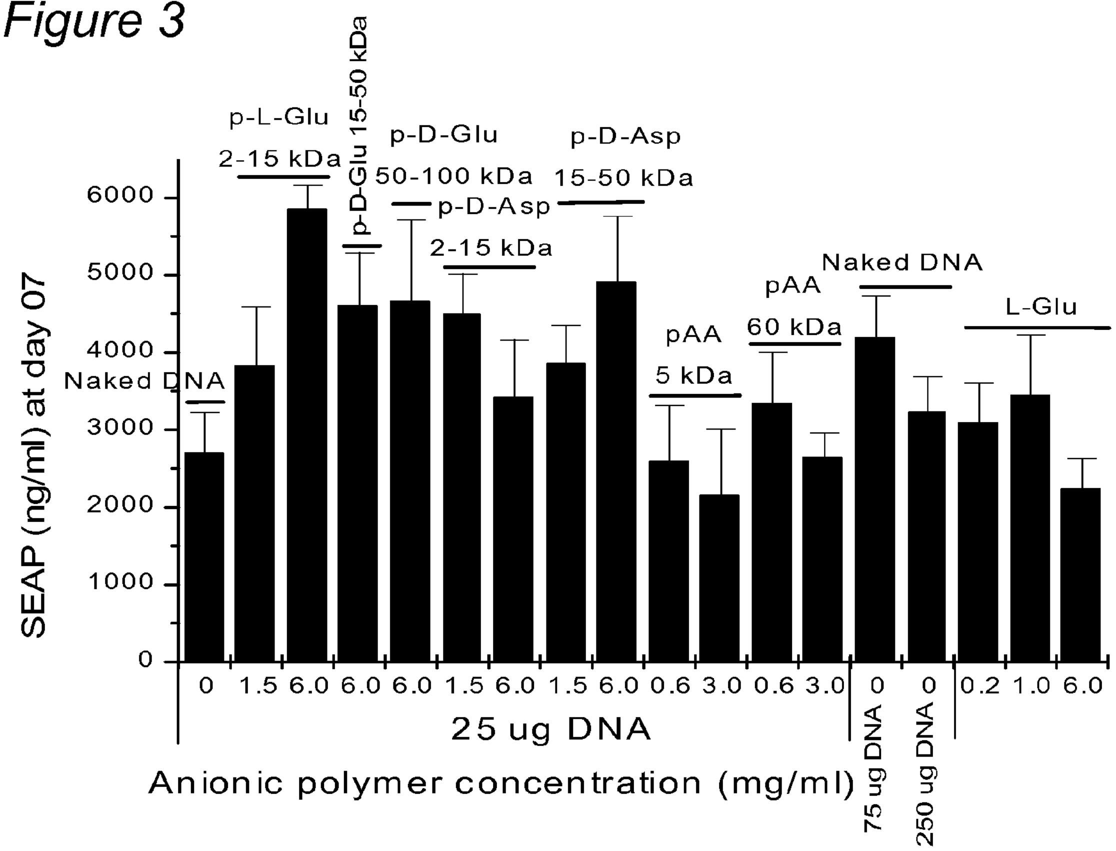

FIG. 3 shows SEAP serum concentrations at day 7 post injection of naked SEAP pDNA or SEAP pDNA/anionic polymer mixtures in the tibialis cranialis muscle of CD-1 mice with electroporation and the amount of SEAP pDNA administered per animal was regularly (unless mentioned) 25 micrograms in 50 microliters (half this dose per leg).

Figure 4:
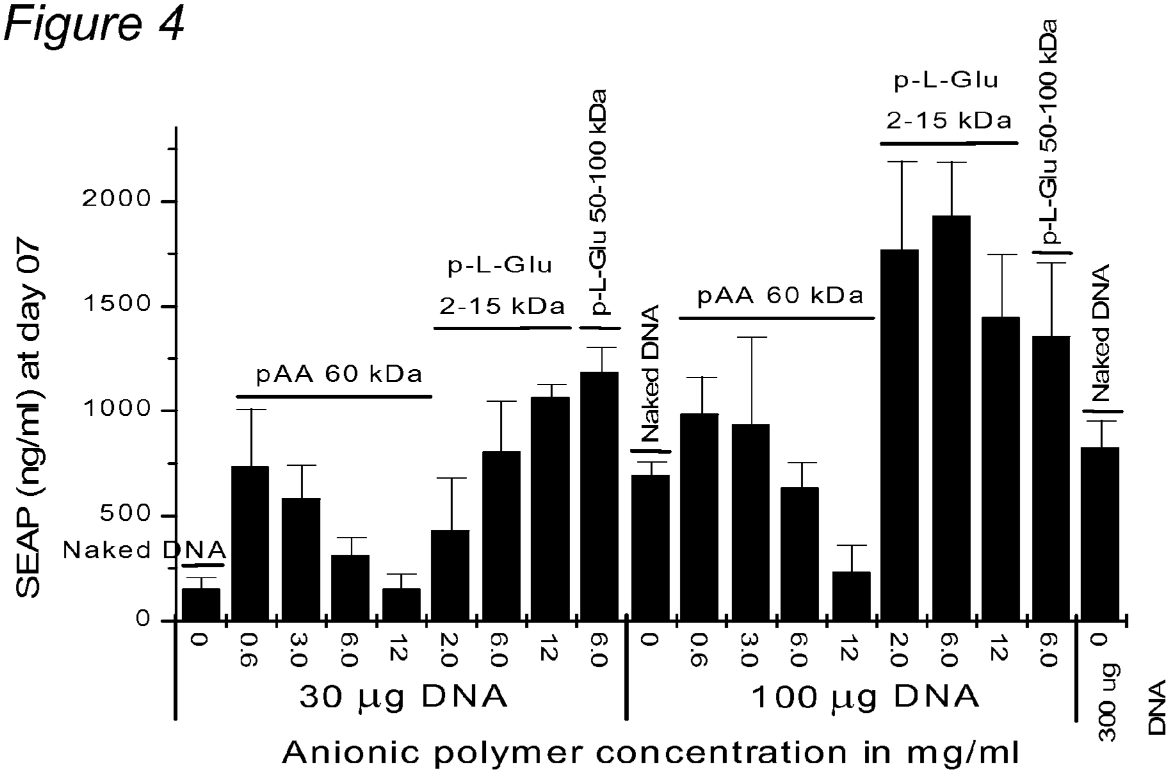

FIG. 4 shows SEAP serum concentrations at day 7 post injection of naked SEAP pDNA or SEAP pDNA/anionic polymer mixtures in the gastrocnemius muscle of CD-1 mice and electroporation of the tissue. The concentration of the anionic polymer in the injected solution varied as indicated on the graph.

FIG. 5 shows SEAP serum concentrations at day 7 as a function of the amount of SEAP pDNA injected in different formulations as indicated: A in the tibialis cranialis muscle of CD-1 mice; B in the gastrocnemius muscle of CD-1 mice comparing either naked SEAP pDNA or a mixture of SEAP pDNA and a poly-L-glutamic acid at 6.0 mg/ml.

Figure 6:
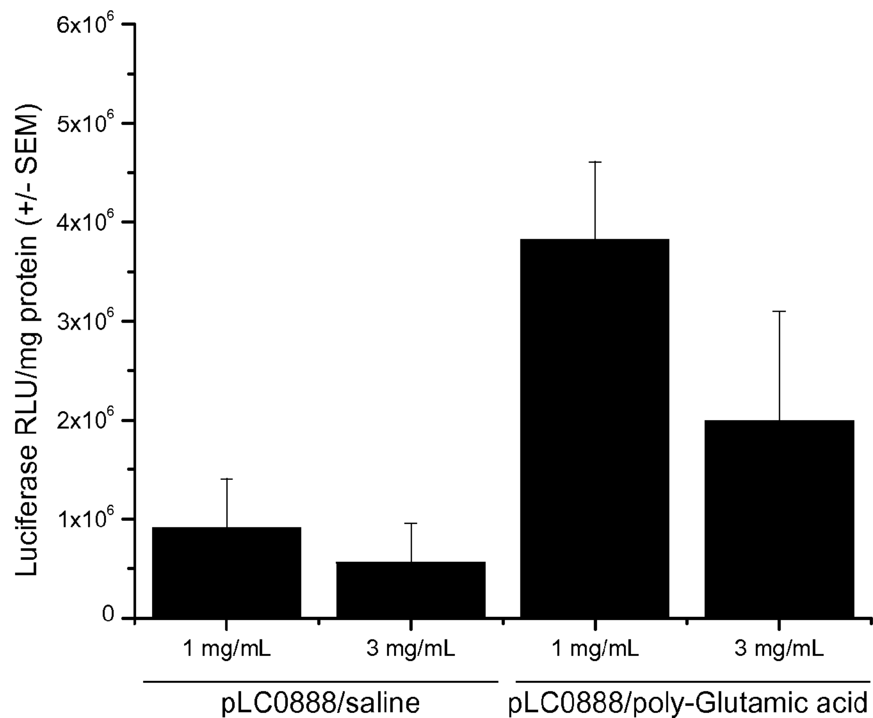

FIG. 6 shows luciferase expression after direct intramyocardial injection of plasmid DNA formulated in saline versus poly-glutamic acid.

Figure 7:
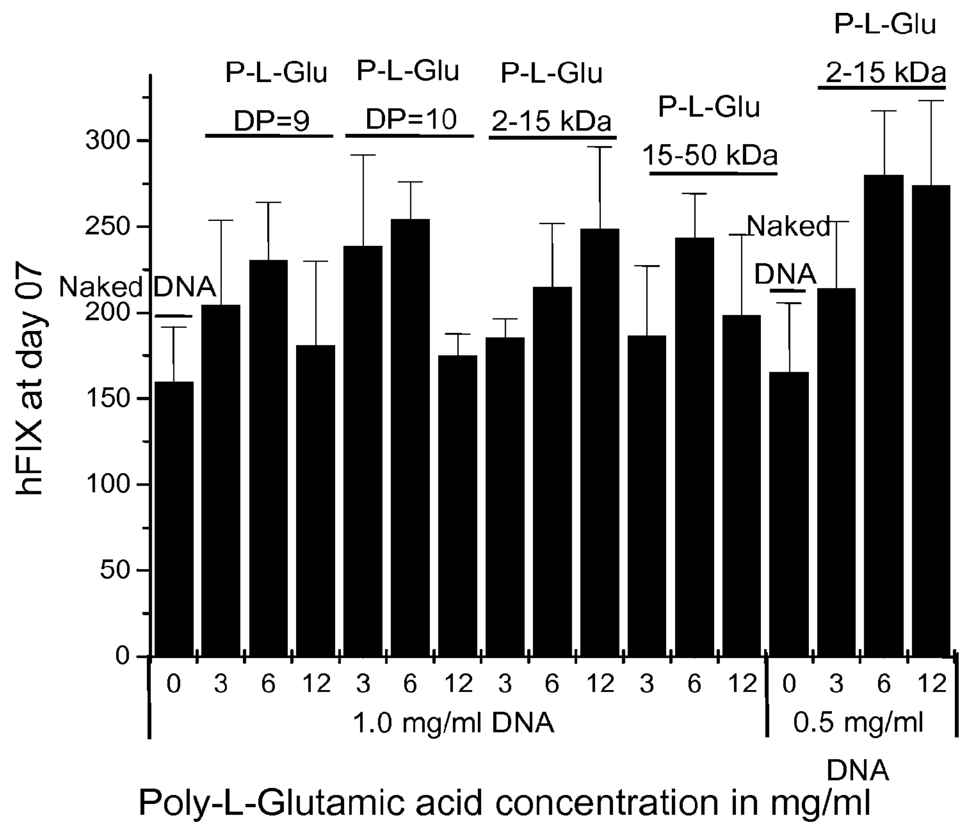

FIG. 7 shows hF.IX serum concentrations at day 7 post injection of naked hF.IX pDNA or hF.IX pDNA/poly-L-glutamic acid mixtures in the tibialis muscle of C57BL/6 mice and electroporation of the tissue. The concentration of the anionic polymer in the injected solution varied as indicated on the graph.

Figure 8:
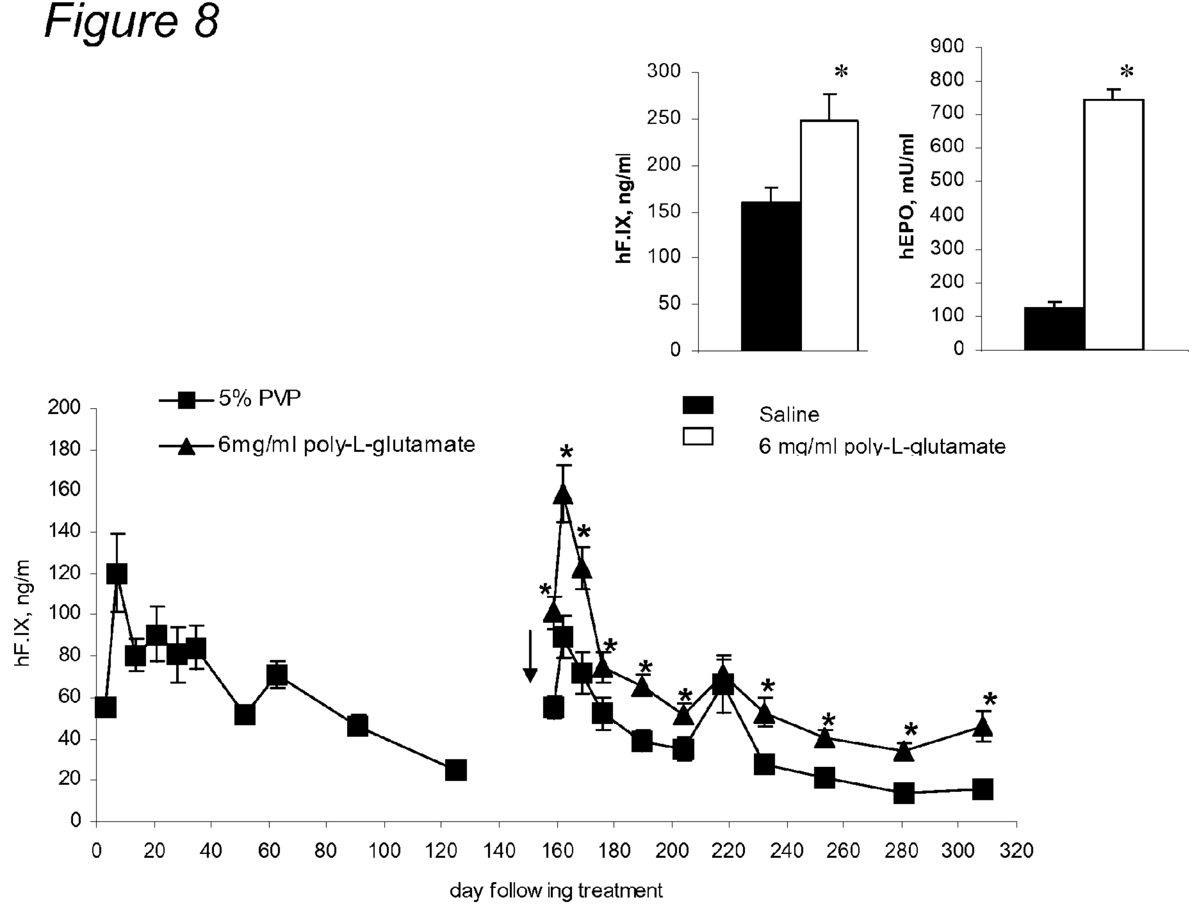

FIG. 8 shows hF.IX expression in plasma of immune deficient (SCID beige) mice.

Figure 9:
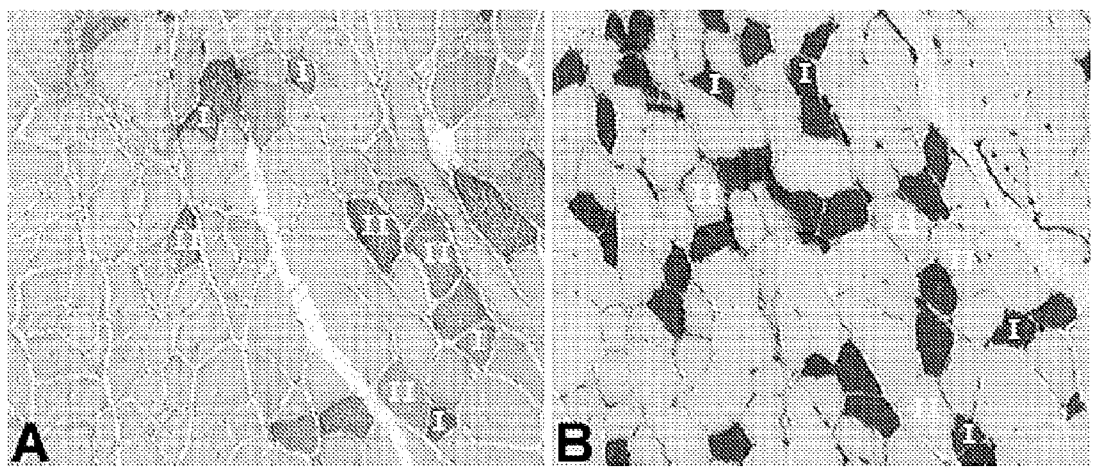

FIG. 9 depicts the immunohistology and fiber-type of hF.IX expressing myocytes in SCID mouse muscle.

Figure 10A:
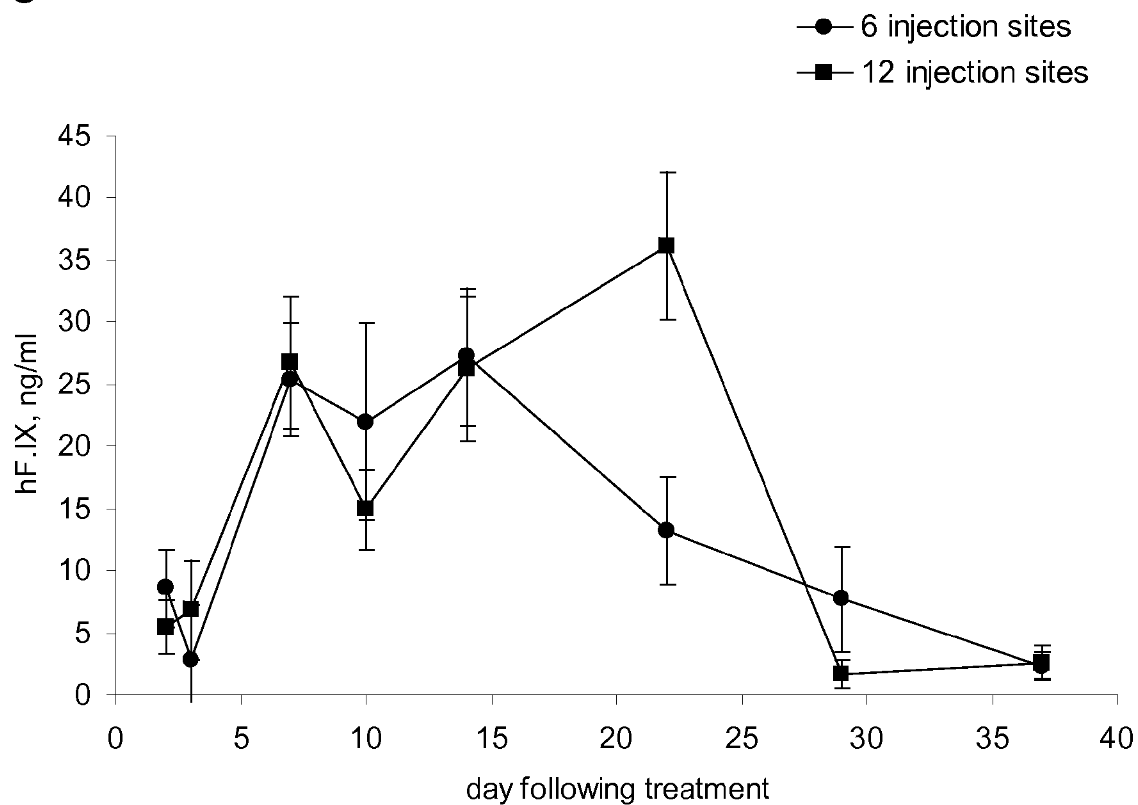
Figure 10B:
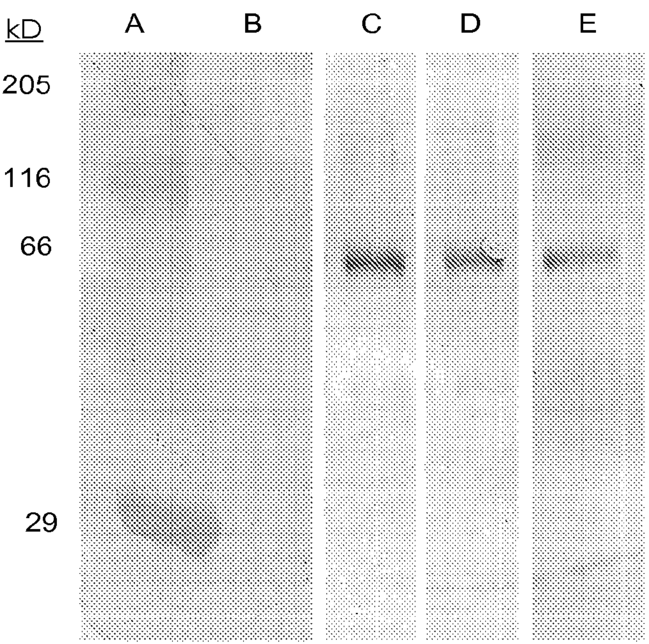

FIG. 10 A depicts plasma hF.IX levels determined by ELISA in dogs following intramuscular injection of plasmid augmented by electroporation at different numbers of sites. Values are means±SEM with n=3 for each group. FIG. 10B shows a western blot of purified hF.IX using treated animal serum as the primary antibody. Lane A, molecular marker; lane B, negative control serum; lane C, positive control (canine serum spiked with rabbit anti-hF.IX antibodies; lane D, serum from a female dog from the 6 injection group (peak expression hF.IX 35.71 ng/ml); lane E, serum from a male dog from the 12 injection group (peak hF.IX expression 47.9 ng/ml).

Figure 11:
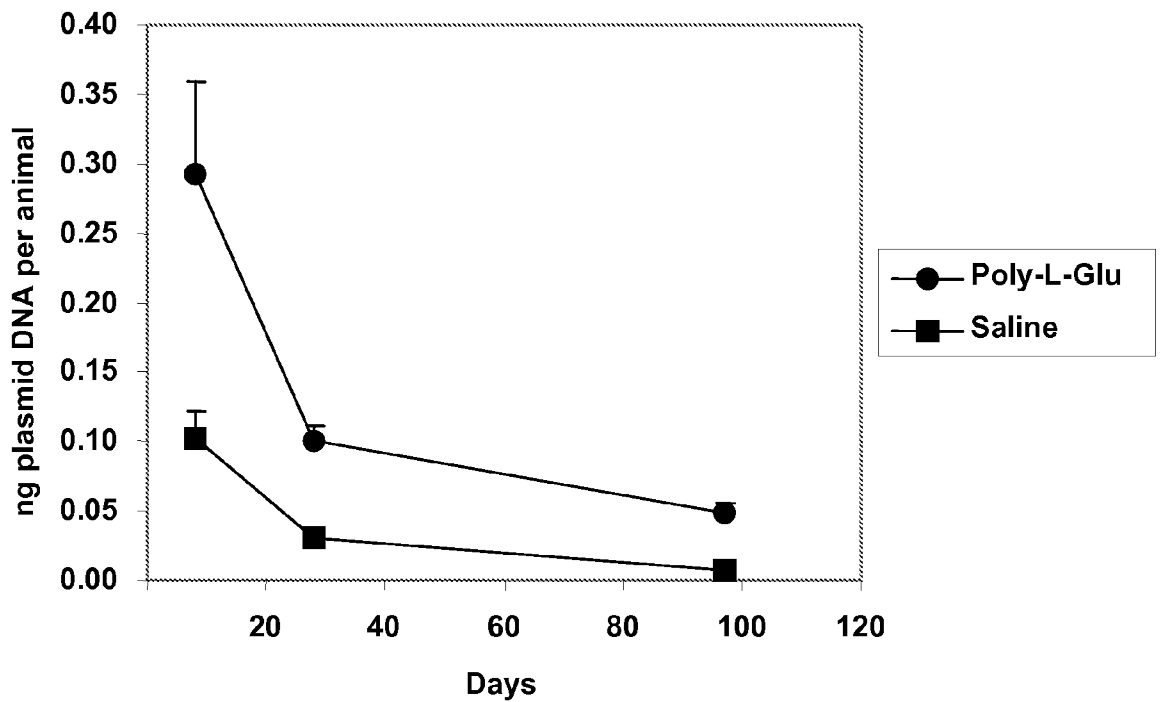

FIG. 11 depicts the duration of retention of the mouse EPO plasmid DNA following delivery by electroporation using saline and poly-L-glutamic acid formulations.

Figure 12:
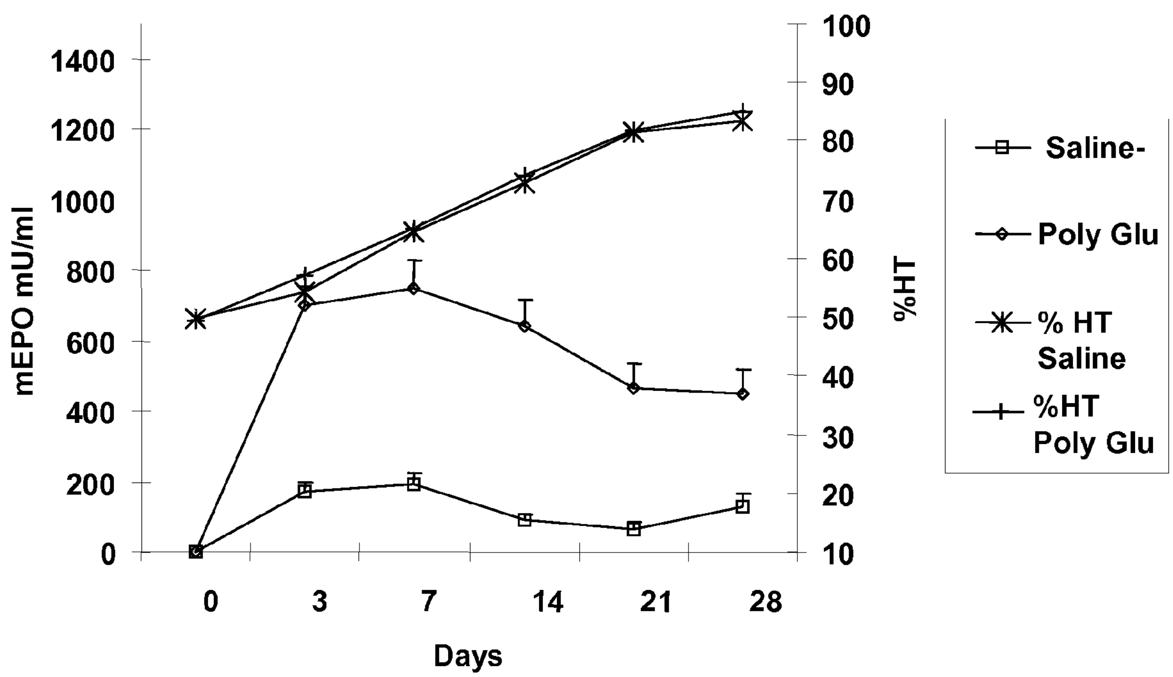

FIG. 12 depicts EPO expression and hematocrit in mice following delivery of the mouse EPO gene by electroporation using saline and poly-L-glutamic acid formulations.

Figure 13:
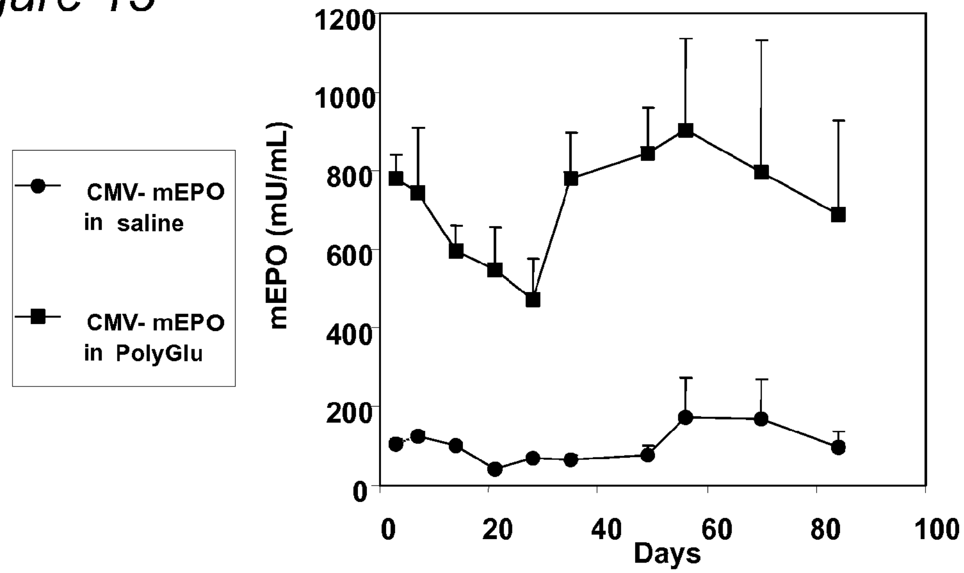

FIG. 13 depicts the results of the EPO expression in mice following delivery of the mouse EPO gene by electroporation using saline and poly-L-glutamic acid formulations over a three month time frame.

Figure 14A:
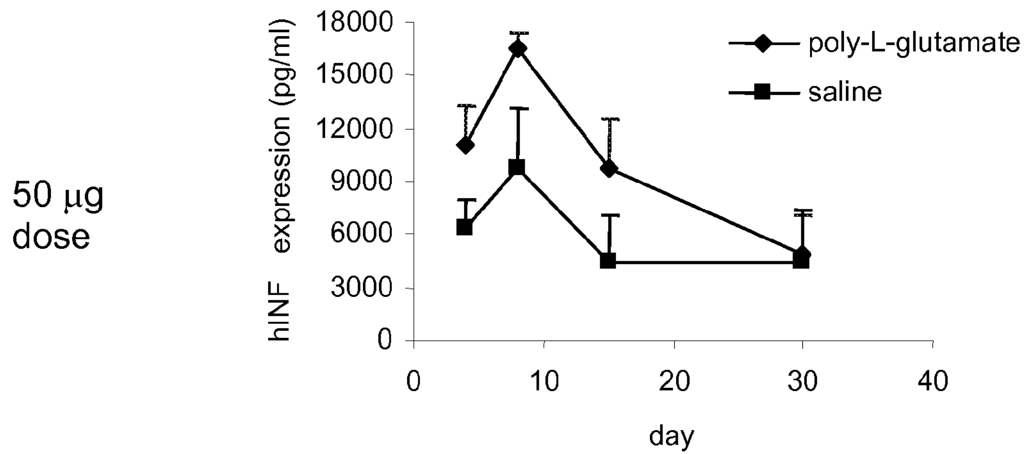
Figure 14B:
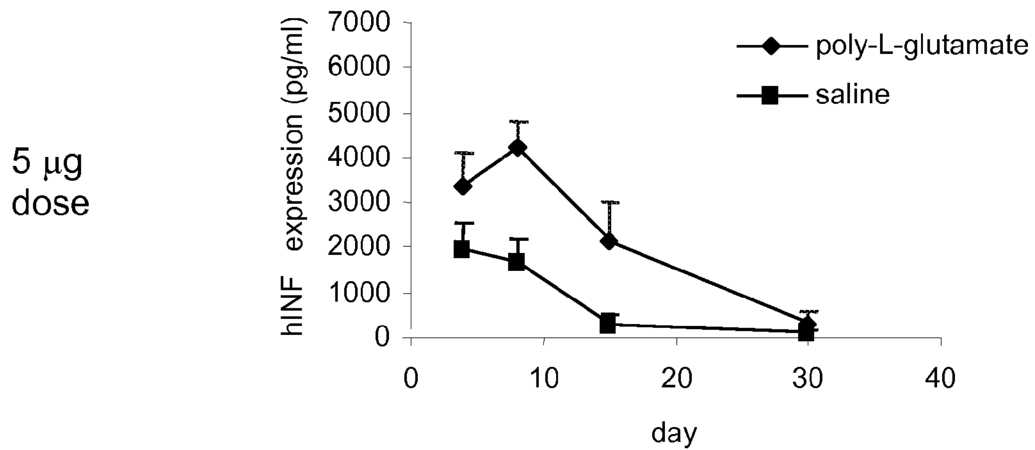

FIG. 14 depicts a comparison of hINFα gene expression after delivery in saline versus polyglutamate. A depicts the results using a 50 microgram dose of plasmid DNA while B depicts the results of administration of a 5 microgram dose of plasmid DNA.

Figure 15:
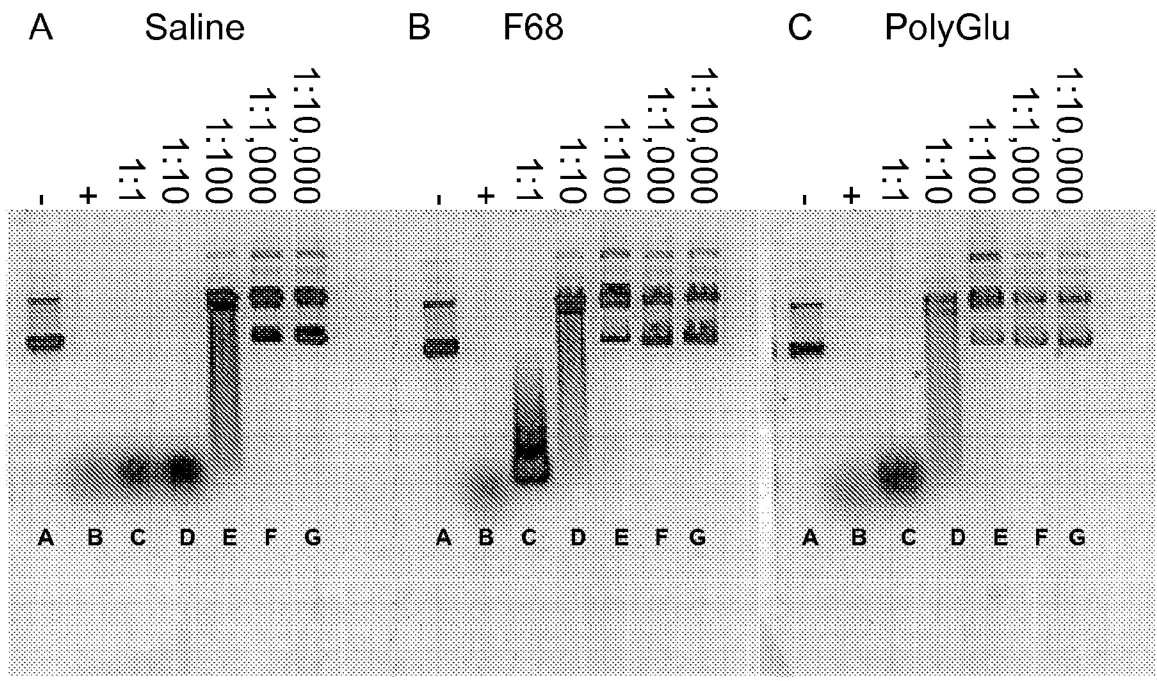

FIG. 15 shows the ability of poly-L-glutamate and poloxamer formulations to protect DNA from nuclease degradation. Panel A represents a DNA in saline formulation; Panel B represents DNA formulated in 5% Pluronic F68; Panel C represents DNA formulated in 6 mg/ml poly-L-glutamate. Lane A, negative control of plasmid DNA without DNase; lane B, positive control of plasmid DNA and DNase mixed 1:1; lane C, DNase diluted 1:1; lane D, DNase diluted 1:10; lane E, DNase diluted 1:100; lane F, DNase diluted 1:1,000; lane G, DNase diluted 1:10,000.

Figure 16:
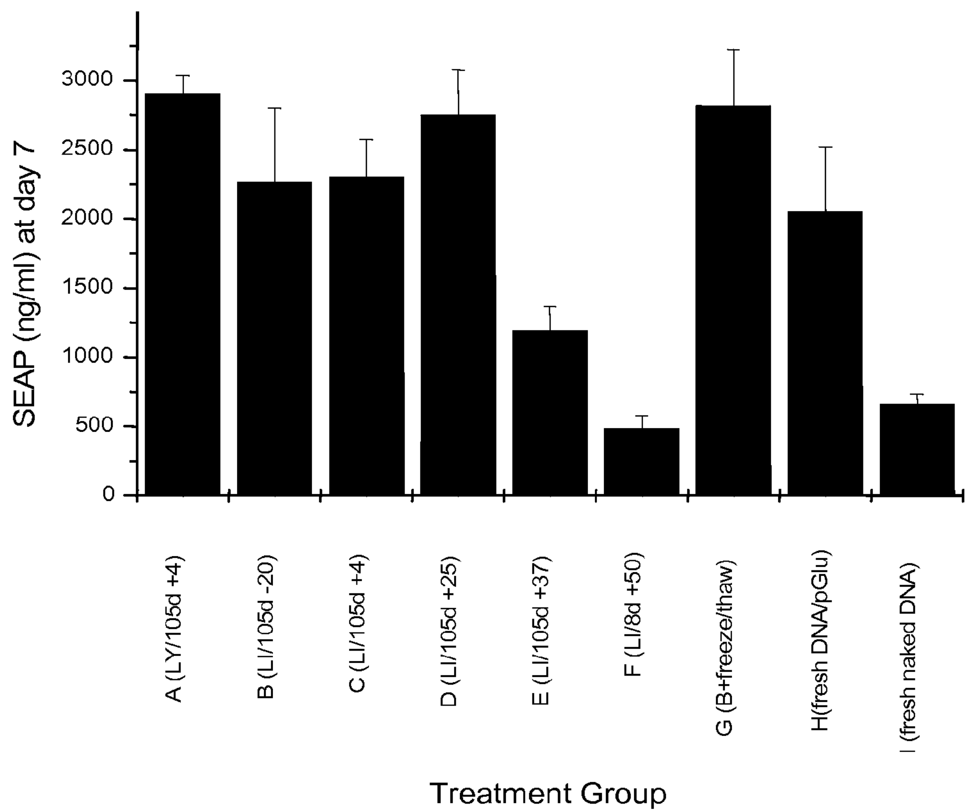

FIG. 16 depicts the results of long term biological stability of plasmid DNA encoding SEAP formulated in 6 mg/ml poly-L-glutamate under different storage conditions. A, lyophilization and storage at 4° C. for 105 days; B, freezing of a liquid formulation with storage at −20° C. for 105 days; C, liquid storage at 4° C. for 105 days; D, liquid storage at room temperature for 105 days; E, liquid storage at 37° C. for 105 days; F, liquid storage at 50° C. for 8 days; G, liquid formulation subject to freeze/thawing; H, fresh DNA formulated on poly-L-glutamate; I, fresh DNA without poly-L-glutamate.

Figure 17:
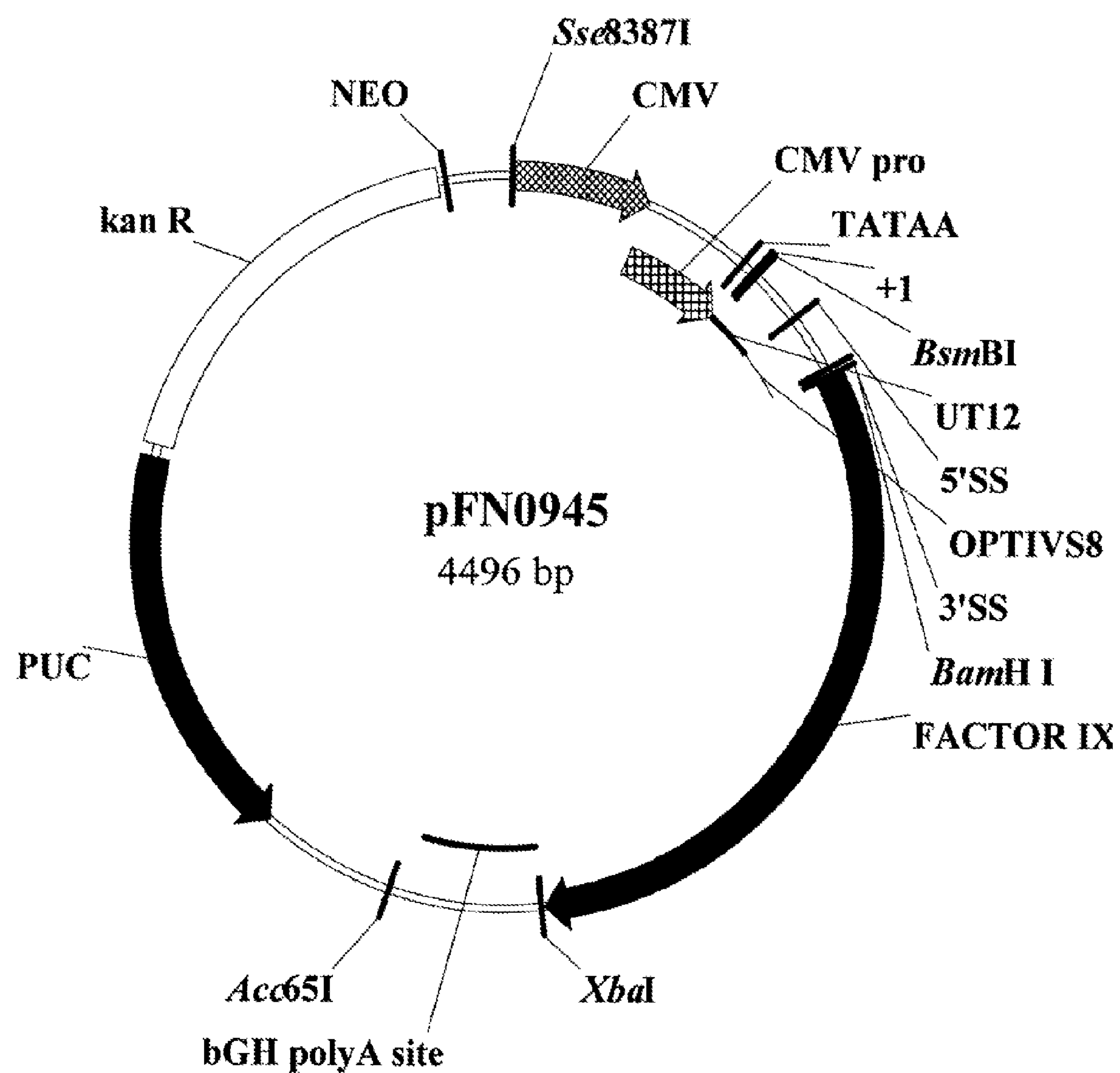

FIG. 17 depicts the plasmid map for pFN0945, an expression plasmid carrying the gene for hF.IX. The sequence of the complete plasmid is disclosed as SEQ. ID. NO. 3.

Figure 18:
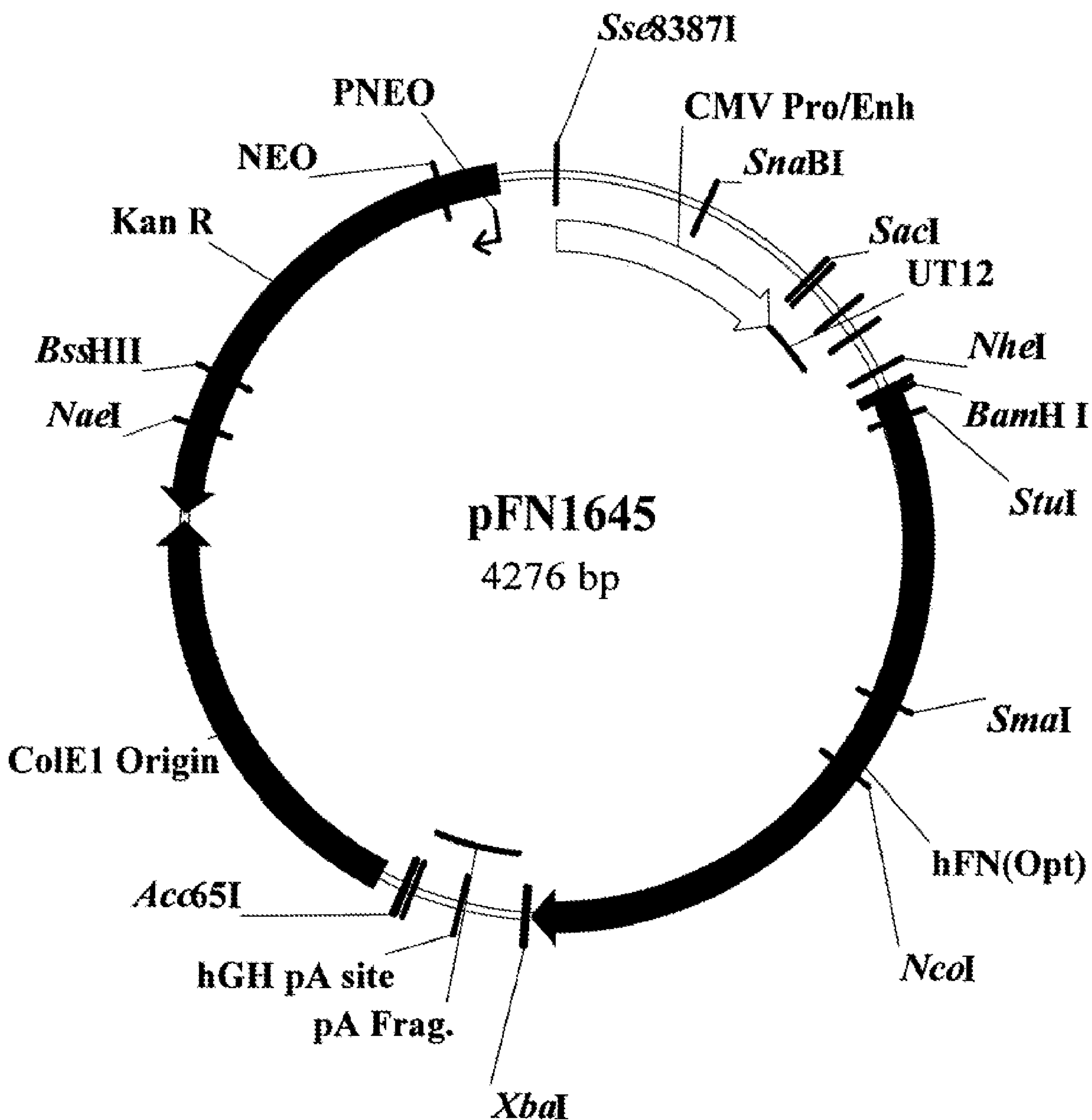

FIG. 18 depicts the plasmid map for pFN1645, an expression plasmid carrying an codon optimized gene for hF.IX. The sequence of the complete plasmid is disclosed as SEQ. ID. NO. 4.

Figure 19:
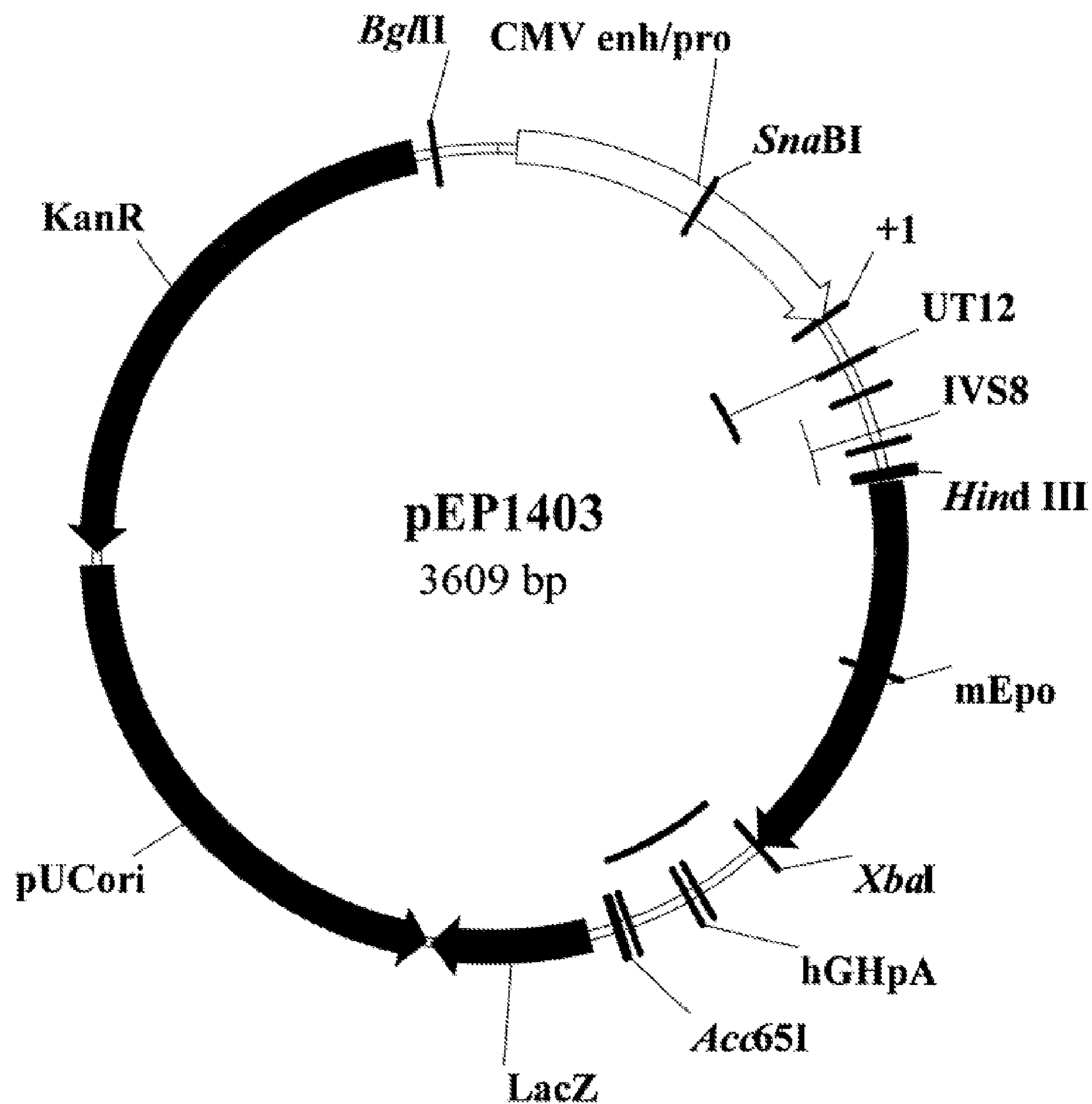

FIG. 19 depicts the plasmid map for pEP1403, an expression plasmid carrying the mouse erythropoietin gene. The sequence of the complete plasmid is disclosed as SEQ. ID. NO. 2.

Figure 20:
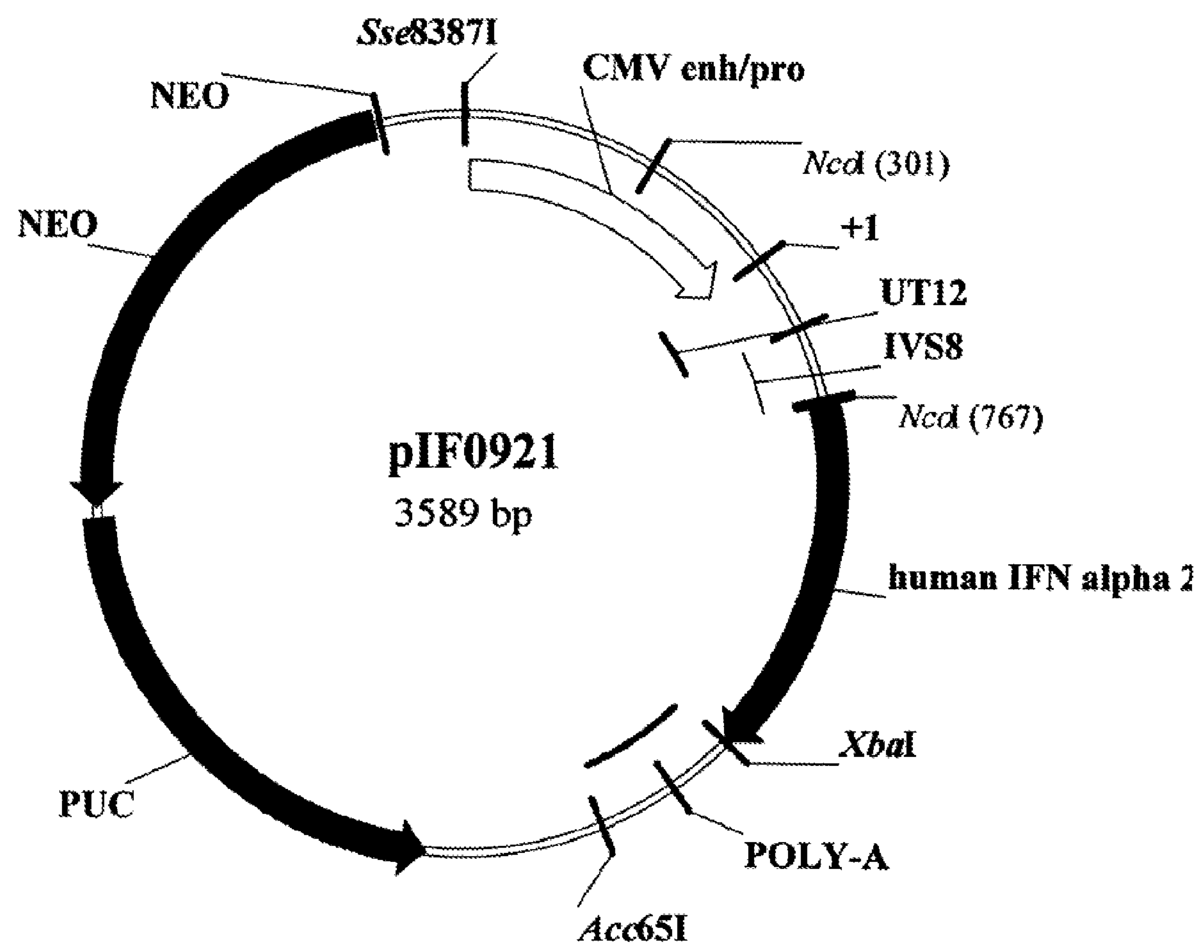

FIG. 20 depicts the plasmid map for pIF0921, an expression plasmid carrying the human interferon alpha gene. The sequence of the complete plasmid is disclosed as SEQ. ID. NO. 1.

DETAILED DESCRIPTION OF THE PREFERRED EMBODIMENTS

The delivery and expression of sequences encoded on a vector in eukaryotic cells, particularly in vivo in a mammal, depends on a variety of factors including transfection efficiency and lifetime of the coding sequence within the transfected cell. Thus, a number of methods are reported for accomplishing such delivery.

A non-viral gene medicine is composed of three major elements: i) a nucleic acid encoding a gene product (e.g., a therapeutic protein), ii) a plasmid-based expression system, and iii) a synthetic gene delivery system. These products are intended to have low toxicity due to the use of synthetic components for gene delivery (minimizing for instance the risks of immunogenicity generally associated with viral vectors) and non-integrating plasmids for gene expression. Since no integration of plasmid sequences into host chromosomes has been reported in vivo to date, they should neither activate oncogenes nor inactivate tumor suppressor genes. This built-in safety with non-viral systems contrasts with the risks associated with the use of most viral vectors. As episomal systems residing outside the chromosomes, plasmids have defined pharmacokinetics and elimination profiles, leading to a finite duration of gene expression in target tissues.

Formulating the nucleic acid with anionic polymers as disclosed below is particularly desirable because they enhance transfection and expression of the nucleic acid, protect the nucleic acid from degradation, and are completely biodegradable. In addition, because formulating the nucleic acid with anionic polymers results in more efficient transfection, lower amounts of DNA may be used. By biodegradable, it is meant that the anionic polymers can be metabolized or cleared by the organism in vivo without any or minimal toxic effects or side effects. The term "anionic polymers" means polymers having a repeating subunit which includes, for example, an ionized carboxyl, phosphate or sulfate group having a net negative charge at neutral pH. Examples of the anionic polymers include poly-amino acids (such as polyglutamic acid, poly-aspartic acid and combinations thereof), poly nucleic acids, poly acrylic acid, poly galacturonic acid, and poly vinyl sulfate. In the case of polymeric acids, the polymer will typically be utilized as the salt form.

Efforts have been made to enhance the delivery of plasmid DNA to cells by physical means including electroporation, sonoporation and pressure. Injection by electroporation is a modern technique that involves the application of a pulsed electric field to create transient pores in the cellular membrane without causing permanent damage to the cell and thereby allows for the introduction of exogenous molecules. This technique has been used widely in research laboratories to create hybridomas and is now being applied to gene transfer approaches for therapy. By adjusting the electrical pulse generated by an electroporetic system, nucleic acid molecules can find their way through passageways or pores in the cell that are created during the procedure. U.S. Pat. No. 5,704,908 describes an electroporation apparatus for delivering molecules to cells at a selected location within a cavity in the body of a patient. (U.S. Pat. No. 5,704,908, including any drawings contained therein, is hereby incorporated by reference as if fully set forth herein.)

The use of electroporetic methods to deliver genes suspended in saline into rabbit and porcine arteries as models to treat coronary and peripheral vascular disease has been discussed at the 3rd US-Japan Symposium on Drug Delivery (D. B. Dev, J. J. Giordano and D. L. Brown, Maui, Hawaii, Dec. 17-22, 1995). The ability to target and express the lacZ reporter gene suspended in saline to various depths of the dermis region in hairless mice has been described in the article "Depth-Targeted Efficient Gene delivery and Expression in the skin by Pulsed Electric Fields: An approach to Gene Therapy of Skin Aging and Other Diseases" (Zhang et al., Biochemical and Biophysical Research Communications 220, 633-636 (1996)). A mammalian expression plasmid for the lacZ gene in saline has been injected into the internal carotid artery of rats whose brain tumors had been electroporated between two electrodes. The gene was reported to be expressed in the tumor cells three days after plasmid injection and furthermore, lacZ activity was reported to be isolated only to the tissues and cells targeted (Nishi, et al., Cancer Research 56, 1050-1055, Mar. 1, 1996).

Formulations for electroporation are described in U.S. patent application Ser. No. 09/322,602, which is incorporated herein by reference in its entirety, including any drawings. By adjusting the electrical pulse generated by an electroporetic system, nucleic acid molecules can find their way in the cell through passageways or pores that are created during the procedure.

Previously, treatment of hemophilia B by non-viral methods was not been possible because only low and variable levels of gene expression were achieved. Recently, the use of electroporation in vivo was shown to produce consistent high levels of gene expression in muscle, liver, skin, solid tumors and testis following direct injection of plasmid into these tissues (Titomirov, A. V., et al. (1991) *Biochim Biophys Acta* 1088: 131-134; Muramatsu, T., et al. (1997) *Biochem Biophys Res Commun* 233: 45-49; Suzuki, T., et al. (1998) *FEBS Lett* 425: 436-440; Aihara, H. and Miyazaki, J. (1998) *Nat Biotechnol* 16: 867-870; Mir, L. M., et al. (1998) *C R Acad Sci III* 321: 893-899; Rizzuto, G., et al. (1999) *Proc Natl Acad Sci USA* 96: 6417-6422; Goto, T., et al (2000) *Proc Natl Acad Sci U S A* 97:354-359; Somiari, S., et al. (2000) *Mol Ther* 2:178-187). In mice, electroporation of plasmid DNA in saline was used to achieve circulating levels of hF.IX that were 2% of normal and maintained for at least 2 months (Bettan, M., et al. (2000) *Mol Ther* 2:204-210). The present application discloses novel plasmid formulations for electroporation that achieve four goals: (1) therapeutically significant levels of proteins in vivo, (2) persistent expression of the transgene, (3) re-administration of formulated plasmid to obtain levels comparable to the initial levels and (4) therapeutically significant levels in large animals.

The delivery of a formulated DNA according to the present invention by the use of pulse voltage delivery device represents a novel approach to gene delivery. In particular, the the preferred embodiment employing anionic amino acid polymers or poly-amino acids were able to substantially increase the expression of introduced genes by electroporation when compared with saline. The poly-amino acids also have the advantage over prior formulations by being completely biodegradable. The preferred embodiment also provides the advantage of allowing the uptake of formulated nucleic acid molecules (i.e., nucleic acid molecules in the compositions of the invention) by specifically targeted cells and cell lines, as well as uptake by multiple cell lines as desired. Injecting formulated nucleic acid molecules by pulse voltage delivery methods results in the formulated nucleic acid molecules gaining access to the cellular interior more directly through the destabilization of the cell wall and/or by the formation of pores as a result of the electroporetic process. Furthermore, in certain instances multiple cell lines can be targeted, thus allowing contact to many more cell types than in conventional needle injection. Thus, the present invention provides an enhanced delivery of nucleic acid molecules and also provides a more efficient gene delivery system which may be used to generate an immune response, express a therapeutic gene, modulate aspects of the cell cycle or cell physiology, or provide a method to achieve other gene delivery related therapeutic methods such as anti-tumor therapy.

The term "poly-L-glutamic acid" is used interchangeably herein with "poly-L-glutamic acid, sodium salt", "sodium poly-L-glutamate" and "poly-L-glutamate." "Poly-L-glutamate" refers to the sodium salt of poly-L-glutamic acid. Although the L stereoisomer of polyglutamic acid was found to be particularly useful, the other stereoisomer or racemic mixtures of isomers are within the scope of the invention. The present invention contemplates that other salts of anionic amino acid polymers may be equally suitable.

The term "anionic amino acid polymers" means polymeric forms of a given anionic amino acid such as, for example, poly-glutamic acid or poly-aspartic acid. The present invention contemplates that polymers formed of a mixture of anionic amino acids, such as for example glutamic acid and aspartic acid, may be equally suitable.

By "delivery" or "delivering" is meant transportation of nucleic acid molecules to desired cells or any cells. The nucleic acid molecules may be delivered to multiple cell lines, including the desired target. Delivery results in the nucleic acid molecules coming in contact with the cell surface, cell membrane, cell endosome, within the cell membrane, nucleus or within the nucleus, or any other desired area of the cell from which transfection can occur within a variety of cell lines which can include but are not limited to; tumor cells, epithelial cells, Langerhan cells, Langhans' cells, littoral cells, keratinocytes, dendritic cells, macrophage cells, Kupffer cells, muscle cells, lymphocytes and lymph nodes. Preferably, the composition of the invention is delivered to the cells by electroporation and the nucleic acid molecule component is not significantly sheared upon delivery, nor is cell viability directly effected by the pulse voltage delivery process.

By "nucleic acid" is meant both RNA and DNA including: cDNA, genomic DNA, plasmid DNA or condensed nucleic acid, nucleic acid formulated with cationic lipids, nucleic acid formulated with peptides, cationic polymers, RNA or mRNA. In a preferred embodiment, the nucleic acid administered is a plasmid DNA which constitutes a "vector". The nucleic acid can be, but is not limited to, a plasmid DNA vector with a eukaryotic promoter which expresses a protein with potential therapeutic action, such as, for example; hGH, VEGF, EPO, IGF-I, TPO, Factor IX, IFN-α, IFN-β, IL-2, IL-12, or the like.

As used herein, the term a "plasmid" refers to a construct made up of genetic material (i.e., nucleic acids). It includes genetic elements arranged such that an inserted coding sequence can be transcribed in eukaryotic cells. Also, while the plasmid may include a sequence from a viral nucleic acid, such viral sequence preferably does not cause the incorporation of the plasmid into a viral particle, and the plasmid is therefore a non-viral vector. Preferably, a plasmid is a closed circular DNA molecule. The enhancer/promoter region of an expression plasmid will determine the levels of expression. Most of the gene expression systems designed for high levels of expression contain the intact human cytomegalovirus (CMV) immediate early enhancer/promoter sequence. However, down-regulation of the CMV promoter over time has been reported in tissues. The hypermethylation of the CMV promoter, as observed when incorporated into retroviral vectors, has not been observed for episomal plasmids in vivo. Nevertheless, the CMV promoter silencing could be linked to its sensitivity to reduced levels of the transcription factor NF-κB. The activity of the CMV promoter has also been shown to be attenuated by various cytokines including interferons (α and β), and tumor necrosis factor (TNF-α). In order to prolong expression in vivo and ensure specificity of expression in desired tissues, tissue-specific enhancer/promoters have been incorporated in expression plasmids. The chicken skeletal alpha actin promoter has been shown to provide high levels of expression (equivalent to the ones achieved with a CMV-driven construct) for several weeks in non-avian striated muscles.

Additional genetic sequences in the expression plasmids can be added to influence the stability of the messenger RNA (mRNA) and the efficiency of translation. The 5' untranslated region (5' UTR) is known to effect translation and it is located between the cap site and the initiation codon. The 5' UTR should ideally be relatively short, devoid of strong secondary structure and upstream initiation codons, and should have an initiation codon AUG within an optimal local context. The 5' UTR can also influence RNA stability, RNA processing and transcription. In order to maximize gene expression by ensuring effective and accurate RNA splicing, one or more introns can be included in the expression plasmids at specific locations. The possibility of inefficient and/or inaccurate splicing can be minimized by using synthetic introns that have idealized splice junction and branch point sequences that match the consensus sequence. Another important sequence within a gene expression system is the 3' untranslated region (3' UTR), a sequence in the mRNA that extends from the stop codon to the poly(A) addition site. The 3' UTR can influence mRNA stability, translation and intracellular localization. The skeletal muscle α-actin 3' UTR has been shown to stabilize mRNA in muscle tissues thus leading to higher levels of expression as compared to other 3' UTR. This 3' UTR appears to induce a different intracellular compartmentalization of the produced proteins, preventing the effective trafficking of the proteins to the secretory pathway and favoring their perinuclear localization.

One of the attractive features of plasmid expression systems is the possibility to express multiple genes from a single construct. These multivalent systems may find applications in the expression of heterodimeric proteins, such as antibodies, or in the in vivo production of multiple antigens to generate a potent immune response for genetic vaccination. In cancer immunotherapy, the co-expression of co-stimulatory molecules with a variety of cytokines may also lead to enhanced responses.

The term "vector" as used herein refers to a construction including genetic material designed to direct transformation of a targeted cell. A vector contains multiple genetic material, preferably contiguous fragments of DNA or RNA, positionally and sequentially oriented with other necessary elements such that the nucleic acid can be transcribed and when necessary translated in the transfected cells. The "vector" preferably is a nucleic acid molecule incorporating sequences encoding therapeutic product(s) as well as, various regulatory elements for transcription, translation, transcript stability, replication, and other functions as are known in the art. The vector preferably allows for production of a product encoded for by a nucleic acid sequence contained in the vector. For example, expression of a particular growth factor protein encoded by a particular gene. A "DNA vector" is a vector whose native form is a DNA molecule. A "viral vector" is a vector whose native form is as the genomic material of a viral particle.

The term "transfection" as used herein refers to the process of introducing DNA (e.g., formulated DNA expression vector) into a cell, thereby, allowing cellular transformation. Following entry into the cell, the transfected DNA may: (1) recombine with that of the host; (2) replicate independently as a plasmid or temperate phage; or (3) be maintained as an episome without replication prior to elimination.

As used herein, "transformation" relates to transient or permanent changes in the characteristics (expressed phenotype) of a cell induced by the uptake of a vector by that cell. Genetic material is introduced into a cell in a form where it expresses a specific gene product or alters the expression or effect of endogenous gene products. Transformation of the cell may be associated with production of a variety of gene products including protein and RNA. These products may function as intracellular or extracellular structural elements, ligands, hormones, neurotransmitters, growth regulating factors, enzymes, chemotaxins, serum proteins, receptors, carriers for small molecular weight compounds, drugs, immunomodulators, oncogenes, cytokines, tumor suppressors, toxins, tumor antigens, antigens, antisense inhibitors, triple strand forming inhibitors, ribozymes, or as a ligand recognizing specific structural determinants on cellular structures for the purpose of modifying their activity. This list is only an example and is not meant to be limiting.

A "gene product" means products encoded by the vector. Examples of gene products include mRNA templates for translation, ribozymes, antisense RNA, proteins, glycoproteins, lipoproteins, phosphoproteins and polypeptides. The nucleic acid sequence encoding the gene product may be associated with a targeting ligand to effect targeted delivery.

"Uptake" means the translocation of the vector from the extracellular to intracellular compartments. This can involve receptor-mediated processes, fusion with cell membranes, endocytosis, potocytosis, pinocytosis or other translocation mechanisms. The vector may be taken up by itself or as part of a complex.

Administration as used herein refers to the route of introducing the compositions of the invention into the body of cells or organisms. Administration includes the use of electroporetic methods as provided by a pulse voltage device to targeted areas of the mammalian body such as the muscle cells and the lymphatic cells in regions such as the lymph nodes. Administration also includes intradermal, intra-tumoral and subcutaneous administration.

A "therapeutically effective amount" of a composition is an amount that is sufficient to cause at least temporary relief or improvement in a symptom or indication of a disease or condition. Thus, the amount is also sufficient to cause a pharmacological effect. The amount of the composition need not cause permanent improvement or improvement of all symptoms or indications.

The term "pulse voltage device", or "pulse voltage injection device" as used herein relates to an apparatus that is capable of causing or causes uptake of nucleic acid molecules into the cells of an organism by emitting a localized pulse of electricity to the cells, thereby causing the cell membrane to destabilize and result in the formation of passageways or pores in the cell membrane. It is understood that conventional devices of this type are calibrated to allow one of ordinary skill in the art to select and/or adjust the desired voltage amplitude and/or the duration of pulsed voltage and therefore it is expected that future devices that perform this function will also be calibrated in the same manner. The type of injection device is not considered a limiting aspect of the present invention. The primary importance of a pulse voltage device is, in fact, the capability of the device to facilitate delivery of compositions of the invention into the cells of an organism. The pulse voltage injection device can include, for example, an electroporetic apparatus as described in U.S. Pat. Nos. 5,439,440, 5,704,908 or 5,702,384 or as published in PCT WO 96/12520, PCT WO 96/12006, PCT WO 95/19805, and PCT WO 97/07826, all of which are incorporated herein by reference in their entirety.

The term "apparatus" as used herein relates to the set of components that upon combination allow the delivery of compositions of the invention into the cells of an organism by pulse voltage delivery methods. The apparatus of the invention can be a combination of a syringe or syringes, various combinations of electrodes, devices that are useful for target selection by means such as optical fibers and video monitoring, and a generator for producing voltage pulses which can be calibrated for various voltage amplitudes, durations and cycles. The syringe can be of a variety of sizes and can be selected to inject compositions of the invention at different delivery depths such as to the skin of an organism such as a mammal, or through the skin.

The term "organism" as used herein refers to common usage by one of ordinary skill in the art. The organism can include microorganisms, such as yeast or bacteria, plants, birds, reptiles, fish or mammals. The organism can be a companion animal or a domestic animal. Preferably the organism is a mammal and is therefore any warmblooded organism. More preferably the mammal is a human.

The term "companion animal" as used herein refers to those animals traditionally treated as "pets" such as for example, dogs, cats, horses, birds, reptiles, mice, rabbits, hamsters, and the like. The term "domestic animal" as used herein refers to those animals traditionally considered domesticated, where animals such as those considered "companion animals" are included along with animals such as, pigs, chickens, ducks, cows, goats, lambs, and the like.

By "prolong the localized bioavailability of a nucleic acid" is meant that a nucleic acid when administered to an organism in a composition comprising such a compound will be available for uptake by cells for a longer period of time than if administered in a composition without such a compound, for example when administered in a formulation such as a saline solution. This increased availability of nucleic acid to cells could occur, for example, due to increased duration of contact between the composition containing the nucleic acid and a cell or due to protection of the nucleic acid from attack by nucleases. The compounds that prolong the localized bioavailability of a nucleic acid are suitable for internal administration.

By "suitable for internal administration" is meant that the compounds are suitable to be administered within the tissue of an organism, for example within a muscle or within a joint space, intradermally or subcutaneously. Other forms of administration which may be utilized are topical, oral, pulmonary, nasal and mucosal; for example, buccal, vaginal or rectal. Properties making a compound suitable for internal administration can include, for example, the absence of a high level of toxicity to the organism as a whole.

By "solutions" is meant water soluble polymers and/or surfactants in solution with nucleic acids.

Polymeric Formulations for Plasmid Delivery to Muscle

The present invention provides polymeric formulations that address problems associated with injection of nucleic acids suspended in saline. Unformulated (naked nucleic acid molecules) plasmids suspended in saline have poor bioavailability in muscle due to rapid degradation of plasmid by extracellular nucleases. One possible approach to overcome the poor bioavailability is to protect plasmid from rapid nuclease degradation by, for example, condensing the plasmid with commonly used cationic complexing agents. However, due to the physiology of the muscle, the use of rigid condensed particles containing plasmid for efficient transfection of a larger number of muscle cells has not been successful to date. Cationic lipid and polylysine plasmid complexes do not cross the external lamina to gain access to the caveolae and T tubules (Wolff, J. A., et al., 1992, *J. Cell. Sci.* 103:1249-1259).

Thus, the invention increases the bioavailability of plasmid in muscle by: protecting plasmid from rapid extracellular nuclease degradation; dispersing and retaining intact plasmid in the muscle and/or tumor; and facilitating the uptake of plasmid by muscle and/or tumor cells. A specific method of accomplishing this, which preferably is used in conjunction with pulse voltage delivery, is the use of anionic polymers.

Administration

Administration as used herein refers to the route of introduction of a plasmid or carrier of DNA into the body. Administration can be directly to a target tissue or by targeted delivery to the target tissue after systemic administration. In particular, the present invention can be used for treating conditions by administration of the formulation to the body in order to establish controlled expression of any specific nucleic acid sequence within tissues at certain levels that are useful for gene therapy.

The preferred means for administration of vector (plasmid) and use of formulations for delivery are described above. The preferred embodiments are by pulse voltage delivery to cells in combination with needle or needle free injection, or by direct applied pulse voltage wherein the electroporation device's electrodes are pressed directly against the targeted tissue or cells, such as for example epidermal cells, and the vector is applied topically before or after pulse application and delivered through and or to the cells.

The route of administration of any selected vector construct will depend on the particular use for the expression vectors. In general, a specific formulation for each vector construct used will focus on vector delivery with regard to the particular targeted tissue, the pulse voltage delivery parameters, followed by demonstration of efficacy. Delivery studies will include uptake assays to evaluate cellular uptake of the vectors and expression of the DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

Muscle cells have the unique ability to take up DNA from the extracellular space after simple injection of DNA particles as a solution, suspension, or colloid into the muscle. Expression of DNA by this method can be sustained for several months.

The chosen method of delivery should result in expression of the gene product encoded within the nucleic acid cassette at levels that exert an appropriate biological effect. The rate of expression will depend upon the disease, the pharmacokinetics of the vector and gene product, and the route of administration, but should be in the range 0.001-100 mg/kg of body weight/day, and preferably 0.01-10 mg/kg of body weight/day. This level is readily determinable by standard methods. It could be more or less depending on the optimal dosing. The duration of treatment will extend through the course of the disease symptoms, possibly continuously. The number of doses will depend upon the disease, delivery vehicle, and efficacy data from clinical trials.

DNA Injection Variables

The level of gene delivery and expression or the intensity of an immune response achieved with the present invention can be optimized by altering the following variables. The variables are: the formulation (composition, plasmid topology), the technique and protocol for injection (area of injection, duration and amplitude of voltage, electrode gap, number of pulses emitted, type of needle arrangement, pre-injection-pulsed or post-injection-pulsed cells, state of muscle, state of the tumor), and, the pretreatment of the muscle with myotoxic agents. An immune response can be measured by, but is not limited to, the amount of antibodies produced for a protein encoded and expressed by the injected nucleic acid molecule.

Other injection variables that can be used to significantly affect the levels of proteins, antibodies and/or cytotoxic T-lymphocytes produced in response to the protein encoded by the formulated nucleic acid molecule provided by the pulse voltage injection method of the present invention are the state of the muscle being injected and injection technique. Examples of the variables include muscle stimulation, muscle contraction, muscle massage, delivery angle, and apparatus manipulation. Massaging the muscle may force plasmid out of the muscle either directly or via lymphatic drainage. By altering the depth of penetration and/or the angle at which the pulse voltage device is placed in relation to muscle fibers the present invention improves the plasmid distribution throughout the injection area that subsequently increases the antibody response to the protein which is encoded and expressed by the plasmid.

Nucleic Acid Based Therapy

The present invention can be used to deliver nucleic acid vaccines in a more efficient manner than is conventionally done at the present time. Nucleic acid vaccines, or the use of plasmid encoding antigens or therapeutic molecules such as Human Growth Hormone, has become an area of intensive research and development in the last half decade. Comprehensive reviews on nucleic acid based vaccines have been published (M. A. Liu, et al. (Eds.), 1995, *DNA Vaccines: A new era in vaccinology*, Vol. 772, Ann. NY. Acad. Sci., New York; Kumar, V., and Sercarz, E., 1996, *Nat. Med.* 2:857-859; Ulmer, J. B., et al., (Eds.) *Current Opinion in Immunology;* 8:531-536. Vol. 772, Ann. NY. Acad. Sci., New York). Protective immunity in an animal model using plasmid encoding a viral protein was first observed in 1993 by Ulmer et al. (Ulmer, J. B., et al., 1993, *Science* 259:1745-1749). Since then, several studies have demonstrated protective immunity for several disease targets and human clinical trials have been started.

Many disease targets have been investigated. Examples include antigens of *Borrelia burgdorferi*, the tick-borne infectious agent for Lyme disease (Luke et al., *J. Infect. Dis.* 175:91-97, 1997), human immunodeficiency virus-1, (Letvin et al., *Proc. Nat. Acad. Sci. USA* 94:9378-9383, 1997), B cell lymphoma (Syrengelas et al., *Nature Medicine.* 2:1038-41, 1996), Herpes simplex virus (Bourne et al., *J. Infectious dis.* 173:800-807, 1996), hepatitis C virus (Tedeschi et al., *Hepatology* 25:459-462, 1997), rabies virus (Xiang et al., *Virology,* 209:569-579, 1995), *Mycobacterium tuberculosis* (Lowrie in Genetic Vaccines and Immunotherapeutic Strategies CAThibeault, ed. Intl Bus Comm, Inc., Southborough, Mass. 01772 pp. 87-122, 1996), and *Plasmodium falciparum* (Hoffman et al., *Vaccine* 15:842-845, 1997). Additionally, nucleic acid based treatment for reducing tumor-cell immunogenicity, growth, and proliferation is indicative of gene therapy for diseases such as tumorigenic brain cancer (Fakhrai et al., Proc. Natl. Acad. Sci., 93:2909-2914, 1996).

An important goal of gene therapy is to affect the uptake of nucleic acid by cells, thereby causing an immune response to the protein encoded by the injected nucleic acid. Nucleic acid based vaccines are an attractive alternative vaccination strategy to subunit vaccines, purified viral protein vaccines, or viral vector vaccines. Each of the traditional approaches has limitations that are overcome if the antigen(s) is expressed directly in cells of the body. Furthermore, these traditional vaccines are only protective in a strain-specific fashion. Thus, it is very difficult, and even impossible using traditional vaccine approaches to obtain long lasting immunity to viruses that have several sera types or viruses that are prone to mutation.

Nucleic acid based vaccines offer the potential to produce long lasting immunity against viral epitopes that are highly conserved, such as with the nucleoprotein of viruses. Injecting plasmids encoding specific proteins by the present invention results in increased immune responses, as measured by antibody production. Thus, the present invention includes new methods of providing nucleic acid vaccines by delivering a formulated nucleic acid molecule with a pulse voltage device as described herein.

The efficacy of nucleic acid vaccines is enhanced by one of at least three methods: (1) the use of delivery systems to increase the stability and distribution of plasmid within the muscle, (2) by the expression (or delivery) of molecules to stimulate antigen presentation/transfer, or (3) by the use of adjuvants that may modulate the immune response.

Diseases and Conditions for Intramuscular Plasmid Delivery

The present invention described herein can be utilized for the delivery and expression of many different coding sequences. The coding sequences may be used to ameliorate the effects of inborn errors of metabolism, genetic deficiencies of certain necessary proteins, acquired metabolic and regulatory imbalances and disordered cellular regulation such as with cancer. The coding sequence containing composition preferably is administered by pulsed voltage delivery and may require, as needed, exposure of the tissue to be treated by surgical means as determined by a certified professional.

EXAMPLES

The following examples are offered by way of illustration and are not intended to limit the scope of the invention in any manner. One of ordinary skill in the art would recognize that the various molecules and/or amounts disclosed in the examples could be adjusted or substituted. It would also be recognized that the delivery targets and/or amounts delivered in the examples could be adjusted or substituted by selecting different muscles for injection, injection into tumors or nodes, or increasing or decreasing the duration of pulse time or alternating the pulse application from pre-injection to post-injection.

Preparation of Formulations

Formulations were made by aliquoting appropriate volumes of sterile stock solutions of water, plasmid, polymer, buffer and/or 5M NaCl to obtain a final plasmid in an isotonic solution. The total plasmid concentration of all formulations was measured by UV absorption at 260 nm. The osmotic pressure of selected formulations was measured using a Fiske One-Ten Micro-Sample Osmometer (Fiske Associates; Norwood, Mass.). The percentage of supercoiled plasmid was measured using 1% agarose gel electrophoresis followed by fluorimaging.

Plasmids were formulated in 5-10 mM Tris, pH 7.5 or saline (150 mM NaCl) or mixed with a polymer in isotonic saline. Plasmid used for injection was formulated with various polymers in an isotonic saline solution. Typically, the concentration of plasmid was 1-2 mg/ml in saline, or formulated with polyvinylpyrrolidone (PVP, 5%) or 6 mg/ml poly-L-glutamate (Sigma, St Louis, Mo.) in saline.

Anionic polymers included poly-L-glutamic acid (p-L-Glu), sodium salt, of various molecular weights (degree of polymerization (DP) of 9 (Sigma P1943), degree of polymerization of 10 (Sigma P1818),2-15 kDa (Sigma P4636),15-50 kDa (Sigma P4761) and 50-100 kDa (Sigma P4886)), poly-D-glutamic acids (p-D-Glu) of 15-50 (Sigma P4033) and 50-100 kDa (Sigma 4637), poly-L-aspartic acid (p-L-Asp), sodium salt, of 2-15 (Sigma P5387) and 15-50 kDa (Sigma P6762) and poly-acrylic acid (pAA), sodium salt, of 5 and 60 kDa. The polyamino acids were purchased from Sigma (St. Louis, Mo.), while the poly(acrylic acid) was acquired from Fluka (Switzerland).

The DNA/anionic polymer formulations were preferably prepared by aliquoting appropriate volumes of sterile stock solutions of plasmid, anionic polymer and 5M NaCl to obtain selected final plasmid and anionic polymer concentrations. The anionic polymer was added to the DNA solution prior to adding salt for tonicity adjustment. Thus, poly-L-glutamate formulations are preferably prepared by combining an aqueous stock solution of sodium poly-L-glutamate (sodium salt of poly-L-glutamic acid) with a stock solution of purified plasmid DNA in saline or up to 10 mM Tris, pH 7.5. After the poly-L-glutamic acid and DNA are combined, the solution is adjusted to a final concentration of 150 mM NaCl by addition of a stock solution of 5M NaCl.

The osmolality of each formulation was measured using a Fiske One-Ten Micro-Sample Osmometer (Fiske Associate, Norwood Mass.). Formulations were also characterized by measuring the optimal density at 260 and 280 nm, and by determining plasmid conformation on a 1% agarose gel.

Stability Test for Plasmid in the Formulation

For the analysis of pDNA stability in the formulation, 50 ng of formulated pDNA with 5 microliters of tracking dye was loaded into 1% agarose gel in 1% tris-acetate-EDTA (TAE) buffer and run the gel at 100 volts for 1-2 hours. The gel was then stained with SYBR Green II (Molecular Probes, Inc.) for 20 minutes. The stained gel was washed with water and % of supercoiled and open circled DNA was determined using a Fluorinate (Molecular Dynamics Co., Sunnyvale, Calif.).

Elisa Protocol

High affinity assay plates were coated with antigen diluted in PBS (50 microliters/well) and placed at 4° C. overnight. After allowing plate(s) to come to room temperature, all wells were blocked with 200 microliters/well of 4% BSA/4% NGS solution made in 1× PBS/Tween20 for 1 hr at 37° C. Add serum samples (50 microliters/well at a starting dilution of 1:100 in 4% BSA/4% NGS/PBS/Tween20, in duplicate) and incubate for 1-2 hours at 37° C. Wash plate(s) with PBS/Tween 20 and add 50 microliters/well of HRP-conjugated secondary, diluted in 1% BSA, and incubate at 37° C. for 1 hour. Wash plate(s) with PBS/Tween 20 and add 100 microliters/well of TMB soluble reagent. Incubate at room temperature for 10 minutes and stop the reaction by adding 50 microliters/well of 0.2M $H_2SO_4$. Read plate(s) at 450 nm.

Plasmids

Plasmids pAP1166 and pFN0945 (SEQ. ID. NO. 3) containing a CMV enhancer-promoter and either a human placental secreted alkaline phosphatase reporter gene (SEAP) (pAP1166) or the coding region of hF.IX (pFN0945 SEQ. ID. NO. 3) were manufactured and purified at Valentis, Inc. The plasmid map of pFN0945 is shown in FIG. 17. Human factor IX (hF.IX) plasmid was prepared by inserting a synthetic coding sequence in which rare codons were converted to prevalent ones and potential cryptic splice sites were abrogated (Oberon Technologies Inc., Alameda, Calif.). The hF.IX coding sequence was inserted into the Valentis plasmid backbone containing a 107 bp 5'TR, a 117 bp synthetic intron, the human growth hormone polyadenylation signal, a PUC12 origin of replication and a kanamycin resistance gene. The hF.IX gene was driven by the CMV enhancer/promoter. Plasmids were grown in *Escherichia coli* DH5α and were purified using a proprietary method involving alkaline lysis and chromographic methods (Abruzzese, R. V., et al. (1999) *Hum Gene Ther* 10:1499-1507, incorporated herein by reference). The human secreted alkaline phosphatase (SEAP) and human erythropoietin plasmids were identical to the hF.IX plasmid except for the coding region.

Experimental Animals

Male C57BL/6 mice (19-21 g), male CD-1 mice (29-31 g), male C.B-17/lcrCrl-scid-bgBR (SCID BEIGE) mice (7 weeks of age) and female C57BL/6 mice (7-8 weeks) were obtained from Charles River Laboratories and were acclimatized for a 3-7 day period in a 12 hour light-dark cycle at 23° C./40% RH in accordance with state and federal guidelines. Food (Purina rodent chow) and water were provided ad libitum. The animals were housed in hepa-filtered caging units (4 mice per isolator) with sterilized bedding food and water. Cage exchange and all manipulations with the SCID mice were performed in a laminar flow hood. Animals were anesthetized via intraperitioneal (IP) injection with a combination anesthesia (Ketamine, Xylazine and Acepromazine) at a dose of 1.8-2.0 mL/kg (mice). Beagle dogs (Harlan, Indianapolis, Ind.) were maintained at Stillmeadow, Inc. (Sugarland, Tex.) in accordance with the guidelines of the Institutional Animal Care and Use Committee.

Animal Injections

After anesthesia, hind limbs were shaved and scrubbed with betadine followed by 70% ethanol. 10 microliters of the formulation was injected with 10 micrograms of formulated plasmid using a 0.3-ml insulin syringe with a 28-gauge, 0.5 needle (Becton Dickinson, Granklin Lake, N.J.). The injected volumes in mice were 25 microliters and 50 microliters in the cranial tibialis and gastrocnemius, respectively. Where indicated, seven days after formulation injection, the animals were sacrificed by $CO_2$ asphyxiation and the tibialis anterior muscles was harvested, quickly immersed in liquid nitrogen, and lyophilized overnight. The dried muscles were used or stored at −80° C. for further determination of reporter gene activity.

Device and Dosing Regimens

Plasmid formulated at the required dose was administered in rodents by longitudinal injection in both tibialis cranialis or in both gastrocnemius muscles (bilateral administration). By holding the entire lower leg between the caliper electrodes good "electrotransfection" could be obtained. Approximately, two minutes after injection, an electric field was applied in the form of 2 square wave pulses (one per second) of 25 millisecond ("ms") each and 375 V/cm delivered by an Electro Square Porator (T820, BTX, San Diego, Calif.). The clamp electrodes consist of 2 stainless steel parallel plate calipers (1.5 cm $^2$) that are placed in contact with the skin so that the leg is held in a semi-extended position throughout pulse administration. The separation distance of the electrodes is described. Typically the leg of the mouse was positioned between the two plates, which were compressed together until snug with a 3-4 mm separation distance between the plates. Two 25 ms pulses at a voltage of 375 V/cm were then generated with a T-820 Electro Square Porator (Genetronics, San Diego, Calif.). The pulses were administered at a rate of ~1/second.

Dogs were anesthetized with isofluorane for the injection and electroporation procedures. A 6-needle array electrode was used (Genetronics, San Diego, Calif.) (Jaroszeski, M. J., et al. (1997) *Biochim Biophys Acta* 1334:15-18). The electroporation regimen was 6 pulses of 60 ms duration at a voltage of 200 V/cm. The polarity of the pulse was reversed following each pulse under the control of an Auto Switcher (Genetronics, San Diego, Calif.). Following the electroporation procedure the skin above injected muscle was tattooed to identify the injection site for later analysis. Carbon particles were also injected in some of the muscles following electroporation as a marker of the injection site for histological analyses.

In one embodiment, the gene delivery approach uses a low voltage (375 V/cm), long pulse (25 ms) electroporation regimen in mice, in contrast to other protocols that use high voltage (1,800 V/cm) and short pulse (100 μs) parameters (Vicat, J. M., et al (2000) *Hum Gene Ther* 11:909-916).

Serum Assays

Blood samples were collected at the appropriate time points following plasmid administration. Mice were anesthetized IP with Ketamine (60 mg/kg) (Phoenix Scientifics, Inc., St Louis, Mo.). A proparacaine hydrochloride opthalmic solution (Solvay Animal Health Inc., Mendota Heights, Minn.) was applied to the eye. The blood was collected in Microtainer® serum separator tubes (Becton Dickinson, Franklin Lakes, N.J.) and allowed to clot for 15-30 minutes before centrifuging at 7,000 rpm for 5 minutes. Serum levels of SEAP were determined using a chemiluminescence assay (Tropix, Bedford, Mass.) following the manufacturers instructions.

For F.IX assays, blood samples were obtained from the retro-orbital plexus of mice. Approximately 250 microliters of blood were collected in EDTA microtainer tubes (Becton Dickinson, Franklin Lakes, N.J.). The blood was centrifuged at ~5,000 g for 5 minutes. Plasma samples were frozen at −80° C. and stored until used for analysis. Plasma hF.IX levels were determined using the Asserachrom IX:Ag human F.IX ELISA kit (Diagnostica Stago, France). Purified human F.IX (Sigma, St. Louis, Mo.) was used to generate a standard curve. For dogs, blood was collected from the jugular vein of conscious animals into EDTA plasma tubes. Reference plasma for the ELISAs was obtained from each animal prior to treatment. Serum levels of erythropoietin were determined using a commercially available ELISA kit from R&D Systems (Minneapolis, Minn.).

Western Blot Analysis

Purified hF.IX (Sigma, St. Louis, Mo.) in sample buffer (0.5 M Tris, 1.5% SDS, 4% β-mercaptoethanol, 10% glycerol, 0.03% bromphenol blue) was loaded on a 10% glycine Tris polyacrylamide gel (Novex, San Diego, Calif.). Following electrophoresis, protein was transferred to a nitrocellulose membrane (Novex, San Diego, Calif.). The membranes were then incubated first in canine plasma (1:50) from either treated animals or normal dogs (negative control). For the positive control the membrane was incubated in normal canine plasma spiked with rabbit anti-hF.IX antibody (1:1,000 final). The second antibody was either horseradish peroxidase (HRP)-conjugated rabbit anti-canine antibody (Sigma, St. Louis, Mo.) or HRP conjugated sheep anti-rabbit antibody (Sigma, St. Louis, Mo.). Bands on the blots were visualized using a peroxidase substrate kit (Vector Laboratories Inc., Burlingame, Calif.).

Creatine Kinase (CK)

Serum collected from the dogs was frozen and shipped on dry ice by overnight courier to IDEXX Veterinary Services (West Sacramento, Calif.) for analysis of CK levels by standard methodology.

Histological Analysis and Fiber-Typing

For hF.IX immunohistochemistry in mouse tissue a method modified from Herzog et al. (1997) *Proc. Natl. Acad. Sci. USA* 94(11), 5804-5809, was used. Briefly, 10 micrometer cryosections of tissue were fixed in 3% paraformaldehyde for 15 minutes, rinsed in PBS, treated with methanol for 10 minutes, washed three times in PBS and then blocked in 20% normal goat serum. Sections were subsequently incubated for 1 hour with an affinity-purified rabbit anti-hF.IX (Dako Corp., Carpinteria, Calif.) that was diluted 1:6,000 in PBS/1% BSA. The sections were rinsed PBS and incubated with biotinylated goat anti-rabbit IgG (Vector Laboratories, Burlingame, Calif.) diluted 1:400 in PBS for 30 minutes. The sections were rinsed and hF.IX staining was visualized using the Elite ABC reagent (Vector Laboratories, Burlingame, Calif.) at a dilution of 1:80 for 30 minutes followed by a 5 minute incubation in a DAB solution (Vector Laboratories, Burlingame, Calif.). The sections were counterstained with Mayer's hematoxylin (VWR, Houston, Tex.). All incubation steps were at room temperature.

For ATPase fiber subtyping, 10 micrometers of muscle tissue cryosections (serial sections of those used for the hF.IX staining) were incubated for 5 minutes in barbital acetate buffer, pH 4.6, transferred to ATPase solution, pH 9.4, for 20 minutes, washed three times in 1% calcium chloride, washed for 5 minutes in 2% cobalt chloride, washed ten times in 0.01 M sodium barbital wash solution, and rinsed in distilled water for 5 minutes. To visualize the ATPase activity, sections were dipped into 1.5% ammonium sulfide for 20 seconds, rinsed in distilled water, dehydrated in ethanol, and coverslipped. At pH 4.6, type I fibers stain dark brown, type IIA fibers stain very light brown and type IIB fibers are intermediate.

For dogs, muscle samples were harvested and immediately placed in 10% neutral buffered formalin overnight at room temperature. The tissue was dehydrated using alcohol and then embedded in paraffin. Sections were cut and stained with Mayer's hematoxylin and eosin (Sigma, St. Louis, Mo.).

All microscopy was performed with an Olympus BX-40 (Olympus America, Melville, N.Y.) microscope equipped with a DXC-960MD color video camera (Sony Corp., Japan).

Example I

Determination of Formulation and Delivery Parameters Using Reporter Genes

Formulating DNA with anionic polymers increases electroporation-mediated gene expression after an intra-muscular injection. An example of an anionic polymer is an excess of non-coding DNA, which can increase transgene expression. The protocol that was regularly used to transfect the myofibers of CD-1 or C57BL/6 mice consisted of an injection of a DNA solution followed, two minutes later, by the electroporation of the injected muscle with a clamp electrode. A constant mass (0.75 micrograms, 2.5 micrograms or 15 micrograms) of a plasmid DNA coding for the SEAP (human placental secreted alkaline phosphatase) gene with various amounts of an empty plasmid was co-injected in the tibialis cranialis muscle of CD-1 mice. Empty plasmid means that the plasmid does not carry the coding sequences for SEAP or, preferably, any other gene.

Figure 1:
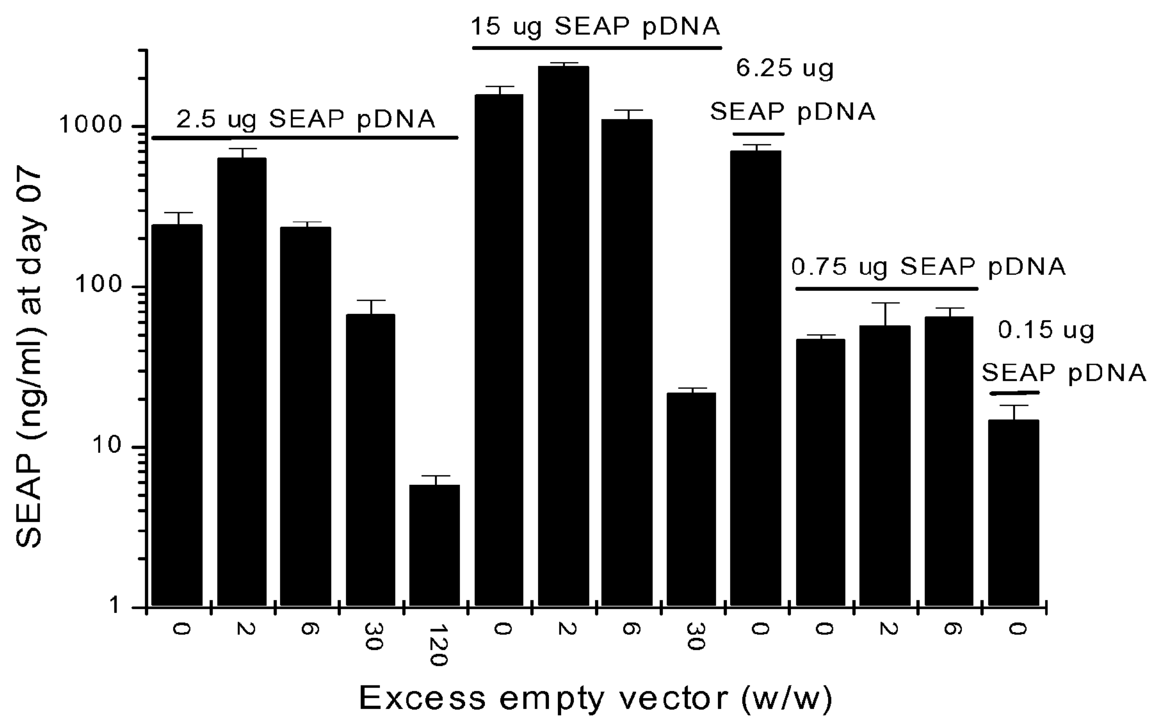
FIG. 1 shows SEAP serum concentrations at day 7 post injection of SEAP pDNA/empty DNA mixtures in the tibialis cranialis muscle of CD-1 mice with electroporation. Various SEAP pDNA amounts and empty pDNA excess (relative to the coding pDNA) were administered.

FIG. 1 shows SEAP serum concentrations at day 7 post injection of SEAP pDNA/empty DNA mixtures in the tibialis cranialis muscle of CD-1 mice and electroporation of the tissue. Various SEAP pDNA amounts (0.15 micrograms, 0.75 micrograms, 2.5 micrograms, 6.25 micrograms and 15 micrograms) and empty pDNA excess (relative to the coding pDNA) were administered in 50 microliters per animal (half this dose per leg). For each dose of SEAP pDNA tested, SEAP concentration in the serum at the peak of expression (day 7 post injection/electroporation) increased substantially when a 2-fold excess of empty pDNA was co-administered with the coding pDNA. For instance, SEAP expression in these conditions with 2.5 micrograms SEAP pDNA was similar to that obtained with 6.25 micrograms SEAP pDNA without an empty plasmid. When the amount of SEAP pDNA administered was 2.5 or 15 micrograms, increasing further the excess of empty vector (6, 30 and 120-fold) resulted in a continuous decrease of SEAP expression. Conversely, for the lowest amount of coding pDNA (0.75 micrograms), SEAP expression was maintained when a 6-fold excess of empty DNA was co-injected.

This non-monotonous evolution of SEAP expression as the amount of empty DNA pre-mixed with the SEAP pDNA is increased reflects the interplay of two phenomena. First, the addition of the empty pDNA enhances gene expression due to the saturation of a DNA degradation mechanism or the saturation of a process that deactivates the DNA (e.g., binding to cationic entities such as divalent cations or histones, in the interstitial fluid and in the myocytes nuclei, respectively). This effect can result either in an increased intracellular (or intranuclear) uptake or in a more efficient processing of the SEAP pDNA in the nucleus. Second, the empty vector competes with the SEAP-coding DNA in some of the steps that leads to transcription of the transgene, which results in a decrease of SEAP expression. These steps include the distribution of the DNA in the interstitial fluid prior to electroporation, the intracellular entry through the electropores, the trafficking to the nuclei, the entry in the nuclei and the binding to transcription factors.

Thus, polynucleotides having non-coding sequences or preferably random sequences may function to protect against degradation in vivo of plasmid carrying a gene intended to be expressed in an animal.

In addition to using polynucleotides or empty plasmid to enhance transgene expression and protect against degradation, other anionic polymers may also be used. These anionic polymers may include poly-amino acids (such as poly-L-glutamic acid, poly-D-glutamic acids, poly-L-aspartic acid, poly-D-aspartic, and combination thereof) or poly-organic acids (such as poly-acrylic acid) which exhibit beneficiary effects similar to the empty plasmid, but which do not compete with the SEAP pDNA in the processes described above.

Figure 2:
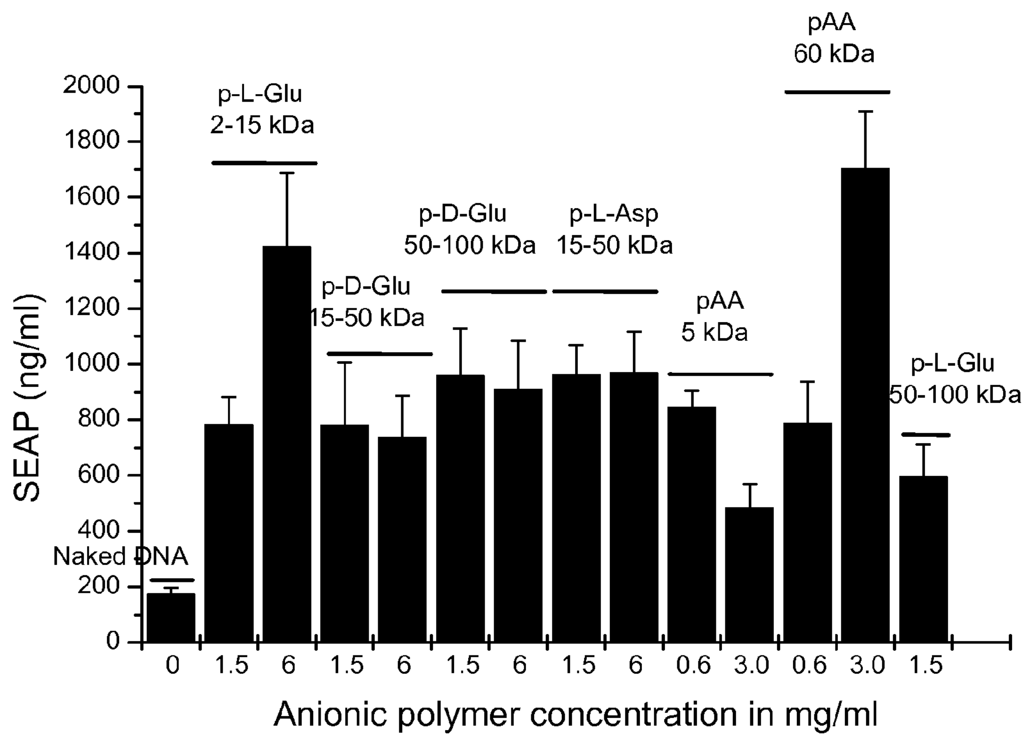
FIG. 2 shows SEAP serum concentrations at day 7 post injection of naked SEAP pDNA or SEAP pDNA/anionic polymer mixtures in the tibialis cranialis muscle of CD-1 mice with electroporation and DNA concentration of 2.5 micrograms in 50 microliters (half this dose per leg). The concentration of the anionic polymer in the injected solution varied as indicated on the graph.

Some anionic polymers were found to be considerably more potent than non-coding DNA to increase transgene expression. Anionic polymers with various origins, molecular weights, conformations and charge densities were mixed at various concentrations with the SEAP pDNA (0.05 mg/ml) prior to injection in the tibialis cranialis muscle of CD-1 mice. Seven days after the injection/electroporation procedure (at the peak of expression), SEAP serum concentrations were determined (FIG. 2). At the low DNA dose tested (1.25 micrograms per tibialis), some of the anionic polymers selected considerably increased SEAP expression. The highest SEAP levels were obtained with the 60 kDa poly-acrylic acid (pAA) at 3.0 mg/ml and the 2-15 kDa poly-L-glutamic acid at 6.0 mg/ml. Co-administration of these anionic polymers with the SEAP pDNA enhanced expression by 10 and 8-fold, respectively (FIG. 2).

In order to characterize further the beneficiary effect provided by the anionic polymers, the same type of experiment as that mentioned above was carried out, but at a 10-fold higher DNA concentration of 0.5 mg/ml. FIG. 2 shows SEAP serum concentrations at day 7 post injection of naked SEAP pDNA or SEAP pDNA/anionic polymer mixtures in the tibialis cranialis muscle of CD-1 mice and electroporation of the tissue. The amount of SEAP pDNA administered per animal was 2.5 micrograms in 50 microliters (half this dose per leg). The concentration of the anionic polymer in the injected solution varied as indicated on the graph. FIG. 3 shows the same thing as FIG. 2, except that the amount of SEAP pDNA administered per animal was regularly (unless mentioned) 25 micrograms in 50 microliters (half this dose per leg). The concentration of the anionic polymer (or anionic monomer when applicable) in the injected solution varied as indicated on the graph.

At this high DNA concentration, the range of enhancements in SEAP expression resulting from the addition of an anionic polymer was lower than that observed previously (FIG. 2, 3). In particular, the poly-acrylic acids, highly efficient at a low DNA dose, were almost inactive. However, the polypeptides still increased SEAP expression substantially (up to 2-fold with the 2-15 kDa poly-L-glutamic acid at 6.0 mg/ml). This result was particularly remarkable given that SEAP expression was reaching a plateau at this concentration of DNA. Indeed, when the DNA was administered "naked", SEAP expression was enhanced by only 50% and 15% following an increase in DNA concentration by 3-fold (from 0.5 mg/ml to 1.5 mg/ml) and 10-fold (to 5.0 mg/ml), respectively (FIG. 3).

The fact that the L-glutamic acid monomer was unable to increase expression, in contrast to the 2-15 kDa polymer (FIG. 3), demonstrated that a macromolecule is necessary to provide the effect that leads to higher expressions. When the results from the two separate experiments partially displayed in FIG. 2 and FIG. 3 are gathered in the composite graph (FIG. 5A), the evolution of SEAP expression as a function of DNA concentration can be compared for the naked DNA injection and two of the DNA/anionic polymers treatments (namely DNA/2-15 kDa poly-L-glutamic acid at 6.0 mg/ml and DNA/60 kDa poly-acrylic acid (pAA) at 3.0 mg/ml). Two different trends appear clearly after adding an anionic polymer to the DNA solution. In the case of the 60 kDa poly-acrylic acid, the increase in SEAP expression (compared to naked DNA) is high but restricted to low and intermediate DNA concentrations. In the case of the 2-15 kDa poly-L-glutamic acid, the levels of expression are slightly lower in this range of DNA concentrations, but the beneficiary effect is still substantial at high DNA concentrations.

The injection/electroporation procedure was conducted in the gastrocnemius muscle of CD-1 mice, instead of the tibialis cranialis, to determine if the increase in expression provided by some anionic polymers is specific to the muscle used for expression. The anionic polymers selected were those that yielded the highest levels of expression in the studies described above, i.e., the 2-15 kDa and 50-100 kDa poly-L-glutamic acids as well as the 60 kDa poly-acrylic acid. Two DNA concentrations were tested in this study, i.e., 0.3 mg/ml (15 micrograms injected per gastrocnemius) and 1 mg/ml. FIG. 4 shows SEAP serum concentrations at day 7 post injection of naked SEAP pDNA or SEAP pDNA/anionic polymer mixtures in the gastrocnemius muscle of CD-1 mice and electroporation of the tissue. The amount of SEAP pDNA administered per animal was either 30 micrograms, 100 micrograms or 300 micrograms in 100 microliters (half this dose per leg). The concentration of the anionic polymer in the injected solution varied as indicated on the graph.

The three polymers yielded a substantial increase in expression at the low DNA dose (FIG. 4). Conversely to what was observed when the injections were performed in the tibialis cranialis muscle, the 60 kDa poly-acrylic acid was most efficient at its lowest concentration of 0.6 mg/ml and was less potent than the poly-L-glutamic acids used at 6.0 or 12.0 mg/ml. In the best conditions tested (50-100 kDa poly-L-glutamic acid at 6.0 mg/ml), SEAP expression was increased by 8-fold over that obtained with naked DNA. At the higher DNA concentration, the trends described above were accentuated. The 60 kDa poly-acrylic acid was either inactive or inhibitory at high concentrations, whereas the poly-L-glutamic acids were still yielding a 2 to 3-fold increase in expression. Again, this result was particularly remarkable, given that the expression levels achieved with the naked DNA treatment were only increased by 10% when the DNA concentration was elevated to 3.0 mg/ml instead of 1.0 mg/ml.

Figure 5A:
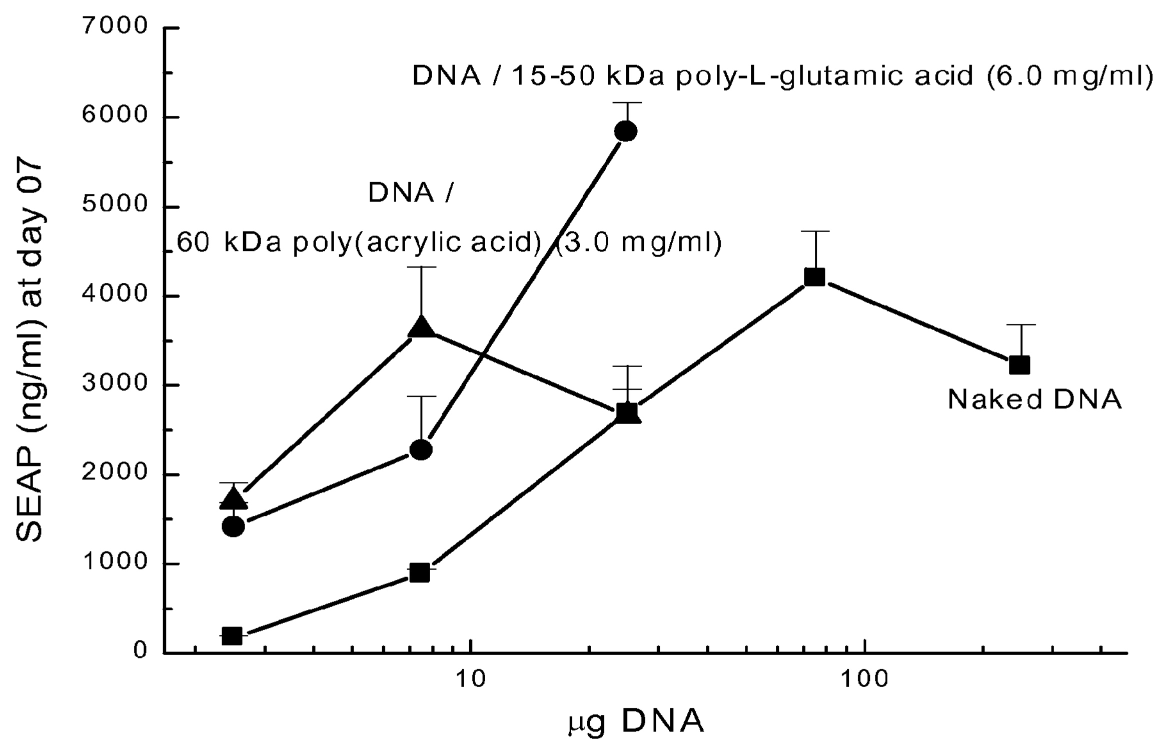
Figure 5B:
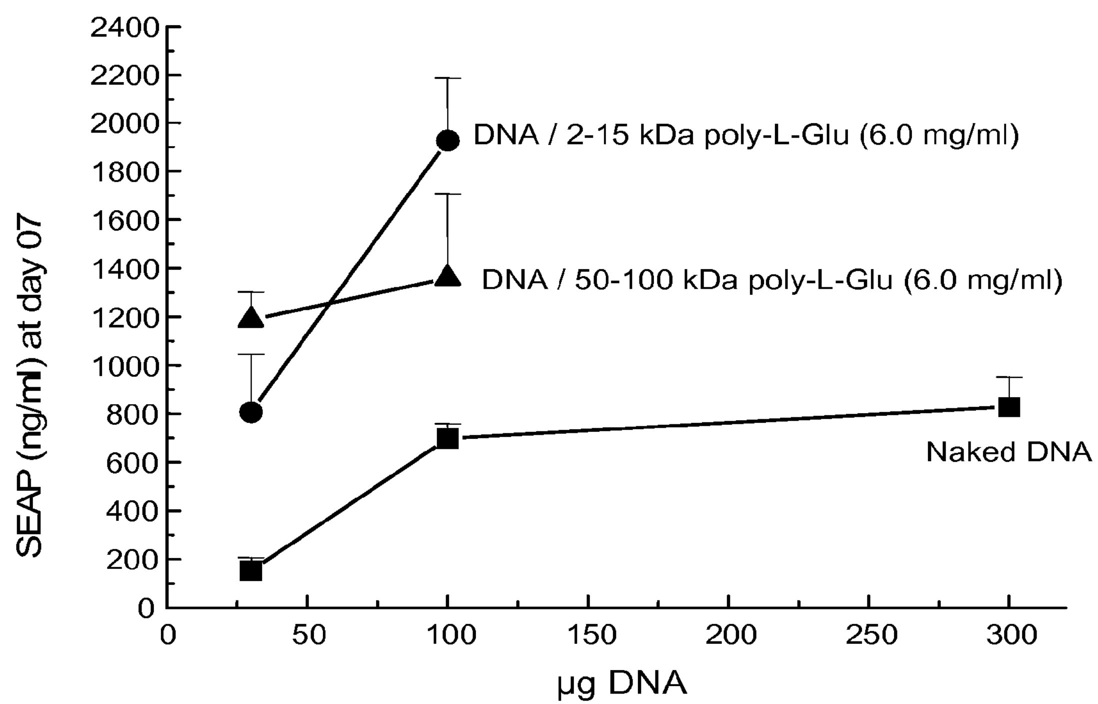

FIG. 5A shows SEAP serum concentrations at day 7 as a function of the amount of SEAP pDNA injected in the tibialis cranialis muscle of CD-1 mice. Solutions administered two minutes before electroporation consisted of either naked SEAP pDNA or a mixture of SEAP pDNA and a 60 kDa poly-acrylic acid at 3.0 mg/ml or a mixture of SEAP pDNA and a 2-15 kDa poly-L-glutamic acid at 6.0 mg/ml. FIG. 5B shows SEAP serum concentrations at day 7 as a function of the amount of SEAP pDNA injected in the gastrocnemius muscle of CD-1 mice. Solutions administered two minutes before electroporation consisted of either naked SEAP pDNA or a mixture of SEAP pDNA and a poly-L-glutamic acid at 6.0 mg/ml. When the SEAP serum concentration at day 7 post-injection is plotted as a function of the amount of DNA injected per animal as in FIG. 5B, the beneficiary effect of the poly-L-glutamic acids (at 6.0 mg/ml) on expression appears clearly.

Example II

Determination of Reporter Gene Expression Using Poly-Glutamic Acid without Electroporation In order to determine the ability of sodium poly-glutamate to increase the expression of genes encoded on plasmid DNA without electroporation, plasmid DNA formulated in saline was compared with a formulation in sodium poly-glutamate for expression after direct intramyocardial injection in mice.

Plasmid DNA encoding luciferase (pLC0888) was formulated in saline or 6% sodium poly-L-glutamate ((Sigma P4636) at plasmid concentrations of 1 and 3 mg/mL. A total of twenty CD-1 male mice (29-31g) were used. The myocardium was injected directly after surgical exposure. Ten (10) microliters of formulation (using a 3/10 cc insulin syringe) were injected into the apex of the heart (i.e., left ventricle). The heart was repositioned and the thorax sutured. Seven days after injection, the hearts were removed and snap frozen in liquid nitrogen, and stored at −80° C. until needed for analysis. For analysis, heart muscle was bead-beat for 2 minutes prior to addition of 1 milliliter of 0.5× Lysis buffer. The tissue was bead-beat for 5 minutes and centrifuged for 10 mins at 13,000 rpm. The supernatants were assayed for luciferase activity. The results of luciferase expression at 7 days after injection are shown in FIG. 6. Each bar represents n=5. As shown in FIG. 6, plasmid DNA formulated with poly-L-glutamate increased gene expression several fold over saline.

Example III

Expression of Therapeutic Genes Factor IX Expression Using Polymer Formulations In addition to reporter genes, experiments were also performed using poly-L-glutamic acids to increase the expression of a therapeutic gene, namely that coding for the coagulation factor IX. The potency of these anionic polymers was tested with pFN0945 (SEQ. ID. NO. 3 and FIG. 17) at DNA concentrations (0.5 mg/ml and 1.0 mg/ml) for which hF.IX expression had reached a plateau. FIG. 7 shows hF.IX serum concentrations at day 7 post injection of naked hF.IX pDNA or hF.IX pDNA/poly-L-glutamic acid mixtures in the tibialis muscle of C57BL/6 mice and electroporation of the tissue. The amount of hF.IX pDNA administered per animal was either 25 μg (0.5 mg/ml) or 50 micrograms (1.0 mg/ml) in 100 microliters (half this dose per leg). The concentration of the anionic polymer in the injected solution varied as indicated on the graph. The poly-L-glutamic acids selected differed by their molecular weight, ranging from 0.5-1.5 kDa (with a degree of polymerization (DP) of 9) to 15-50 kDa. All poly-L-glutamic acids tested were able to increase hF.IX expression substantially, especially at 6.0 mg/ml, with only small differences in potency between polymers. The highest hF.IX level obtained after injection in the tibialis muscle of C57BL/6 mice and electroporation of the tissue was 280 ng/ml, with a treatment consisting of DNA at 0.5 mg/ml and the 2-15 kDa poly(L-glutamic acid) at 6.0 mg/ml. In comparison, the naked DNA treatment only resulted in hF.IX levels around 160 ng/ml.

Persistence of Expression from Plasmid DNA

To determine if hF.IX expression could persist in the plasma for an extended time in the absence of an immune response, plasmid formulated with PVP (5%) was tested in immune deficient SCID beige mice. FIG. 8 shows hF.IX expression in plasma of immune deficient (SCID beige) mice. Mice were initially injected with plasmid (1 mg/ml) formulated with 5% PVP (25 microliters each tibialis muscle and 50 microliters in each gastrocnemius muscle). Consistent with expression patterns in immune competent mice, hF.IX levels peaked 7 days after injection at ~120 ng/ml (FIG. 8). Following a 35% drop in hF.IX levels by 14 days after injection, expression remained fairly stable to 90 days post injection but had fallen to ~20% of peak values by day 125.

At day 153, the animals were re-injected with plasmid and electroporated in the same muscles that were used in the first treatment. For the second injection at day 153 (indicated by the arrow), the animals were separated into two groups. One group was injected with plasmid formulated with 5% PVP (n=7) and the other group injected with plasmid formulated with 6 mg/ml poly-L-glutamate (n=8). The second injections utilized the same injection sites and plasmid dose that were used for the first injections. In both groups of SCID mice, plasmid re-administration led to a significant rise in plasma hF.IX levels. The group injected with plasmid formulated with poly-L-glutamate had significantly higher expression than the group injected with PVP. This difference in expression levels between the groups following the second administration was maintained throughout the duration of the experiment. The kinetics of hF.IX expression in both groups were similar to that seen after the first administration in that there was a significant drop from peak expression (obtained ~7 days after re-injection) within the first two weeks.

The graphs in the insert of FIG. 8 also show the effect of 6 mg/ml poly-L-glutamate on hF.IX and hEPO expression in comparison to saline. For these experiments, the tibialis of mice were injected with plasmid coding for hF.IX (50 micrograms) or for human erythropoietin (75 micrograms) followed by electroporation. Plasma or serum samples were collected 7 days after treatment for analysis. All values are represented as mean±SEM. A Students t-test was used to compare means and in FIG. 8, *=P≦0.05. Plasmids formulated with poly-L-glutamate (6 mg/ml) led to a 1.5 fold to 5.9 fold enhancement in expression compared to plasmid in saline with electroporation and was dependent on the inserted gene (FIG. 8, insert).

In the SCID mice at 10 months after the initial injection with PVP followed by reinjection with a poly-L-glutamate formulation, the tibialis and gastrocnemius muscles were harvested for hF.IX immunostaining and muscle fiber typing. FIG. 9 shows immunohistology and fiber-type of hF.IX expressing myocytes in SCID mouse muscle. Representative sections of SCID mouse gastrocnemius muscle from tissue that was harvested ~300 days after the initial injection. FIG. 9A shows hF.IX immunolocalization wherein positive myocytes are stained dark (original magnification 100×). FIG. 9B shows ATPase staining (pH 4.6) of a serial section of panel A. Type I fibers (dark) and type II fibers (light) are distinguished (original magnification 100×). A representative sample of complementary fibers are labeled in both panels indicating both type I and type II fibers are expressing hF.IX. Both the tibialis and gastrocnemius muscles showed a broad distribution of fibers expressing hF.IX. In the gastrocnemius, expression was found in both type I and type II fibers in roughly equal proportions although the absolute number of stained type I fibers was much lower than type II fibers (FIG. 9). In the mouse tibialis there were few if any type I fibers and thus expression was observed primarily in type II fibers. Thus, long-term expression of hF.IX, achieved in immune compromised (SCID beige) mice, indicates that plasmids are stable and transcriptionally active in muscle for a prolonged period of time.

Applicability to Large Animals

The applicability of the gene delivery procedure to large animals is a necessary prerequisite step for the development of a potentially clinically useful gene therapy. FIG. 10A depicts the results of plasma hF.IX levels in dogs following intramuscular injection of plasmid augmented by electroporation. Six adult dogs (beagles 9-13 kg) were injected with ~1.6 or ~2.8 mg/kg of plasmid using a multiple site protocol and followed by electroporation with 6-needle array electrodes. The DNA was formulated with poly-L-glutamate (6 mg/ml) for these studies. The dogs were divided into two groups. In one group a total dose of 18 mg was administered intramuscularly divided into 6 sites, one in each of the biceps femoris, semimembranosus and cranial tibialis muscles of both rear legs. In the second group, 36 mg of plasmid was administered intramuscularly into 12 sites, one each in the biceps femoris, semimembranosus, semitendinosus, vastus lateralis, cranial tibialis and long head of the triceps brachii muscles of the front and rear limbs. A total volume of 2.0 ml was administered to each site. At each site 2.0 ml of plasmid (1.5 mg/ml) formulated with 6.0 mg/ml poly-L-glutamate was injected followed by electroporation with a 6-needle array electrode. The 6 and 12 injection site groups had 18 mg and 36 mg of plasmid injected per animal, respectively. FIG. 10A shows the results where plasma was collected and analyzed by ELISA. Values are means±SEM with n=3 for each group.

Mean values of the 12 and 6 injection site groups peak at 36.1 ng/ml (day 22) and 27.2 ng/ml (day 14), respectively (FIG. 10A). The values for the two groups diverged at day 22 due to an unexpected increase in mean expression in the group of animals injected at 12 sites. However, the expression levels in this group at day 22 are not significantly higher than at day 14. Regardless of this anomaly, by day 28 expression levels of both groups were indistinguishable from background levels.

Immune Response to Expressed Protein

FIG. 10B shows a western blot of purified hF.IX using treated animal serum as the primary antibody. Lane A represents the molecular weight marker; lane B represents the negative control (i.e., serum from untreated animals); lane C represents the positive control (i.e., canine serum spiked with rabbit anti-hF.IX antibodies); lane D represents the immunoreaction to hF.IX by the serum from a female dog from the 6 injection group (peak expression hF.IX 35.71 ng/ml); lane E represents the immunoreaction to hF.IX by the serum from a male dog from the 12 injection group (peak hF.IX expression 47.9 ng/ml). Thus, analysis by Western blot indicated that plasma from the dogs contained material that cross-reacted with purified hF.IX consistent with an immune response to the human protein (FIG. 10B).

Furthermore, serum analysis also revealed a transient increase in creatine kinase (CK) levels that peaked two days after treatment, and returned to normal levels by 7 days after treatment indicating some muscle trauma is associated with the gene delivery procedure using invasive 6-needle array electrodes. This response is clearly dose dependent with the animals administered the higher dose (12 injection sites) having higher peak levels of CK on day 3 than did the animals from the 6 injection sites group. A histological examination of the different injected muscles revealed some muscle damage approximately 1 month after treatment. In most instances, no histological changes were noted or were restricted to small focal points, where there were indications of myocyte loss and infiltrating monocytes. In rare instances, the injection site was characterized by areas of necrotic tissue and associated myocyte loss. This type of damage was also observed in mice at earlier time points after treatment (2 weeks) when the caliper electrodes were used, but the muscles recovered to normal histology over time (data not shown). There was no indication that a particular muscle type was more susceptible to tissue damage than another.

Expression is Dose Dependant

To establish that expression of hF.IX in canine muscle was dose-dependent, biceps femoris and tibialis cranialis of the left and right hindlimbs of 11-week-old dogs were used for the gene delivery protocol. Formulated plasmid was injected into 4 sites in each dog (left and right tibialis cranialis, left and right biceps femoris). The plasmid concentration was 3.0 mg/ml. Injected volumes (at each site) were 0.12 ml, 0.36 ml, 0.60 ml and 1.2 ml for each group. Serum was collected 7 days after treatment for analysis (peak levels). To normalize for variations in the animals' weight, absolute hF.IX levels are represented (determined by estimating blood volume at 7% of the dogs weight). Values are means±SEM with n=3 for each group. Values are means±SEM per animal with n=4 for each group. Plasma hF.IX levels increased with increasing amounts of plasmid from 0.8 mg/kg up to 2.3 mg/kg. At high doses of plasmid (5.3 mg/kg) mean expression levels were lower than obtained at the 2.3 mg/kg dose but the difference was not significant.

Using plasmid injected into skeletal muscle followed immediately with electroporation, we have achieved therapeutically significant levels of hF.IX expression in the plasma of mice and dogs.

Optimized hF.IX Sequence

The above experiments were performed with plasmid pFN0945 (SEQ. ID. NO. 3 and FIG. 17), which has the natural human nucleic acid sequence encoding for hF.IX. For gene therapy applications in human, pFN0945 may also be used, but a codon optimized sequence for hF.IX may be preferred when higher expression is desired due to higher translation of a codon optimized mRNA. An example of a codon optimized sequence for hF.IX is plasmid pFN1645, which is disclosed as SEQ. ID. NO. 4 and shown in FIG. 18.

Example IV

Expression of Therapeutic Genes

The ability of poly-L-glutamate to increase the expression of a non-viral erythropoietin ("EPO") gene was also undertaken. Using quantitative polymerase chain reaction (qPCR) analysis, plasmid formulated in Poly-L-Glutamate resulted in at least a log increased levels of mEPO DNA compared with animals receiving a saline/DNA formulation.

EPO Expression Using Polymer Formulations

The mEPO coding sequence was inserted into the Valentis plasmid backbone containing a 107 bp 5' UTR, a 117 bp synthetic intron, the human growth hormone polyadenylation signal, a PUC 12 origin of replication and a kanamycin resistance gene as aforementioned. The mEPO gene was driven by the CMV enhancer/promoter. The complete sequence of the resulting plasmid pEP1403 containing the mEPO gene is disclosed in the sequence listing as SEQ. ID. NO. 2 and the plasmid map is shown in FIG. 19. Plasmids were grown in *Escherichia coli* DH5 and were purified using a proprietary method involving alkaline lysis and chromographic methods (Abruzzese, R. V., et al. (1999) *Hum Gene Ther* 10:1499-1507, incorporated herein by reference).

Animals received CMV-mEPO formulated either in 15-50 kDa poly-L-glutamate or in saline. Plasmid formulations were injected intramuscularly in each leg, 25 microliters in each tibialis, 50 microliters in each gastrocnemius followed by electroporation 2 min after injection (375 V/cm (113 V/0.3 cm), 2 pulses, 25 msec pulse length. At defined time intervals, blood was collected by retro-orbital methods and hematocrit levels determined or the serum assayed for EPO levels.

At indicated times, total muscle DNA was extracted and levels of were quantified by qPCR as follows: Plasmid DNA quantities in mouse muscles were determined by conducting TaqMan real time quantitative PCR (Applied Biosystems, Foster City, Calif.) on isolated DNA samples as previously described (Mahato, R. I. et al. *Hum. Gene Ther.* 9, 2083-2099 (1998)). The primers used in the PCR were a forward primer, which primes in the 5' untranslated region, and a reverse primer, which primes in the mouse EPO coding region. The probe sequence was located within the EPO gene. Purified CMV-mEPO plasmid DNA was used to generate a standard curve for the PCR assay. As shown in FIG. 11, formulation in poly-L-glutamate results in a several fold increase in the amount of plasmid DNA that can be detected in tissues after electroporation.

For mEPO expression determination, 75 mg pEP1403 (SEQ. ID. NO. 2) in 150 ml was delivered to C57BL/6 mice, 25 microliters per tibialis, 50 microliters per gastrocnemius. Plasmid was formulated in saline or 6 mg/mL poly-L-glutamate. FIGS. 12 and 13 depict mEPO expression and FIG. 12 also depicts the hemotocrit level in mice following delivery of the mouse EPO gene by electroporation using saline and sodium poly-L-glutamate formulations.

As shown in FIGS. 12 and 13, delivery in a poly-glutamate formulation results in considerably higher levels of expressed protein than when the plasmid DNA is delivered in saline. Because a very small amount of erythropoietin is required to give a maximal increase in hematocrit, the induced hematocrit levels shown on FIG. 12 do not differ between saline and polyglutamate formulations. However, because polyglutamate results in more efficient transfection, it is expected that lower amounts of DNA can be administered using polyglutamate formulations.

Example V

Expression of Therapeutic Genes Interferon Alpha Expression Using Polymer Formulations The hINFα 2b coding sequence was inserted into the Valentis plasmid backbone containing a 107 bp 5' UTR, a 117 bp synthetic intron, the human growth hormone polyadenylation signal, a PUC 12 origin of replication and a kanamycin resistance gene. The hINFα gene was driven by the CMV enhancer/promoter. The complete sequence of the resulting plasmid pIF0921 containing the hINF-α gene is disclosed in the sequence listing as SEQ. ID. NO. 1 and the plasmid map is shown in FIG. 20. Plasmids were grown in *Escherichia coli* DH5α and were purified using a proprietary method involving alkaline lysis and chromographic methods (Abruzzese, R. V., et al. (1999) *Hum Gene Ther* 10:1499-1507, incorporated herein by reference).

For expression analysis, 25 microliters plasmid formulations either in poly-glutamate or in saline that had varying DNA concentrations (1.0 mg/ml, 0.1 mg/ml and 0.01 mg/ml) were injected into each tibialis-both legs were electroporated with caliper electrodes at 375V/cm, 2 pulses, 25 ms each pulse. For analysis, serum was collected via retro orbital bleeds (days 4, 7, 14 and 30). A commercially available ELISA (Endogen) was used to determine INF-α levels. As shown in FIGS. 14A and B, a significant enhancement of hINF-α expression in CD-1 mice was obtained using plasmid formulated with 6 mg/ml poly-L-glutamate at both 5 and 50 microgram DNA doses.

Example VI

Nuclease Protection of Plasmid DNA Formulated in Poly-L-Glutamate

Experiments were undertaken to determine the ability of poly-L-glutamate and Pluronic F68 to protect plasmid DNA from nuclease digestion. DNase I was obtained from Gibco/BRL (#18068-015). The sodium salt of poly-L-glutamic acid, 2-15 kDa was obtained from Sigma. Pluronic F68 was obtained from Spectrum. Polymer/DNA2× stock solutions were prepared (Pluronic F68=200 micrograms/ml plasmid DNA in 10% F68; Poly-L-glutamate=200 micrograms/ml plasmid DNA in 12 mg/ml sodium poly-L-glutamate). DNase dilutions from 1:10 to 1:10,000 were prepared in 1× DNase buffer. The final reaction mixtures included 25 microliters of the formulation, 15 microliters of water, 5 microliters of 10× DNase buffer and 5 microliters of Dnase that were added in the order listed. The reaction mixtures were incubated for 15 minutes at 37° C. and terminated by addition of EDTA prior to gel electrophoresis.

The results of the DNase protection assay are shown in FIG. 15. Panel A represents a DNA in saline formulation; Panel B represents DNA formulated in 5% Pluronic F68; Panel C represents DNA formulated in 6 mg/ml poly-L-glutamate. Lane A represents the negative control (i.e., plasmid DNA without Dnase); lane B represents the positive control (i.e., plasmid DNA and DNase mixed 1:1); lanes C-G represents the experimental conditions wherein DNA formulated with either saline (Panel A), F68 (Panel B), or poly-glutamate (Panel C) were mixed with DNase diluted 1:1 (lane C); 1:10 (lane D);1:100 (lane E); 1:1,000 (lane F); and 1:10,000 (lane G). In saline, DNase at 1:100 is able to abolish the lower band of supercoiled plasmid in addition to degradation of the DNA resulting in a smear of different molecular weights on the gel. In contrast, both poly-L-glutamate and Pluronic F68 were able to confer protection from DNase degradation at 1:100 dilution.

Example VII

Long-Term Biological Stability of DNA formulated in Poly-L-Glutamate

Experiments were also undertaken to evaluate the stability of liquid poly-L-Glutamate (15-50 kDa)/DNA formulations.

Animals: 108 CD-1 mice (29-31g) were obtained from Charles Rivers Labs. The animals were housed in microisolators (10 mice per isolator) in the Laboratory Animal Resource (LAR) vivarium and maintained at 12/12 h day/night cycle, room temperature 72° F. (23° C.), and humidity 40%. Food (Purina rodent chow) and water was provided ad libitum. Combination anesthesia consisting of a mixture of Ketamine (74.0 mg/ml), Xylazine (3.7 mg/ml), and Acepromazine (0.73 mg/ml) was administered IP at a dosage of 1.8-2.0 ml/kg.

Treatment Groups and Routes of Administration: The animals were randomly divided into treatment groups with 6 (tibialis) or 5 (gastrocnemius) mice/group. For the tibialis groups, 25 microliters of the formulations described below were injected in each tibialis muscle, i.e. 50 microliters in total volume per mouse. For the gastrocnemius groups, 50 microliters of the formulations described below were injected in each gastrocnemius muscle, i.e. 100 microliters in total volume per mouse.

Formulations: Formulations were prepared in 150 mM NaCl, 5 mM Tris-HCl, pH 7.5. SEAP encoding plasmid pAP1166.157 at 1 mg/ml was used. Plasmid and poly-L-Glutamate (15-50 kDa) were formulated as follows.

| Formulation | pDNA conc. (mg/ml) | salt | Poly-L-Glu | Buffer |
|---|---|---|---|---|
| A | 1.0 | 150 mM | 6.0 mg/ml | 5 mM Tris/pH 7.5 |
| B | 0 | 150 mM | 6.0 mg/ml | 5 mM Tris/pH 7.5 |

For the liquid formulations, A (0.5 ml) and B (1.5 ml) of the same storage conditions were mixed (or rehydrated with water and mixed for the lyophilized samples) right before use for in-vivo testing (in the gastrocnemius and tibialis muscles of CD-1 mice) and QC analysis. The final DNA concentration of the mixture was 0.25 mg/ml. Each An/Bn couple was tested at day 8, 21, 60 and 105. As a control, a fresh sample of 0.5 ml of A and 1.5 ml of B was tested at every time point. As a fresh naked DNA control, a sample of 0.5 ml of A (A not including poly-L-Glutamate) and 1.5 ml of B (B not including poly-L-Glutamate) was tested at every time point.

The lyophilization/storage conditions for which results are shown in FIG. 16 were the following:

| Group | Physical storage condition | Temperature |
|---|---|---|
| A | Lyophilization (storage N.A. for the sample tested right after completion of the lyophilization cycle) | +4° C. |
| B | Liquid | −20° C. |
| C | Liquid | +4° C. |
| D | Liquid | +25° C. |
| E | Liquid | +37° C. |
| F | Liquid | +50° C. |
| G | Liquid/storage with a freeze/thaw/freeze cycle at day 2, 4 (and 10, 17, 24, 31, 38, 45, 52 and 59 if applicable) | −20° C. |
| H | Fresh DNA/pGlu | |
| I | Fresh naked DNA | |

FIG. 16 depicts the results of the final 105 day time point and indicates the biological activity of the DNA under different storage conditions. As indicated on FIG. 16, plasmid DNA at 1 mg/ml formulated in poly-L-glutamate at 6 mg/ml is stable for over three months in liquid solution at room temperature. Poly-L-glutamate also protected the DNA against degradation during freeze thawing and lyophilization.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations that is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Those references not previously incorporated herein by reference, including both patent and non-patent references, are expressly incorporated herein by reference for all purposes. Other embodiments are within the following claims.

The invention claimed is:

1. A method of delivering a nucleic acid encoding a therapeutic gene product to a cell comprising:

introducing the nucleic acid encoding the therapeutic gene product to a cell in a formulation comprising the nucleic acid formulated with an anionic polymer selected from the group consisting of: poly glutamic acid, poly aspartic acid, poly galacturonic acid, poly vinyl sulfate, and copolymers of glutamic and aspartic acid, and salts thereof, wherein the anionic polymer is non-encapsulating and the formulation does not include a cationic polymer.

2. The method of claim 1, wherein the anionic polymer is selected from the group consisting of poly glutamic acid and poly aspartic acid, and salts thereof.

3. The method of claim 1, wherein the anionic polymer is characterized by a molecular weight in the range from 2,000 to 100,000 Daltons.

4. The method of claim 3, wherein the anionic polymer is characterized by a molecular weight in the range from about 15,000 to about 50,000 Daltons.

5. The method of claim 3, wherein the anionic polymer is characterized by a molecular weight in the range from about 2,000 to about 15,000 Daltons.

6. The method of claim 3, wherein the anionic polymer is characterized by a molecular weight in the range from about 50,000 to about 100,000 Daltons.

7. The method of claim 1, wherein the anionic polymer or salt thereof is formulated with the nucleic acid encoding the therapeutic gene product at a polymer concentration ranging from 1 to 12 mg/ml.

8. The method of claim 7, wherein the anionic polymer or salt thereof is formulated with the nucleic acid encoding the therapeutic gene product at a polymer concentration of about 2 to about 6 mg/ml.

9. The method of claim 1, wherein the formulation is isotonic.

10. The method of claim 1, wherein the formulated nucleic acid is introduced to the cell in a tissue in vivo.

11. The method of claim 10, wherein the tissue is a muscle tissue.

12. The method of claim 1, further comprising a step of storing the formulated nucleic acid by liquid storage, lyophilization and/or freezing.

13. The method of claim 1, wherein the therapeutic gene product is selected from the group consisting of: mRNA templates for translation, ribozymes, antisense RNA, proteins, glycoproteins, lipoproteins, phosphoproteins and polypeptides.

14. The method of claim 13, wherein the therapeutic gene product is a protein selected from the group consisting of growth hormones, growth factors, cytokines, clotting factors, antigens, and antigenic factors.

15. The method of claim 14, wherein the clotting factor is a Factor IX.

16. The method of claim 14, wherein the growth factor is an erythropoietin.

17. The method of claim 14, wherein the cytokine is an interferon.

18. The method of claim 1, wherein the poly glutamic acid is a salt of poly-L-glutamic acid and is present in the formulation at a concentration of 1 to 12 mg/ml.

19. The method of claim 18, wherein the salt of poly-L-glutamic acid is a sodium salt and is present in the formulation at a concentration of about 6 mg/ml.

20. The method of claim 10, wherein the formulated nucleic acid is introduced into the tissue in vivo by injection.

21. The method of claim 10, further comprising a step of electroporating the tissue.

22. The method of claim 21, wherein the electroporating is performed through the use of a device configured and arranged to cause pulse voltage delivery of the formulated nucleic acid.

23. The method of claim 22, wherein the pulse voltage delivery is performed at a pulse strength in a range of about 200V/cm to about 1,800 V/cm.

24. The method of claim 23, wherein the pulse voltage delivery is performed at a pulse strength selected from the group consisting of about: 200V/cm, 375V/cm, and 1,800 V/cm.

25. The method of claim 22, wherein the pulse voltage delivery is performed at a pulse length in the range of about 100 microsec to about 25 millisec.

26. The method of claim 25, wherein the pulse voltage delivery is performed at a pulse length selected from the group consisting of about: 100 microsec 25 millisec, and 60 millisec.

27. The method of claim 22, wherein the pulse voltage delivery is performed using a plurality of pulses.

28. The method of claim 27, wherein the plurality of pulses ranges from 2 to about 6 pulses.

29. The method of claim 22, wherein the pulse voltage delivery is performed using a square wave pulse.

30. The method of claim 22, wherein the method induces an immune response.

31. A method for delivering a therapeutic gene product to a mammalian tissue, comprising the steps of:

providing a non-condensing, non-encapsulating formulation comprising a nucleic acid encoding the therapeutic gene product and an anionic polymer selected from the group consisting of: poly glutamic acid, poly aspartic acid, poly galacturonic acid, poly vinyl sulfate, and copolymers of glutamic and aspartic acid, and salts thereof, introducing the formulation to the mammalian tissue in vivo; and electroporating the tissue, whereby the nucleic acid is introduced into cells in the tissue and the therapeutic gene product is expressed.

32. The method of claim 31, wherein the electroporating is performed through the use of a device configured and arranged to cause pulse voltage delivery of the formulated nucleic acid.

33. The method of claim 32, wherein the pulse voltage delivery is performed at a pulse strength in a range of about 200V/cm to about 1,800 V/cm.

34. The method of claim 33, wherein the pulse voltage delivery is performed at a pulse strength selected from the group consisting of about: 200V/cm, 375V/cm, and 1,800 V/cm.

35. The method of claim 32, wherein the pulse voltage delivery is performed at a pulse length in the range of about 100 microsec to about 25 millisec.

36. The method of claim 35, wherein the pulse voltage delivery is performed at a pulse length selected from the group consisting of about: 100 microsec 25 millisec, and 60 millisec.

37. The method of claim 32, wherein the pulse voltage delivery is performed using a plurality of pulses.

38. The method of claim 37, wherein the plurality of pulses ranges from 2 to about 6 pulses.

39. The method of claim 32, wherein the pulse voltage delivery is performed using a square wave pulse.

40. The method of claim 31, wherein the tissue is a muscle tissue.

41. The method of claim 31, wherein the therapeutic gene product is selected from the group consisting of: mRNA templates for translation, ribozymes, antisense RNA, proteins, glycoproteins, lipoproteins, phosphoproteins and polypeptides.

42. The method of claim 41, wherein the protein is selected from the group consisting of growth hormones, growth factors, cytokines, clotting factors, antigens, and antigenic factors.

43. The method of claim 42, wherein the clotting factor is a Factor IX.

44. The method of claim 42, wherein the growth factor is an erythropoietin.

45. The method of claim 42, wherein the cytokine is an interferon.

46. The method of claim 31, wherein the poly glutamic acid is a salt of poly-L-glutamic acid and is present in the formulation at a concentration of 1 to 12 mg/ml.

47. The method of claim 46, wherein the salt of poly-L-glutamic acid is a sodium salt and is present in the formulation at a concentration of about 6 mg/ml.

* * * * *